(12) United States Patent
Sherman et al.

(10) Patent No.: US 9,895,381 B2
(45) Date of Patent: Feb. 20, 2018

(54) VITAMIN D RECEPTOR AGONISTS TO TREAT DISEASES INVOLVING CXCL12 ACTIVITY

(71) Applicant: Salk Institute for Biological Studies, La Jolla, CA (US)

(72) Inventors: Mara Sherman, San Diego, CA (US); Michael Downes, San Diego, CA (US); Ronald M. Evans, La Jolla, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 14/959,105

(22) Filed: Dec. 4, 2015

(65) Prior Publication Data

US 2016/0089385 A1 Mar. 31, 2016

Related U.S. Application Data

(63) Continuation of application No. PCT/US2014/041063, filed on Jun. 5, 2014.

(60) Provisional application No. 61/831,515, filed on Jun. 5, 2013.

(51) Int. Cl.

| A61K 31/7068 | (2006.01) |
| A61K 45/06 | (2006.01) |
| A61K 31/592 | (2006.01) |
| A61K 31/593 | (2006.01) |
| A61K 31/517 | (2006.01) |
| A61K 31/513 | (2006.01) |
| A61K 47/62 | (2017.01) |
| A61K 47/68 | (2017.01) |
| A61K 9/00 | (2006.01) |
| A61K 31/424 | (2006.01) |
| A61K 31/43 | (2006.01) |
| A61K 31/496 | (2006.01) |

(52) U.S. Cl.
CPC .......... *A61K 31/593* (2013.01); *A61K 31/513* (2013.01); *A61K 31/517* (2013.01); *A61K 31/592* (2013.01); *A61K 31/7068* (2013.01); *A61K 45/06* (2013.01); *A61K 47/62* (2017.08); *A61K 47/6849* (2017.08); *A61K 9/0019* (2013.01); *A61K 31/424* (2013.01); *A61K 31/43* (2013.01); *A61K 31/496* (2013.01)

(58) Field of Classification Search
CPC .. A61K 31/7068; A61K 45/06; A61K 31/592; A61K 31/593
USPC .................................... 435/375; 514/49, 167
See application file for complete search history.

(56) References Cited

U.S. PATENT DOCUMENTS

| 6,358,939 B1 | 3/2002 | Hayes et al. |
| 8,318,708 B2 | 11/2012 | Evans et al. |
| 2005/0009793 A1 | 1/2005 | Curd |
| 2005/0124591 A1 | 6/2005 | Tian et al. |
| 2005/0148557 A1 | 6/2005 | Tian et al. |
| 2006/0074109 A1 | 4/2006 | Polvino et al. |
| 2006/0135610 A1 | 6/2006 | Bortz et al. |
| 2006/0178351 A1 | 8/2006 | Curd et al. |
| 2006/0240150 A1 | 10/2006 | Delaney et al. |
| 2007/0197517 A1 | 8/2007 | Jani et al. |
| 2007/0275934 A1 | 11/2007 | Curd |
| 2009/0209500 A1 | 8/2009 | Evans et al. |
| 2010/0099640 A1 | 4/2010 | Geuns et al. |
| 2011/0014126 A1 | 1/2011 | Evans et al. |

FOREIGN PATENT DOCUMENTS

| CN | 102 342 914 A | 2/2012 |
| JP | 2013-56834 A | 3/2013 |
| WO | WO 2008/024485 A2 | 2/2008 |
| WO | WO 2008/057363 A2 | 5/2008 |
| WO | WO 2009/061961 A1 | 5/2009 |
| WO | WO 2010/143986 A1 | 12/2010 |
| WO | WO 2011/143209 A1 | 11/2011 |
| WO | WO 2012/127037 A2 | 9/2012 |

OTHER PUBLICATIONS

Mahadevan et al. Tumor-stroma interactions in pancreatic ductal adenocarcinoma. Mol Cancer Ther 2007;6(4):1186-97.*
Demetter et al., "Molecular Changes in Pancreatic Cancer: Implications for Molecular Targeting Therapy," *Acta Gastro-Enterological Belgica* 75:210-214, 2012.
Li et al., "Mannose 6-Phosphate-Modified Bovine Serum Albumin Nanoparticles for Controlled and Targeted Delivery of Sodium Ferulate for Treatment of Heptatic Fibrosis," *J Pharm Pharmacol.* 61:1155-1161, 2009.
Zhang et al., "Interactions of Nanomaterials and Biological Systems: Implications to Personalized Nanomedicine," Adv Drug Deliv. 64:1363-1384, 2012.
EP14787709.6 Communication Pursuant to Rule 164(1) EPC dated Sep. 13, 2016 with Supplementary Partial European Search Report dated Aug. 19, 2016 (9 pages).
Milczarek et al., "Vitamin D Analogs Enhance the Anticancer Activity of 5-Fluorouracil in an in vivo Mouse Colon Cancer Model," *BMC Cancer* 13:294 (2013).
EP14806812.5 Rule 164(1) EPC Communication dated Nov. 3, 2016 with Supplementary Partial European Search Report dated Oct. 25, 2016 (11 pages).
Abramovitch et al., "Vitamin D inhibits proliferation and profibrotic marker expression in hepatic stellate cells and decreases thioacetamide-induced liver fibrosis in rats," *Gut*, 60:1728-1737, 2011.

(Continued)

*Primary Examiner* — Yih-Horng Shiao
(74) *Attorney, Agent, or Firm* — Klarquist Sparkman, LLP

(57) ABSTRACT

Provided herein are methods of treating and preventing pancreatitis, such as pancreatitis induced by glucagon-like peptide (GLP) agonists (such as GLP-1 agonists, for example Byetta®), by administration of a vitamin D receptor agonist (such as vitamin D, vitamin D analogs, vitamin D precursors, and vitamin D receptor agonists precursors). In some examples the subject has diabetes, such as type 2 diabetes.

8 Claims, 29 Drawing Sheets

(56) References Cited

OTHER PUBLICATIONS

Cao et al., "Leptin Stimulates Tissue Inhibitor of Metalloproteinase-1 in Human Hepatic Stellate Cells," *J. Biol. Chem.*, vol. 279, pp. 4292-4304, 2004.
Cohen-Lahav et al., "The Anti-Inflammatory Activity of 1,25-Dihydroxyvitamin D3 in Macrophages," *J. Steroid. Biochem. Mol. Biol.*, vol. 103, pp. 558-562, 2007.
Dai et al., "PPAR gamma is an important transcription factor in 1 alpha, 25-dihydroxyvitaim D3-induced involucrin expression," *J. Derm. Sci*, vol. 51, No. 1, pp. 53-60, Apr. 2008. (Abstract).
Ding et al., "A vitamin D receptor/SMAD genomic circuit gates hepatic fibrotic response," *Cell*, vol. 153, No. 3, pp. 601-613, Apr. 25, 2013.
Dunlop et al., "The human peroxisome proliferator-activated receptor δ gene is a primary target of 1α,25-dihydroxyvitamin $D_3$ and it nuclear receptor," *J. Mol. Biol.*, vol. 349, No. 2, pp. 248-260, Jun. 2005.
Fearon, "The Carcinoma-Associated Fibroblast Expressing Fibroblast Activation Protein and Escape from Immune Surveillance," *Cancer Immunol Res.* 2:187-193, 2014.
Feig et al., "Targeting CXCL12 from FAP-Expressing Carcinoma-Associated Fibroblasts Synergizes with Anti-PD-L1 Immunotherapy in Pancreatic Cancer," *Proc Natl Acad Sci. USA* 110:20212-20217, 2013.
Gascon-Barré et al., "The Normal Liver Harbors the Vitamin D Nuclear Receptor in Nonparenchymal and Biliary Epithelial Cells," *Hepatology*, 37:1034-1042, 2003.
International Search Report and Written Opinion of the International Searching Authority issued by Australian Patent Office dated Sep. 5, 2014 for PCT/US2014/041063.
International Search Report and Written Opinion of the International Searching Authority issued by Australian Patent Office dated Sep. 17, 2014 for PCT/US2014/035235.
Johnson et al., "The Activated Mesangial Cell: A Glomerular 'Myofibroblast'?," *J. Am. Soc. Nephrol.*, vol. 2, pp. S190-S197, 1992.
Johnson et al., "The Antitumor Efficacy of Calcitriol: Preclinical Studies," *Anticancer Res.* 26:2543-2500, 2006.

Jonas et al., "Measurement of Parenchymal Function and Bile Duct Flow in Primary Sclerosing Cholangitis Using Dynamic $^{99m}$Tc-HIDA SPECT," *J. Gastroenterol. Hepatol.* vol. 21, pp. 674-681, 2006.
Klöppel et al., "Fibrosis of the pancreas: the initial tissue damage and the resulting pattern," *Virchows Arch*, vol. 445, pp. 1-8, May 2004.
Ma et al., "1.25$D_3$ enhances antitumor activity of gemcitabine and cisplatin in human bladder cancel models," *Cancer*, 116:3294-3303, Jul. 1, 2010.
Omary et al., "The Pancreatic Stellate Cell: A Star on the Rise in Pancreatic Diseases," *J. Clin. Invest.* vol. 117, pp. 50-59, 2007.
Petta et al., "Low Vitamin D Serum Level Is Related to Severe Fibrosis and Low Responsiveness to Interferon-Based Therapy in Genotype 1 Chronic Hepatitis C," *Hepatology*, vol. 51, pp. 1158-1167, 2010.
Samer et al., "Rat Primary and Immortalized Human Hepatocytes Express an Inducible and Functional Vitamin D Receptor," Abstract, Hepatology & Luminal Research Workshop & Clinical Update on Noninvasive Markers of Liver Injury and Early Diagnosis of Liver Disease, 1-3, Yarra Valley, Victoria, Australia, May 2009.
Suda et al., "Pancreatic fibrosis in patients with chronic alcohol abuse: correlation with alcoholic pancreatitis," *Am J Gastroenterol*, 89:2060-2062, Nov. 1994. (Abstract).
Tan et al., "Paricalcitol Attenuates Renal Interstitial Fibrosis in Obstructive Nephropathy," *J. Am. Soc. Nephrol*, vol. 17, pp. 3382-3393, 2006.
Tan et al., "Therapeutic Role and Potential Mechanisms of Active Vitamin D in Renal Interstitial Fibrosis," *J. Steroid. Biochem. Mol. Biol.*, 103:491-496, 2007.
Wehr et al., "Analysis of the Human Pancreatic Stellate Cell Secreted Proteome," *Pancreas* 40:557-566, 2011.
Whitcomb, "Genetic aspects of pancreatitis," *Annual Review of Medicine*, vol. 61, pp. 413-424, Palo Alto, 2010. (Abstract).
Zehnder et al., "Expression of 25-Hydroxyvitamin D3-1alpha-hydroxylase in the Human Kidney," *J. Am. Soc. Nephrol.*, vol. 10, pp. 2465-2473, 1999.
Zollner et al., "Role of Nuclear Receptors in the Adaptive Response to Bile Acids and Cholestasis: Pathogenetic and Therapeutic Considerations," *Mol. Pharm.*, vol. 3, pp. 231-251, 2006.

\* cited by examiner

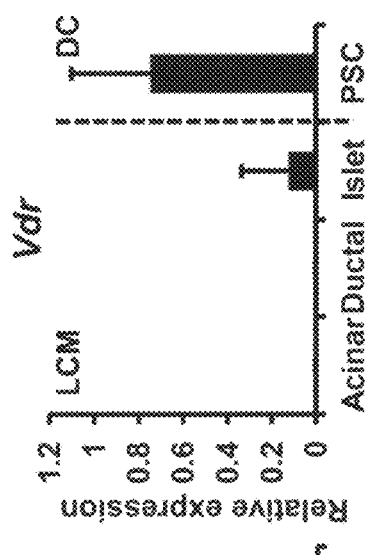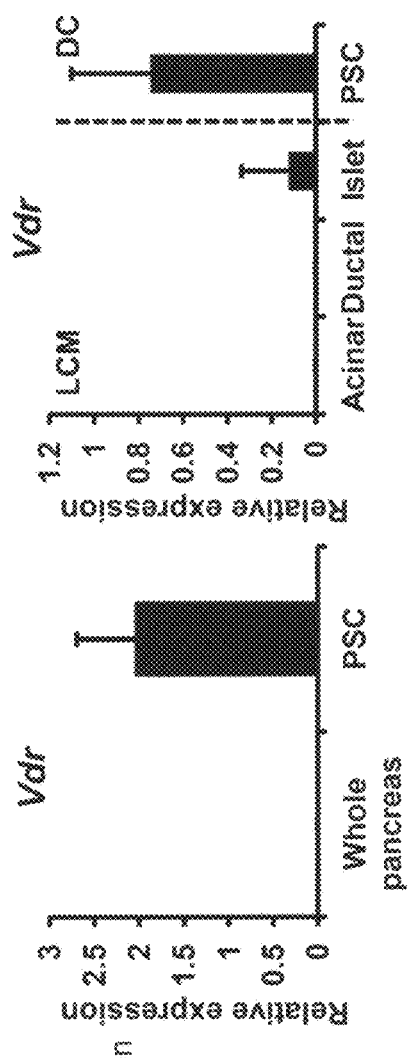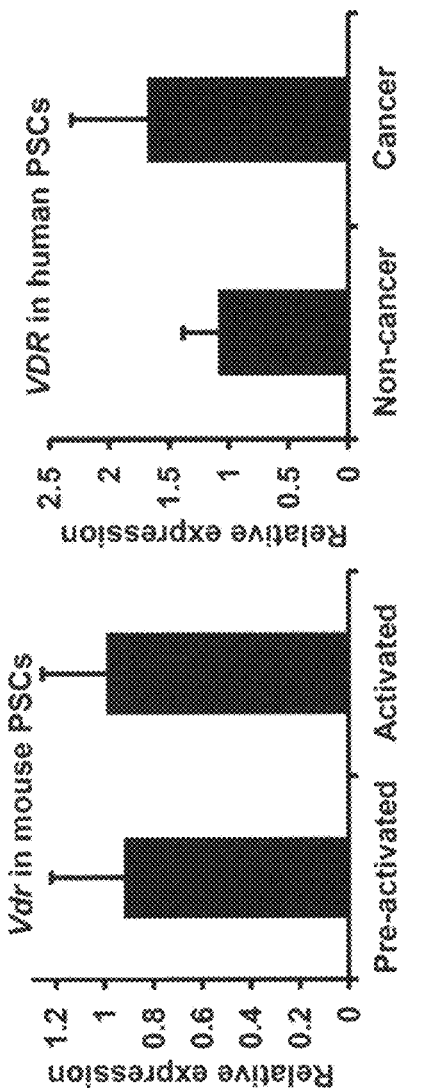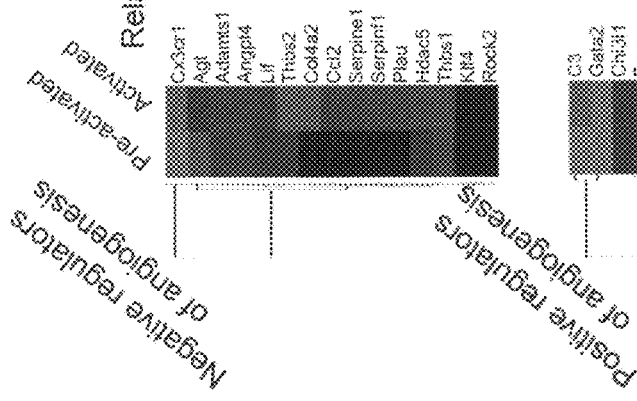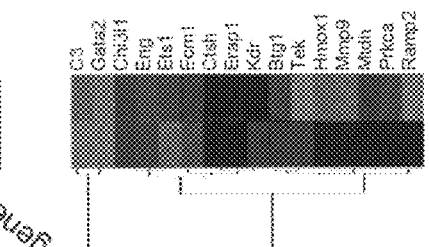

FIG. 2A
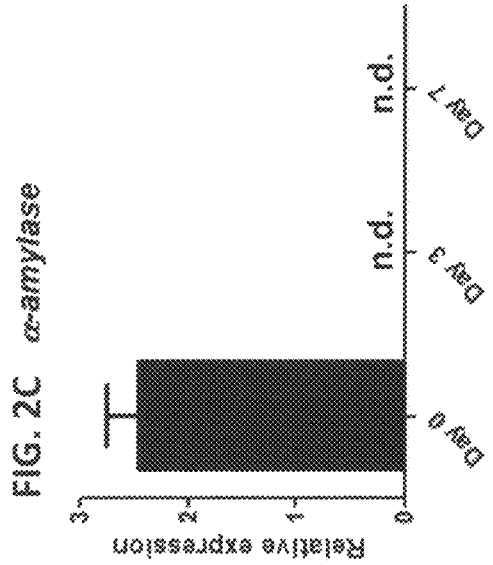
FIG. 2B
Acta2
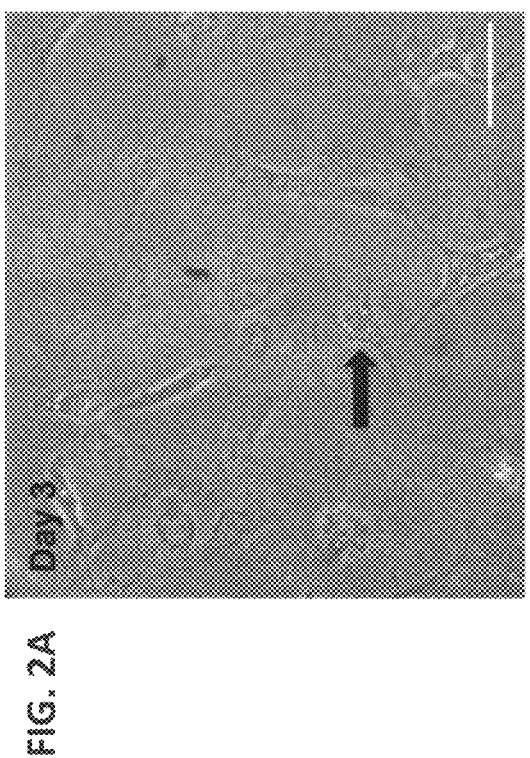
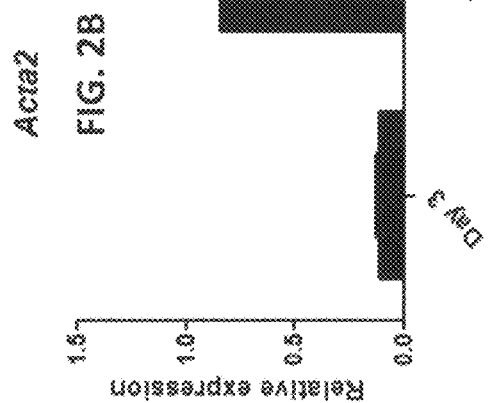
FIG. 2C α-amylase

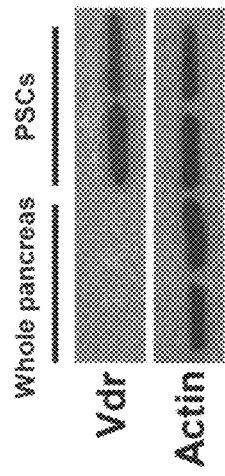
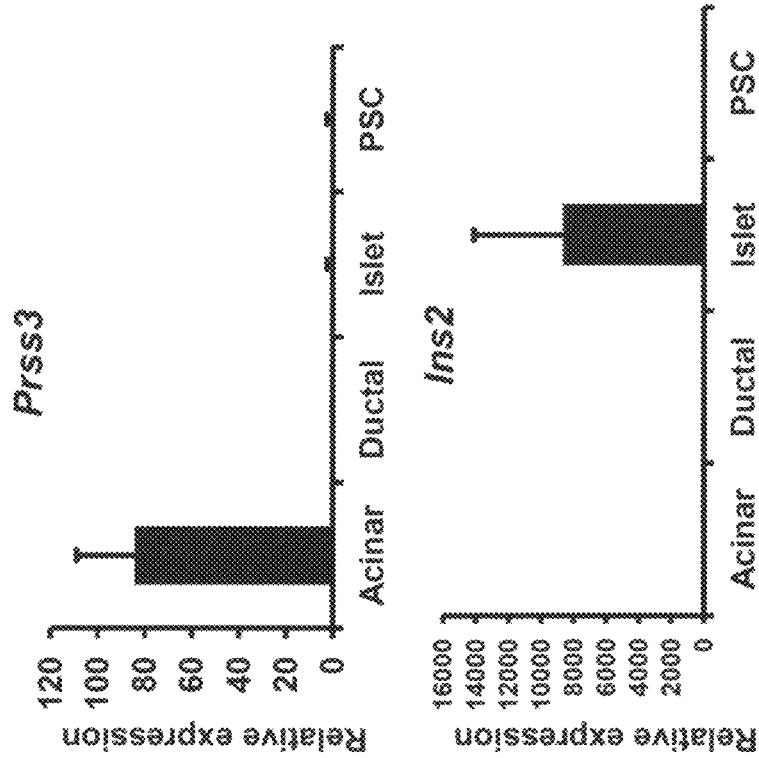
FIG. 2D
FIG. 2E

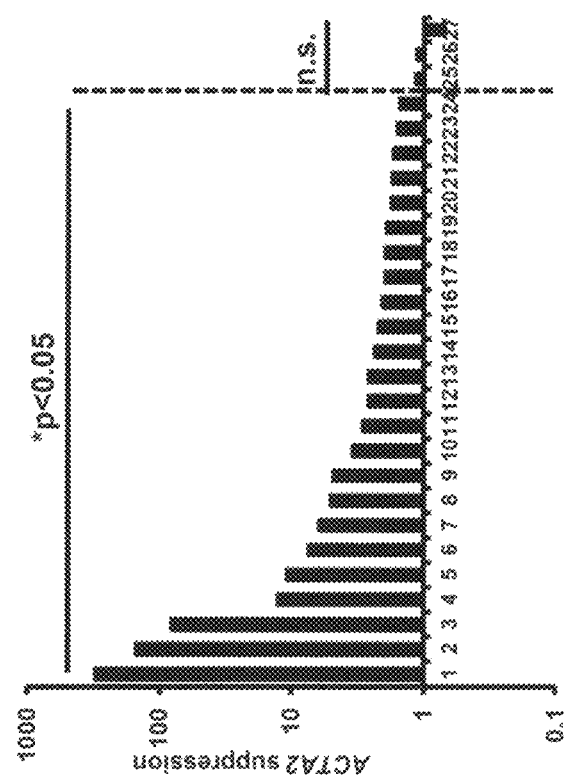
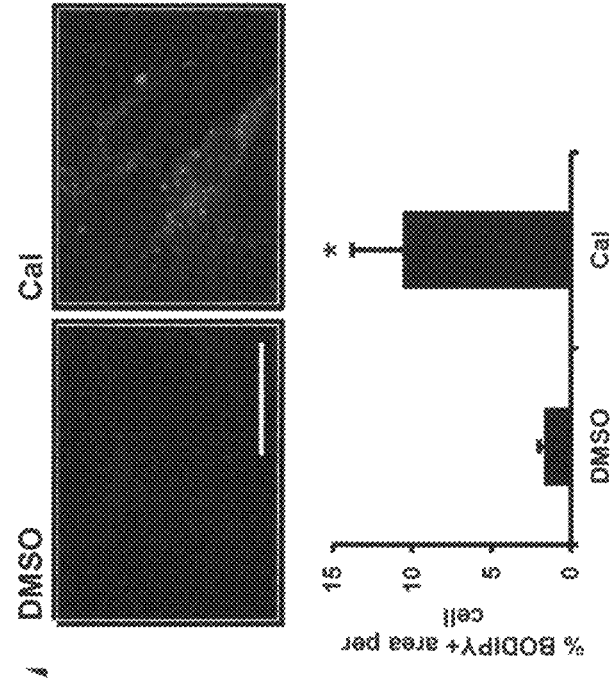
FIG. 3A
FIG. 3B

FIG. 4A
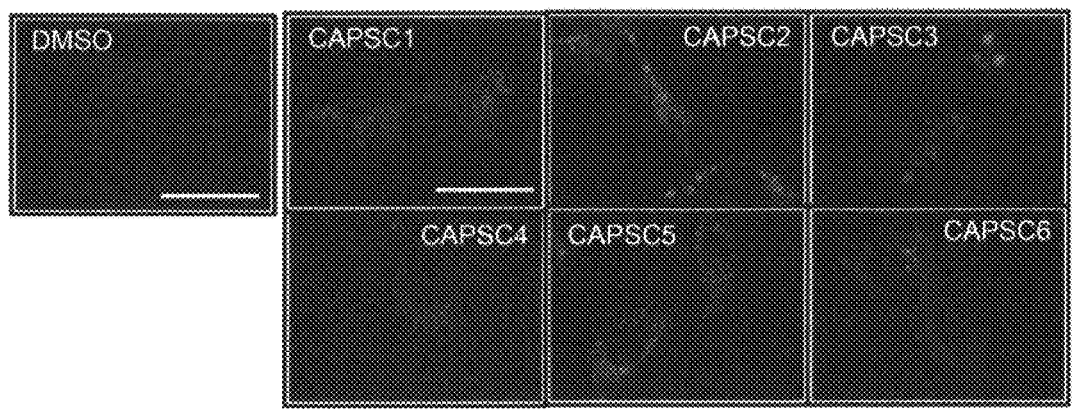
FIG. 4B  HAS2
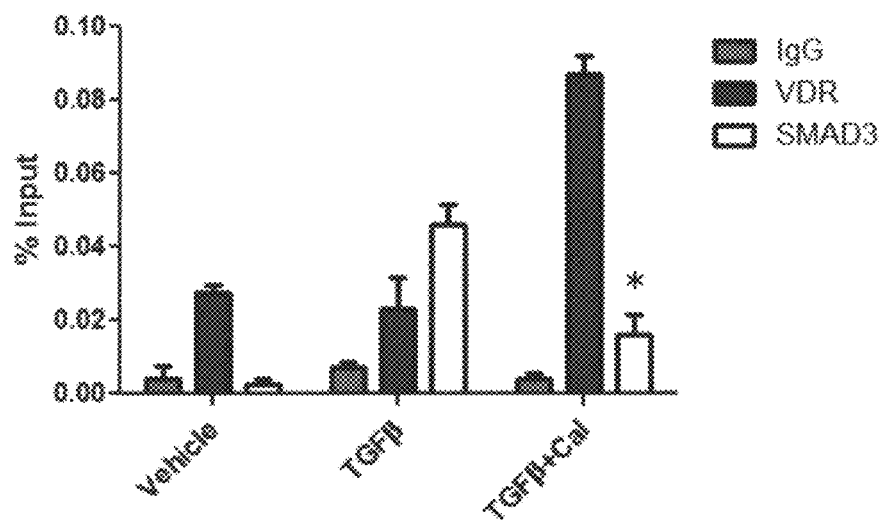
FIG. 4C  COL1A1
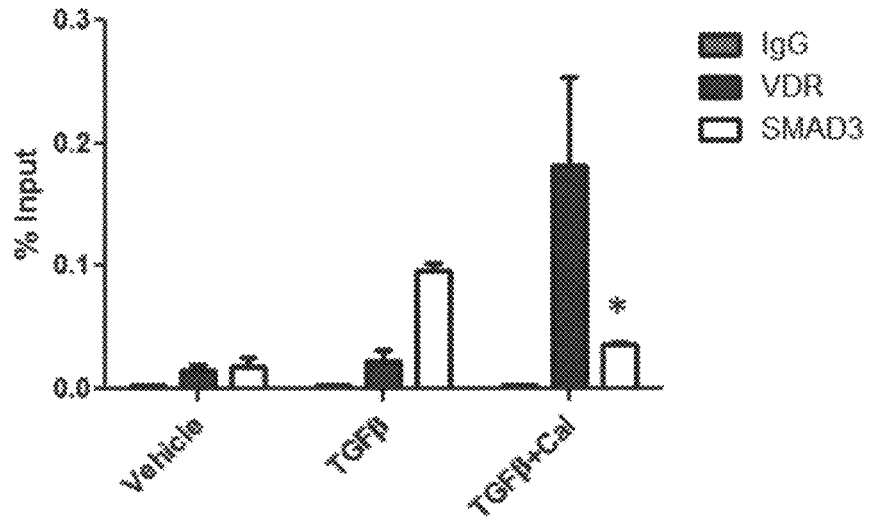

FIG. 5A
H&E
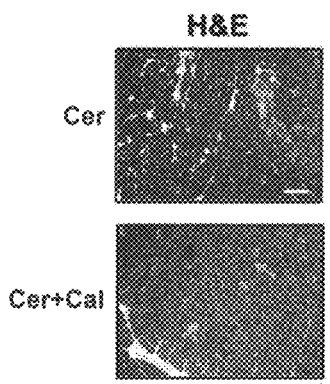
Cer
Cer+Cal
FIG. 5B
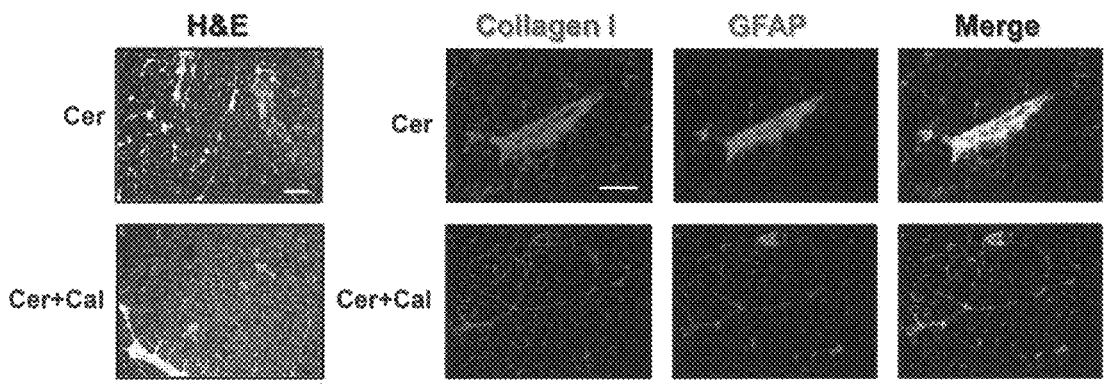
Collagen I  GFAP  Merge
Cer
Cer+Cal
FIG. 5C
Sirius red:
Wild-type
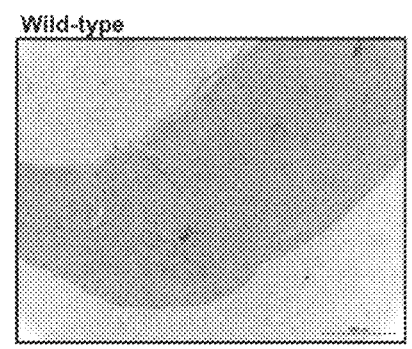
Wild-type
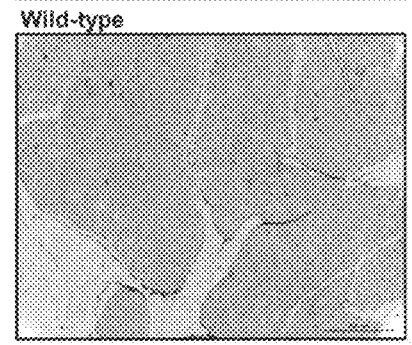
Vdr⁻/⁻
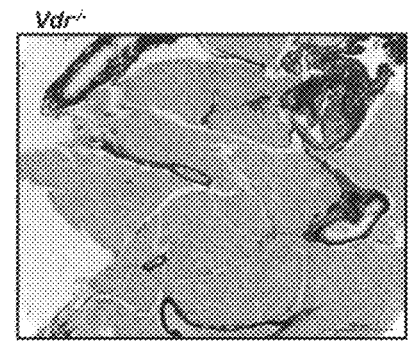
Vdr⁻/⁻
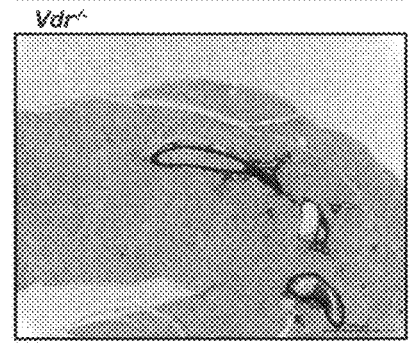

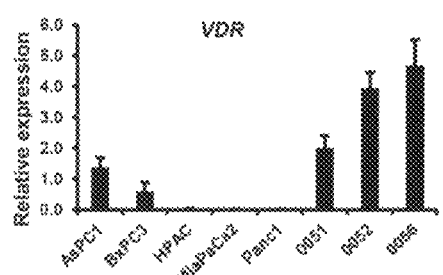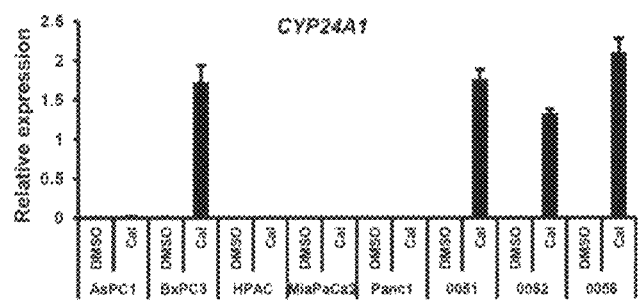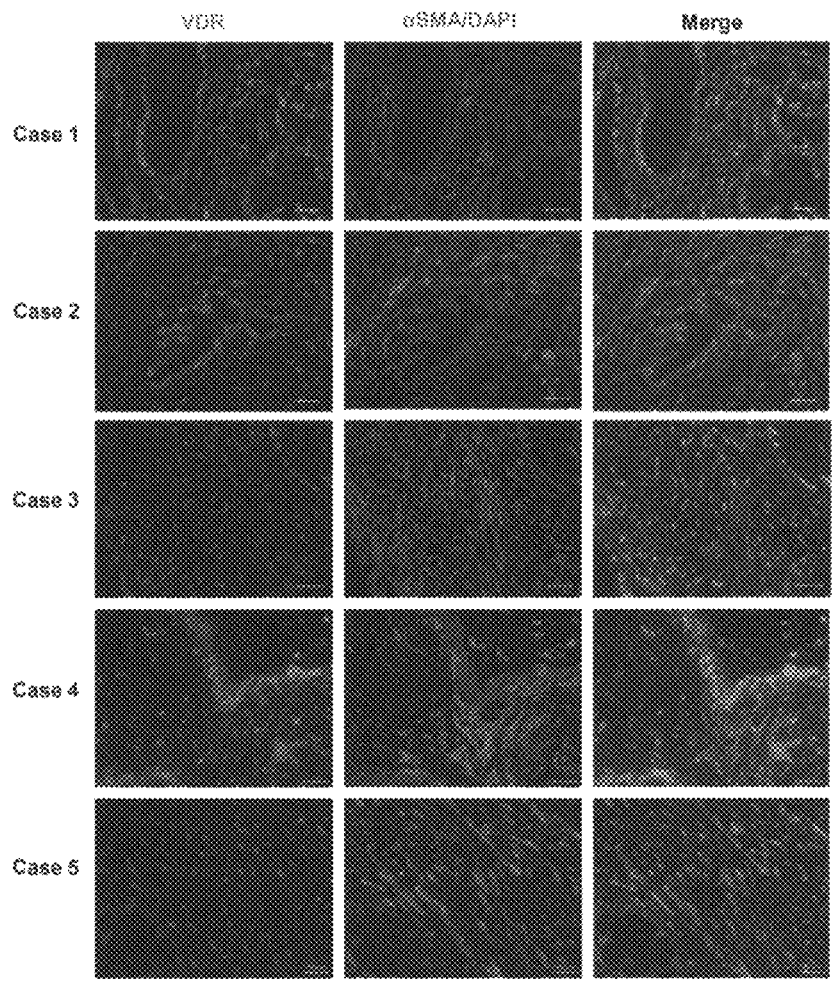

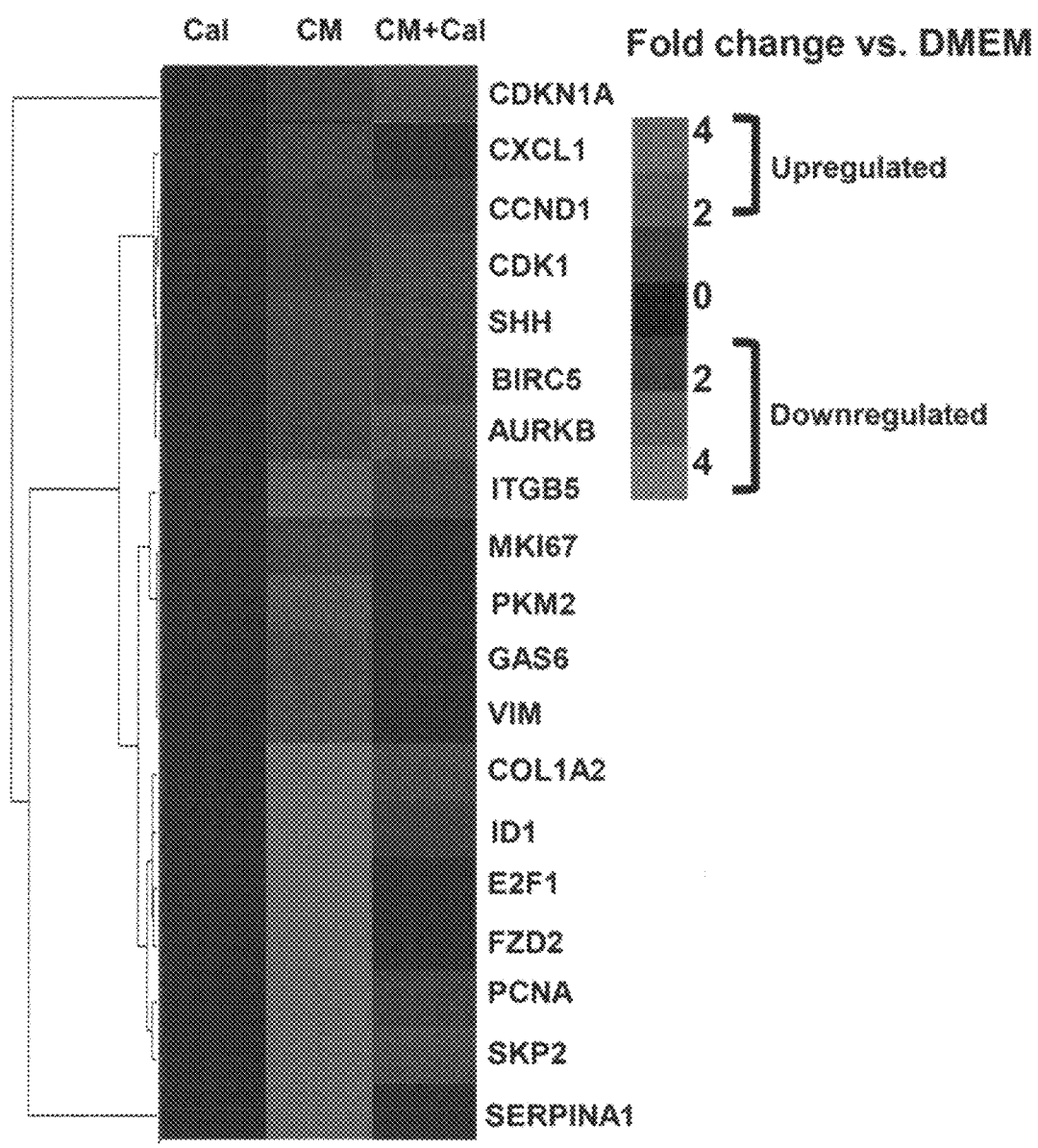

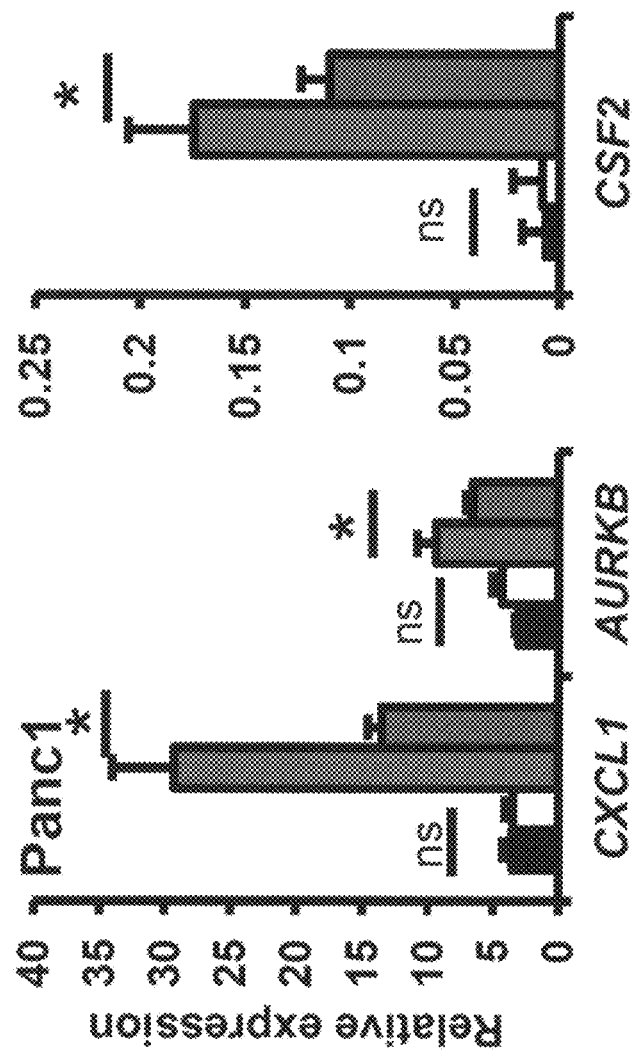
FIG. 8F
FIG. 8G
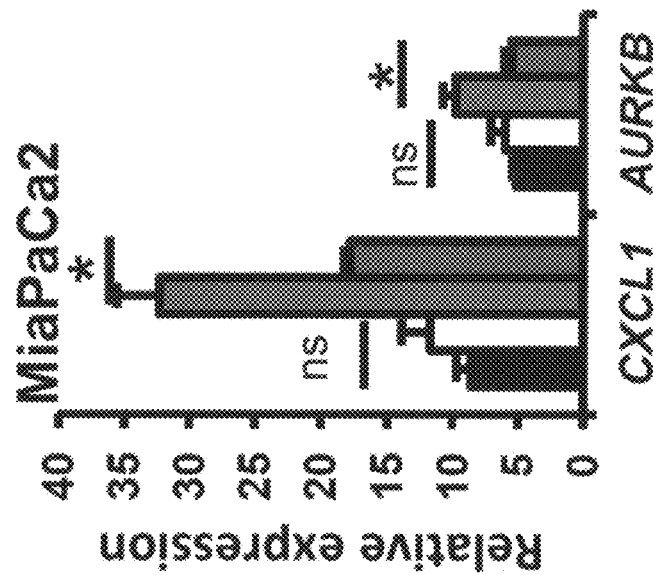

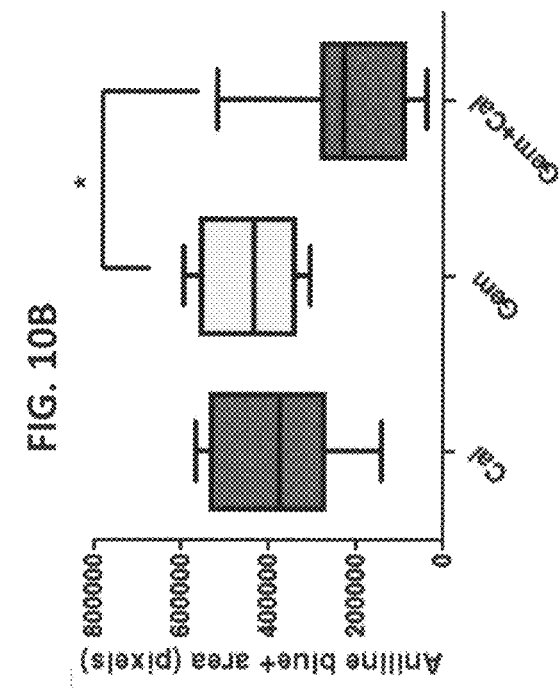
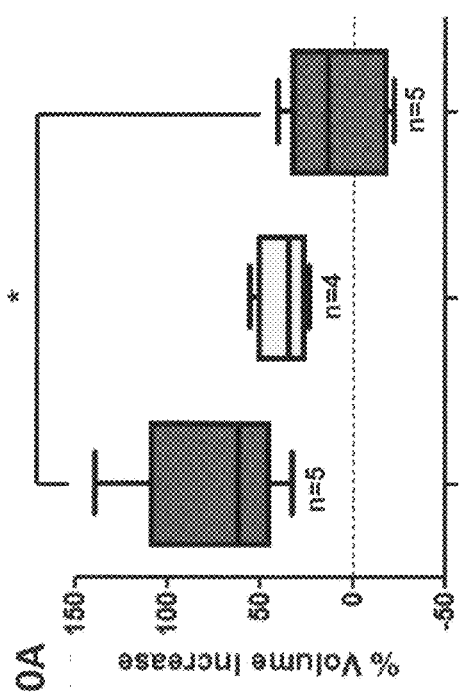
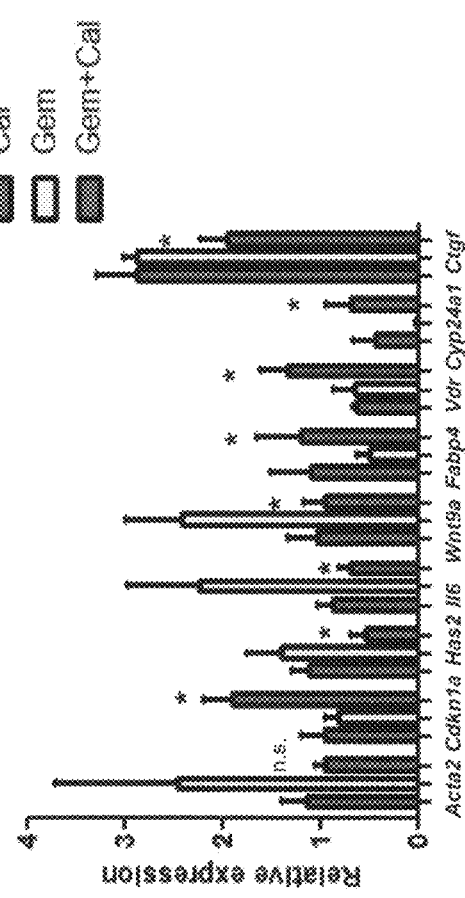
FIG. 10A
FIG. 10B
FIG. 10C

FIG. 12C
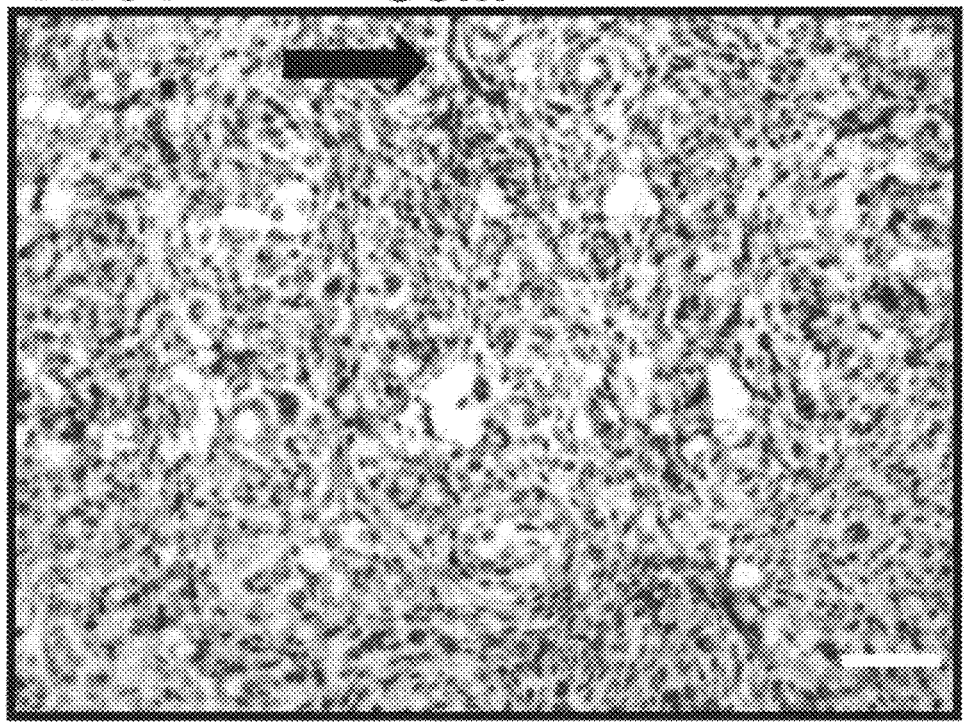
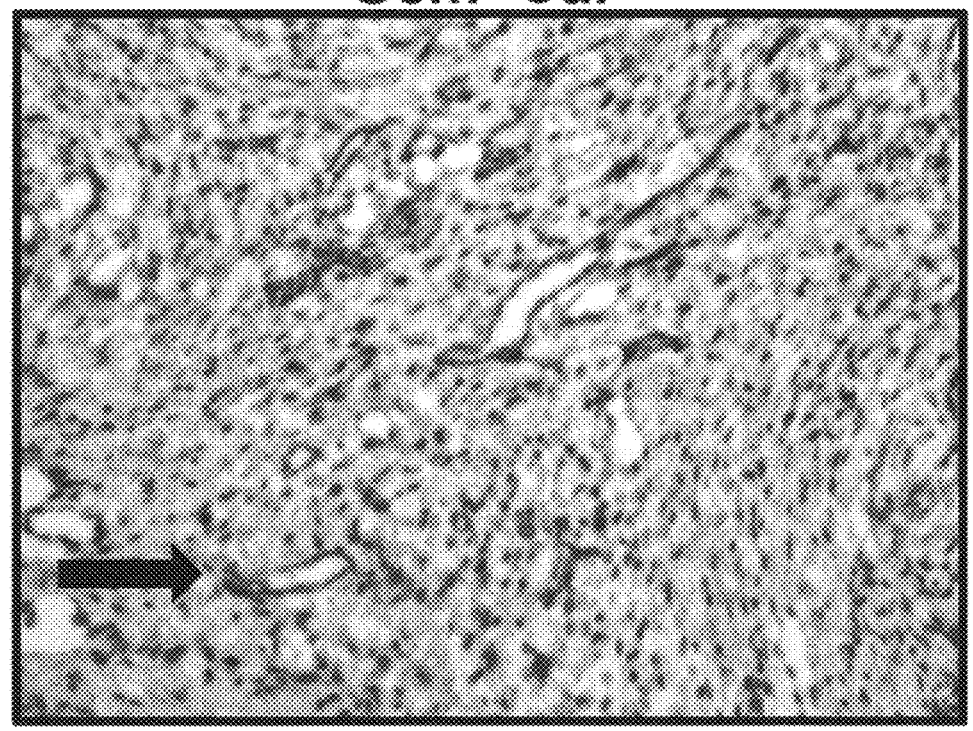

SEQUENCE LISTING

```
<160> NUMBER OF SEQ ID NOS: 106

<210> SEQ ID NO 1
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 1
gtgctgatgg gcaagaac                                                 18

<210> SEQ ID NO 2
<211> LENGTH: 20
<212> TYPE: DNA
<213> ORGANISM: Artificial Sequence
```

```
<220> FEATURE:
<223> OTHER INFORMATION: Synthetic oligonucleotide

<400> SEQUENCE: 2
gctgaacctc catgaggaag                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
cccaatgagt aggctggaga                                              20

<210> SEQ ID NO 4
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 4
acgcatggcc aagaagac                                                18

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
cagaatgagg ctcagcacag                                              20

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 6
ttctctggga aatcgtggaa a                                            21

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
gctgctgctg ctactcctga                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
cgagtggact tccacaacaa                                              20
```

```
<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
gatgtcgccc ctaaaacaga                                                 20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
ttgggaatac ccttggaaga                                                 20

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
gcaagctgag gtcgatcatt                                                 20

<210> SEQ ID NO 12
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 12
atcttctcct ccgcctggt                                                  19

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
tgacaggatg cagaaggaga                                                 20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
tctgtcccct accaggtgtc                                                 20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide
```

<400> SEQUENCE: 15
tttgtcaagc agcacctttg                                        20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
accctcccga gattacaacc                                        20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
actaccagct gtggggtgag                                        20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
cggaggacga gtctatgagc                                        20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
ccagcggcta gagatcaaac                                        20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
ccgtgcttct cagaacatca                                        20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
ctggccagat gttttctggt                                        20

<210> SEQ ID NO 22

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
tgtctggaga aacagccaag                                                     20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
atcggggaac ctctgatttt                                                     20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
cgagtgacaa gcctgtagcc                                                     20

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
ggtctttctg gtgcttgtct                                                     20

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 26
cgagctctac gaggaggaga                                                     20

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
gactcgggac ccatctatga                                                     20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
```
agagtggagc gcctgttcta                                                    20

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
cctgcaaatg ccaacagtta                                                    20

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
gatggtgaca agctggtggt                                                    20

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 31
tcagcctact gccctacag                                                     20

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 32
gacaaacacg aaagcctggt                                                    20

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
catctgtttg aatggcgatg                                                    20

<210> SEQ ID NO 34
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 34
aggtcctcct tggtgaac                                                      18

<210> SEQ ID NO 35
<211> LENGTH: 20
<212> TYPE: DNA

<213> ORGANISM: Artificial Sequence
<220> FEATURE:
<223> OTHER INFORMATION: Synthetic oligonucleotide

<400> SEQUENCE: 35
ggatcatctt ggcgtagagc                                                    20

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 36
tctggaccca ttccttcttg                                                    20

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 37
ggtttccacg tctcaccatt                                                    20

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38
ttgtgtaatg ggcttccaga                                                    20

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39
tgcaagtgca tcatcgttgt                                                    20

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 40
gctcccagag ccctatgta                                                     20

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41
gcaagtggtt tccactccag                                                    20

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 42
gggcagccat agaaagtgtt                                              20

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 43
catgttcacc ccagatacca                                              20

<210> SEQ ID NO 44
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 44
tggctcaaag tatggtttcg t                                            21

<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 45
tggttctccc aggtgactgt                                              20

<210> SEQ ID NO 46
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 46
ccaccgatcc agacagagta                                              20

<210> SEQ ID NO 47
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 47
gttggggtgc ttgatgatct                                              20

<210> SEQ ID NO 48
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 48
tctacaatgc cacgcttctg                                              20

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 49
ggcgagcatt gtcaatctgt                                              20

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 50
ggacatcacc aggattggac                                              20

<210> SEQ ID NO 51
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 51
ctgtgattcc gaggaggaga                                              20

<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 52
cacgggcttc atgagtttct                                              20

<210> SEQ ID NO 53
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 53
cttgccccat tcatttgtct                                              20

<210> SEQ ID NO 54
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 54
ctcggctacg ttgggaataa                                              20

```
<210> SEQ ID NO 55
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 55
tcctcgaata gctgcaagtg                                               20

<210> SEQ ID NO 56
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 56
ggcttggaag cagcagtaac                                               20

<210> SEQ ID NO 57
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 57
agctgctcct ccacttggt                                                19

<210> SEQ ID NO 58
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 58
tatgttcggc ttcccattct                                               20

<210> SEQ ID NO 59
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 59
gaaggcagcc aagttgttct                                               20

<210> SEQ ID NO 60
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 60
ggggtttctc tagcccttgt                                               20

<210> SEQ ID NO 61
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 61
gacaggcttg gcgattttag                                              20

<210> SEQ ID NO 62
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 62
tttcttcccg cagatagcac                                              20

<210> SEQ ID NO 63
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 63
aatttccatc caggcctctt                                              20

<210> SEQ ID NO 64
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 64
gagatggcaa tagccctgaa                                              20

<210> SEQ ID NO 65
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 65
tcaagcaatg gcagtacaca                                              20

<210> SEQ ID NO 66
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 66
ttcccaccaa ggtctgaaag                                              20

<210> SEQ ID NO 67
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 67
cgatgctccc agggctgttt                                              20

<210> SEQ ID NO 68
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 68
gaaagcttgc ctcaatcctg                                              20

<210> SEQ ID NO 69
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 69
cagccactac aagcagcact                                              20

<210> SEQ ID NO 70
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 70
gggagagctg aagattgctg                                              20

<210> SEQ ID NO 71
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 71
acataataac cgctgtggtc gcac                                         24

<210> SEQ ID NO 72
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 72
cccctaagcc tcctgctc                                                18

<210> SEQ ID NO 73
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 73
ccaagtggga caagaaccag atca                                         24

<210> SEQ ID NO 74
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 74
```
acagccgctt cacctacagc                                              20

<210> SEQ ID NO 75
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 75 agagggctc ctggtgag                                                 18

<210> SEQ ID NO 76
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 76
tgatcaccat tggctgggaa ggaa                                         24

<210> SEQ ID NO 77
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 77
ttgcgagctg aggccagaca                                              20

<210> SEQ ID NO 78
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 78
tttcctccgc ctggtgggt                                               19

<210> SEQ ID NO 79
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 79
aaagaggcac tggcagaaaa                                              20

<210> SEQ ID NO 80
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 80
gcctccagca tgaaagtctc                                              20

<210> SEQ ID NO 81
<211> LENGTH: 20
<212> TYPE: DNA
<213> ORGANISM: Artificial Sequence

```
<220> FEATURE:
<223> OTHER INFORMATION: Synthetic oligonucleotide

<400> SEQUENCE: 81
acagacaggc tgaggacgac                                                        20

<210> SEQ ID NO 82
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 82
acgtcggaat tggctctg                                                          18

<210> SEQ ID NO 83
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 83
acatggaaaa gccttgatgg                                                        20

<210> SEQ ID NO 84
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 84
acttgcatga ggaggagcat                                                        20

<210> SEQ ID NO 85
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 85
ccagcgataa tacgcctca                                                         19

<210> SEQ ID NO 86
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 86
gggaagaaaa tcatggctga                                                        20

<210> SEQ ID NO 87
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 87
ttcgtcaccc acgtagctgt cttt                                                   24
```

<210> SEQ ID NO 88
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 88
caccagtgag cttcctcctc                                               20

<210> SEQ ID NO 89
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 89
aaggggatga caagcagaaa                                               20

<210> SEQ ID NO 90
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 90
gcaccacaga tccaccttct                                               20

<210> SEQ ID NO 91
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 91
tggcacttac actccagctt caga                                          24

<210> SEQ ID NO 92
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 92
gcatggacag gatctccaac                                               20

<210> SEQ ID NO 93
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 93
gtccagatca ggtgtgtagc caat                                          24

<210> SEQ ID NO 94
<211> LENGTH: 18
<212> TYPE: DNA
<213> ORGANISM: Artificial Sequence
<220> FEATURE:
<223> OTHER INFORMATION: Synthetic oligonucleotide -continued

<400> SEQUENCE: 94
cggtgtgact cgtgcagc                                                     18

<210> SEQ ID NO 95
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 95
gcagttccag gaggaccag                                                    19

<210> SEQ ID NO 96
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 96
gctgccacaa acctccactt tgta                                              24

<210> SEQ ID NO 97
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 97
aaactcctgt gactctgctg atgagg                                            26

<210> SEQ ID NO 98
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 98
gttctccgag gtgactgtcg ataca                                             25

<210> SEQ ID NO 99
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 99
agctctggct tgttcctcac                                                   20

<210> SEQ ID NO 100
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 100
cacttgctgc tggtgattct                                                   20

<210> SEQ ID NO 101

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 101
gctgtgattc caaggaggag                                               20

<210> SEQ ID NO 102
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 102
cagataggag cgggaggag                                                19

<210> SEQ ID NO 103
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 103
gcagcagtct ggaaggtagg                                               20

<210> SEQ ID NO 104
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 104
tcggctagct tctggatcat                                               20

<210> SEQ ID NO 105
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 105
accctgtaga atgccttgga                                               20

<210> SEQ ID NO 106
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 106
cagaaggtgc aataccagca                                               20
```

VITAMIN D RECEPTOR AGONISTS TO TREAT DISEASES INVOLVING CXCL12 ACTIVITY

CROSS-REFERENCE TO RELATED APPLICATIONS

This is a continuation of International Application No. PCT/US2014/041063, filed Jun. 5, 2014, which was published in English under PCT Article 21(2), which in turn claims priority to U.S. Provisional Application No. 61/831,515, filed Jun. 5, 2013, the disclosures of which are incorporated by reference herein in their entirety.

ACKNOWLEDGEMENT OF GOVERNMENT SUPPORT

This invention was made with government support under HL105278, DK0577978, DK090962, CA014195, and ES010337 awarded by The National Institutes of Health and under T32-CA009370 awarded by a National Research Service Award. The government has certain rights in the invention.

This invention was made with government support under T32-CA009370 National Research Service Award, and under HL105278, DK0577978, DK090962, CA014195, and ES010337 awarded by the National Institutes of Health. The government has certain rights in this invention.

FIELD

This application relates to methods of treating or preventing diseases, such as pancreatitis and cancers in which there is activation of juxtaposed stellate cells, by administration of one or more vitamin D receptor (VDR) agonists.

BACKGROUND

Cancer-associated fibroblast-like cells (CAFs) in the tumor stroma have been shown to exert a profound influence on the initiation and progression of carcinoma, the most common form of human cancer (Bhowmick et al., 2004; Kalluri and Zeisberg, 2006; Pietras and Ostman, 2010; Rasanen and Vaheri, 2010; Shimoda et al., 2010). Pancreatic ductal adenocarcinoma (PDA) in particular is defined by a prominent stromal compartment, and numerous features ascribed to CAFs promote pancreatic cancer progression and hinder therapeutic efficacy (Mahadevan and Von Hoff, 2007). CAFs enhance PDA growth in allograft models in part via paracrine activation of pro-survival pathways in tumor cells, and inhibition of tumor-stromal interactions limits tumor progression (Hwang et al., 2008; Ijichi et al., 2011; Vonlaufen et al., 2008). Further, the dense extracellular matrix (ECM) associated with PDA obstructs intratumoral vasculature, preventing chemotherapeutic delivery (Olive et al., 2009), leading to new ideas to overcome this stromal "roadblock" (Jacobetz et al., 2012; Provenzano et al., 2012). Beyond drug delivery, recent evidence implicates the tumor stroma in innate drug resistance in numerous tumor types (Straussman et al., 2012; Wilson et al., 2012), and treatment paradigms targeting both neoplastic cells and stromal components are emerging for PDA (Heinemann et al., 2012). While these findings suggest that CAFs in the PDA microenvironment represent a potential therapeutic target, the tumor-supporting features of pancreatic stellate cells (PSCs), the predominant fibroblastic cell type in the tumor microenvironment of the pancreas, remain poorly understood.

PSCs are nestin-positive and resident lipid-storing cells of the pancreas, with an important role in normal ECM turnover (Apte et al., 1998; Phillips et al., 2003). In health, PSCs are in a quiescent state, characterized by abundant cytoplasmic lipid droplets rich in vitamin A, and low levels of ECM component production (Apte et al., 2012). During pancreatic injury, PSCs are activated by cytokines, growth factors, oxidative or metabolic stress and transdifferentiate to a myofibroblast-like cell (Masamune and Shimosegawa, 2009). Activated PSCs lose their cytoplasmic lipid droplets, express the fibroblast activation marker α-smooth muscle actin (αSMA), acquire proliferative capacity, and synthesize abundant ECM proteins. Activated PSCs also acquire an expansive secretome which is starkly subdued in the quiescent state (Wehr et al., 2011). Persistent PSC activation under conditions of chronic injury results in pathological matrix secretion leading to fibrosis, creating a physical barrier to therapy. Further, a reciprocal supportive role for activated PSCs and pancreatic cancer cells has become increasingly appreciated: pancreatic cancer cells produce mitogenic and fibrogenic factors which promote PSC activation, such as platelet-derived growth factor (PDGF), transforming growth factor β (TGFβ), and sonic hedgehog (SHH) (Apte and Wilson, 2012; Bailey et al., 2008). Reciprocally, activated PSCs produce PDGF, insulin-like growth factor 1 (IGF1), connective tissue growth factor (CTGF) and other factors which may promote cancer cell proliferation, survival, and migration (Apte and Wilson, 2012; Feig et al., 2012). Tumor-promoting features are largely restricted to the activated PSC state; the activation process may be reversible as suggested by recent work in hepatic stellate cells (Kisseleva et al., 2012). However, the cellular factors and molecular pathways controlling this process remain elusive.

SUMMARY

The inventors proposed that pharmacologic means could be used to revert activated cancer-associated PSCs (CAPSCs) to quiescence to hinder tumor-stroma crosstalk and tumor growth, resulting in enhanced clinical efficacy of cancer cell-directed chemotherapy. RNA-Seq analysis of mouse and human PSCs was performed to determine the PSC activation signature, and to identify therapeutic targets. This analysis revealed high levels of vitamin D receptor (VDR) expression in PSCs in all examined stages of activation. The data provided herein shows that VDR acts as a master genomic regulator of the PSC activation state. In a murine pancreatitis model, VDR ligand reduces fibrosis and inflammation and conversely, Vdr−/− mice spontaneously develop pancreatic fibrosis. Furthermore, VDR ligand simultaneously undermines multiple tumor-supporting signaling pathways in PDA, enhancing the efficacy of a co-administered chemotoxic agent despite negligible effects of VDR ligand as a single-agent. Together these results highlight a widely applicable strategy to influence stroma-associated pathologies including inflammation, fibrosis and cancer.

Based on these observations, methods of reducing the biological activity of C-X-C motif ligand 12 (CXCL12) are provided. For example, such methods can include contacting stellate cells (such as those expressing CXCL12) with a therapeutically effective amount of one or more vitamin D receptor (VDR) agonists, thereby reducing the production and secretion of CXCL12. In one example, the VDR agonist is a synthetic agonist, such as one that does not have significant hypercalcemia effects (such as paricalcitol or calcipotriol). In some examples, the VDR agonist reduces one or more of CXCL12 nucleic acid expression, CXCL12 protein expression, CXCL12 secretion (e.g., by stellate cells), CXCL12 binding to tumor cells, and CXCL12 preventing T-cell binding to tumor cells. Such methods can be performed in vitro or in vivo.

In one example, reducing CXCL12 activity is used to treat a tumor in a subject. For example, a subject can be administered a therapy that includes both a therapeutically effective amount of one or more VDR agonists and a therapeutically effective amount of one or more chemotherapeutic or biological agents. The therapeutic agents need not be administered at the same time. For example, the agents can be administered sequentially. In one example, the VDR agonist is administered prior to administering the therapeutically effective amount of the chemotherapeutic or biological agents.

Thus, the disclosure provides methods for treating a cancer, such as a cancer of the pancreas, liver, kidney, lung, bile duct, or prostate. Such methods can include administering to a mammalian subject having the cancer a therapeutically effective amount of one or more VDR agonists and administering to the mammalian subject a therapeutically effective amount of a chemotherapy or biotherapy for the cancer (e.g., fluorouracil, gemcitabine, erlotinib, protein-bound paclitaxel, or combinations thereof, for a pancreatic ducal adenocarcinoma).

In one example, reducing CXCL12 production and secretion is used to treat or prevent pancreatitis. For example, a subject having, or at risk to develop pancreatitis, can be administered a therapy that includes both a therapeutically effective amount of one or more VDR agonists. In one example, the subject is one who takes/receives or has previously taken a glucagon-like peptide (GLP) agonist, such as a GLP-1 agonist. Thus, in some examples the subject to be treated has diabetes, such as type 2 diabetes. Examples of GLP agonists include but are not limited to: exenatide, taspoglutide, insulin glargine, pioglitazone, albiglutide, lixisenatide, saxagliptin, liraglutide, linagliptin, alogliptin, sitagliptin and metformin/sitagliptin.

Thus, the disclosure provides methods for treating or preventing pancreatitis, such as pancreatitis that results from GLP-1 agonist therapy. Such methods can include administering to a mammalian subject having or at risk to develop pancreatitis a therapeutically effective amount of one or more VDR agonists. In one example, the subject is one who takes/receives or has previously taken/received a GLP agonist, such as a GLP-1 agonist. Thus, in some examples the subject to be treated has diabetes, such as type 2 diabetes.

The foregoing and other objects and features of the disclosure will become more apparent from the following detailed description, which proceeds with reference to the accompanying figures.

BRIEF DESCRIPTION OF THE DRAWINGS

FIGS. 1A-1F. Activated and cancer-associated PSCs exhibit a pro-fibrotic, pro-inflammatory phenotype. (A) Heatmap representing selected genes from RNA-Seq analysis of primary mouse PSCs, demonstrating gene categories with altered expression during activation. Data are represented as $\log_2$ fold change, activated (day 7) vs. pre-activated (day 3), n=3 per group. (B) Heatmap representing selected genes from RNA-Seq analysis of primary human PSCs, isolated from PDA patients (n=5) or cancer-free donors (n=4) and cultured for 15 days to achieve adequate yield and purity, expressed as $\log_2$ fold change PDA vs. cancer-free. (C) Heatmap showing the relative abundance of negative (top) and positive (bottom) regulators of angiogenesis in pre-activated and activated primary mouse PSCs. (D) Vdr expression in mouse whole-pancreas homogenates and in isolated PSCs, cultured for 3 days to expand and purify, as measured by qRT-PCR. (E) Vdr expression in the indicated pancreatic populations by qRT-PCR (normalized to 36B4; n=5). Acini, ducts, and islets were isolated by laser capture microdissection (LCM); PSCs were isolated by density centrifugation (DC). (F) Vdr expression in pre-activated and activated mouse PSCs (left) and in human non-cancer associated and cancer-associated PSCs (right) determined by qRT-PCR (normalized to 36b4, n=3). Bars indicate the mean; error bars indicate SD.

FIGS. 2A-2E. Primary mouse PSCs transdifferentiate to an activated phenotype between days 3 and 7 of culture, related to FIG. 1. PSCs were isolated from pancreata of wild-type C57BL6/J mice at 8 weeks of age and cultured for 7 days (see Supplemental Experimental Procedures). (A) Brightfield microscopy displays cytoplasmic lipid droplets (indicated by arrow) in pre-activated PSCs on day 3 of culture, which give rise to myofibroblast-like activated PSCs by culture day 7. Scale bar=50 μm. (B) RNA was harvested on days 3 and 7 and quantitative RT-PCR (qRT-PCR) performed for fibroblast activation marker Acta2. (C) RNA was harvested immediately after PSC isolation (day 0), and on days 3 and 7 of culture. Quantitative RT-PCR was performed for α-amylase to determine the degree of acinar cell contamination, which was no longer detectable after 3 days of culture. (D) Whole-cell lysates were prepared and analyzed by Western blot to determine protein levels of Vdr in whole mouse pancreas and in isolated PSCs. Actin was a loading control. Lysates from 2 representative mice are shown here. (E) Purity of the isolated pancreatic populations assessed by relative expression of cell-type specific genes determined by qRT-PCR. Data normalized to 36b4. Bars indicate mean+SD.

FIGS. 3A-3F. A VDR-regulated transcriptional network opposes PSC activation. (A) Representative images of primary human CAPSCs treated with vehicle (DMSO) or 100 nM calcipotriol (Cal) for 48 h and stained with BODIPY 493/503 for detection of neutral lipids. Quantification of percent BODIPY-positive area per cell in 3 patient samples treated with DMSO or Cal appears below, plotted as the mean+SD. Statistical significance determined by Student's unpaired t-test (*$p<0.05$). Scale bar=20 μm. (B) Expression of ACTA2 in 27 primary human CAPSCs treated with vehicle or 100 nM Cal for 48 h. Values were plotted as DMSO/Cal and normalized to 36B4. (C) Heatmap representing selected genes from RNA-Seq analysis of preactivated (cultured for 3 days after harvest) or activated (cultured for 7 days after harvest) primary mouse PSCs treated with DMSO (D) or Cal (C) (n=3). VDR target genes Cyp24α1 and Vdr are shown as controls. Related to Table 3. (D) Heatmap showing the relative abundance of negative (top) and positive (bottom) regulators of angiogenesis in activated primary mouse PSCs cultured in the presence of vehicle (DMSO) or Cal. (E) Expression levels of selected genes from the PSC activation or cancer signatures in CAPSCs treated with DMSO or 100 nM Cal for 48 h. Results are representative of 3 patient samples and are plotted as the mean+SD. qRT-PCR was performed in technical triplicate and values were normalized to 36B4. Statistical significance determined by Student's unpaired t-test (*$p<0.05$). (F) CAPSCs were transfected with siRNA pools against VDR (siVDR) or a non-targeting control (siNT). Cells were then treated with DMSO or 100 nM Cal for 48 h and analyzed by qRT-PCR. Values were normalized to 36B4. Results are representative of 3 patient samples and are plotted as the mean+SD. Statistical significance determined by Student's unpaired t-test (*p<0.05; n.s.=not significant).

FIGS. 4A-4C. VDR activation antagonizes the TGFβ/SMAD pathway in PSCs, related to FIG. 6. (A) Primary human CAPSCs treated with vehicle (DMSO) or 100 nM calcipotriol (Cal) for 48 h were fixed and stained with BODIPY 493/503 for detection of neutral lipids. Six images (representing 19/27 samples) represent Cal-treated cells and contain cytoplasmic lipid droplets, a hallmark of the quiescent state. (B) The hPSC cell line was acutely activated with 1 ng/ml TGFβ for 4 h, and pretreated with 100 nM calcipotriol (Cal) for 16 h. Cells were fixed and subject to chromatin immunoprecipitation (ChIP) for SMAD3 and VDR, and rabbit IgG as an isotype control. Chromatin immunoprecipitates were analyzed by QPCR to assess binding of VDR and SMAD3 to the promoter regions of the HAS2 and (C) COL1A1 genes. Rabbit IgG served as an isotype control for both antibodies. Bars indicate mean+SD. *p<0.05 by Student's t-test.

FIGS. 5A-5C. VDR activation reduced inflammation and fibrosis during cerulein-induced pancreatitis, related to FIG. 6. For details of chronic (n=10) and acute (n=5) pancreatitis methods, see Example 1. Pancreata were harvested, sliced, and immediately fixed in formalin or embedded in OCT and frozen. (A) H&E staining of FFPE sections from the indicated treatment groups. Scale bar=100 μm. (B) Co-immunofluorescence for Collagen I and PSC marker GFAP on frozen sections from the indicated treatment groups. Scale bar=100 μm. (C) Pancreata from wild-type and Vdr$^{-/-}$ littermates at 6 months of age were harvested and collagen was stained with Sirius Red. Two representative samples are shown per genotype (n=8). Scale bar=500 μm.

FIGS. 7A-7C. VDR is consistently expressed and ligand-responsive in PSCs, but expression is variable and transcriptional activity is lower in pancreatic cancer cells, related to FIG. 8. (A) VDR expression was measured by qRT-PCR in the 5 indicated pancreatic cancer cell lines, and in 3 CAPSC samples (0051, 0052, and 0056). (B) The indicated cell lines or samples were incubated with vehicle or Cal (100 nM, 16 h) and expression of VDR target gene CYP24A1 was measured by qRT-PCR. Values were normalized to 36B4. Bars represent mean+SD. (C) Resected sections of human PDA were used for double immunofluorescent staining of VDR and α-SMA (a marker of activated PSCs). Nuclei were counterstained with DAPI. Bar: 40 μm.

FIGS. 8A-8I. Stromal VDR activation decreases pro-tumorigenic paracrine signaling. (A) Volcano plots representing gene expression changes detected by RNA-Seq in MiaPaCa-2 cells treated with 100 nM Cal for 48 h vs. media alone (left), with CAPSC conditioned media (CM) for 48 h vs. media alone (middle), or with CM from Cal-treated CAPSC (100 nM, 48 h) for 48 h vs. media alone. Blue indicates significant change; red indicates no significant change. (B) Heatmap representing selected genes from the RNA-Seq analyses described in (A), plotted as fold change vs. media alone (DMEM). (C-G) The indicated cell lines were incubated with Cal directly, or with CM from CAPSC with or without Cal treatment, as described above. Expression levels of candidate genes CXCL1, CSF2, and AURKB were determined by qRT-PCR. Values were normalized to 36B4; means+SD are shown. Statistical significance determined by Student's unpaired t-test (*p<0.05). Results are shown as replicates with 1 patient sample, and are representative of results from multiple patient samples (n=4), though sample-to-sample variability was noted. (H) Immunoblot for p-STAT3 from MiaPaCa-2 cells treated for 48 h with 100 nM Cal, CAPSC CM, Cal+CAPSC CM, or Cal+CAPSC (Cal-treated) CM. Actin served as a loading control. Values indicate densitometric ratios (p-STAT3/Actin). (I) Viability of MiaPaCa-2 cells, treated as described above, incubated with the indicated doses of gemcitabine for 48 h. Results are representative of 3 CAPSC CM samples and are plotted as the mean±SD. Statistical significance determined by Student's unpaired t-test (*p<0.05). Asterisks designate statistically significant differences in viability between CM and CM (PSC+Cal) samples at the indicated dose of gemcitabine.

FIGS. 10A-10E. Stromal VDR activation shows efficacy against pancreatic carcinoma in vivo when combined with gemcitabine. KPC mice were treated for 9 days with gemcitabine (Gem), calcipotriol (Cal), or Gem+Cal (Gem: n=4; Cal: n=7; Gem+Cal: n=7 unless otherwise indicated). (A) Percent change in tumor volume at study endpoint, measured by high-resolution ultrasound. Plots indicate range, median, and quartiles. *p<0.02; Kruskal-Wallis and Dunn's nonparametric comparison test. (B) Aniline blue-stained collagen fibers were quantified as positive pixels per 200× field. Plots indicate range, median, and quartiles. *p<0.05 by Mann-Whitney U test. (C) Gene expression in tumor homogenates was determined by qRT-PCR. Values were normalized to 36b4. Bars indicate mean+SD. *p<0.05 by Student's unpaired t-test (compared to Gem alone). (D) Intratumoral concentrations of gemcitabine triphosphate (dFdCTP, measured by LC-MS/MS) in Gem– and Gem+Cal-treated mice 2 h after the final dose of gemcitabine (n=4 and 7 respectively). Plots indicate range, median, and quartiles. *p<0.05 by Mann-Whitney U test. (E) IHC for cleaved caspase-3 (CC3) was quantified as % CC3-positive tumor cells per 200× field. Plots indicate range, median, and quartiles. *p<0.05 by Mann-Whitney U test.

FIGS. 12A-12C. VDR ligand enhances delivery and efficacy of gemcitabine. KPC mice were treated for 9 days with gemcitabine (Gem), calcipotriol (Cal), or Gem+Cal (Gem: n=4; Cal: n=7; Gem+Cal: n=7 unless otherwise indicated). (A) Dck and Cdα gene expression in tumor homogenates determined by qRT-PCR. Values were normalized to 36b4. Bars indicate mean+SD. (B) IHC for CD31 was quantified as CD31 (NovaRed)-positive area per 400× field. Plots indicate range, median, and quartiles. *p<0.05 by Mann-Whitney U test. (C) Representative CD31 IHC from Gem– and Gem+Cal-treated KPC tumors. Arrows indicate a collapsed vessel in a gemcitabine-treated tumor (top), and a vessel with an apparent lumen in a Gem+Cal-treated tumor (bottom). Scale bar=50 μm.

SEQUENCE LISTING

Figure 1B:
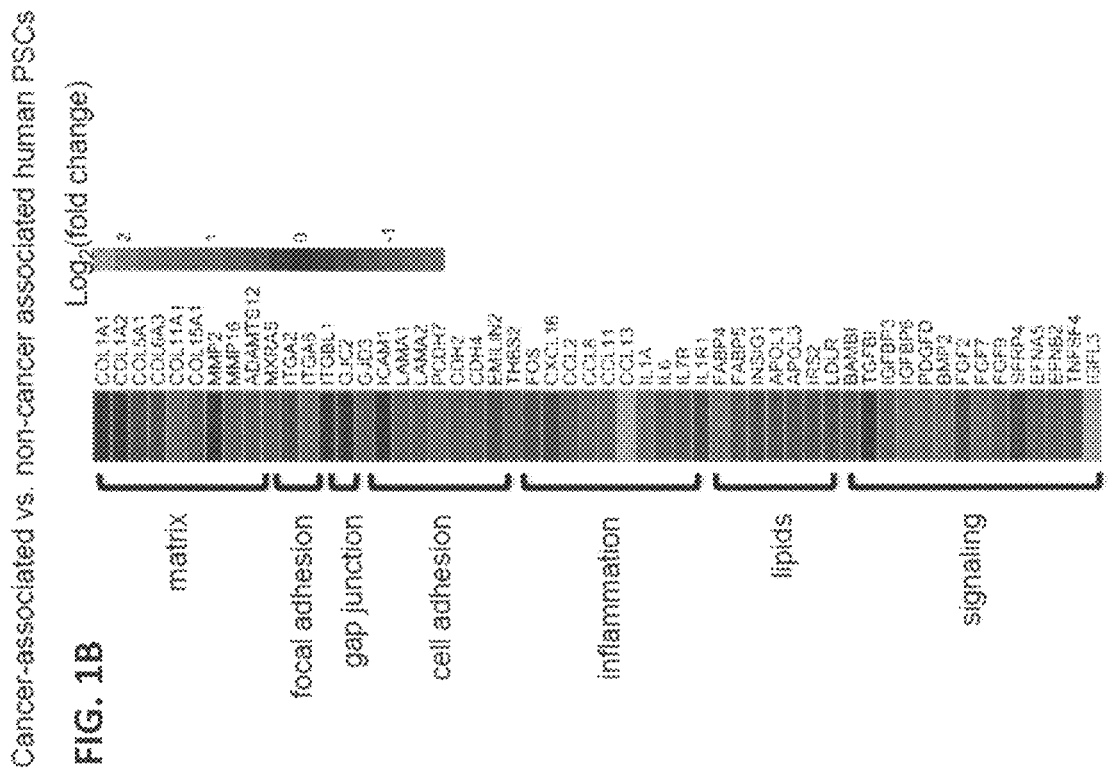
Figure 1A:
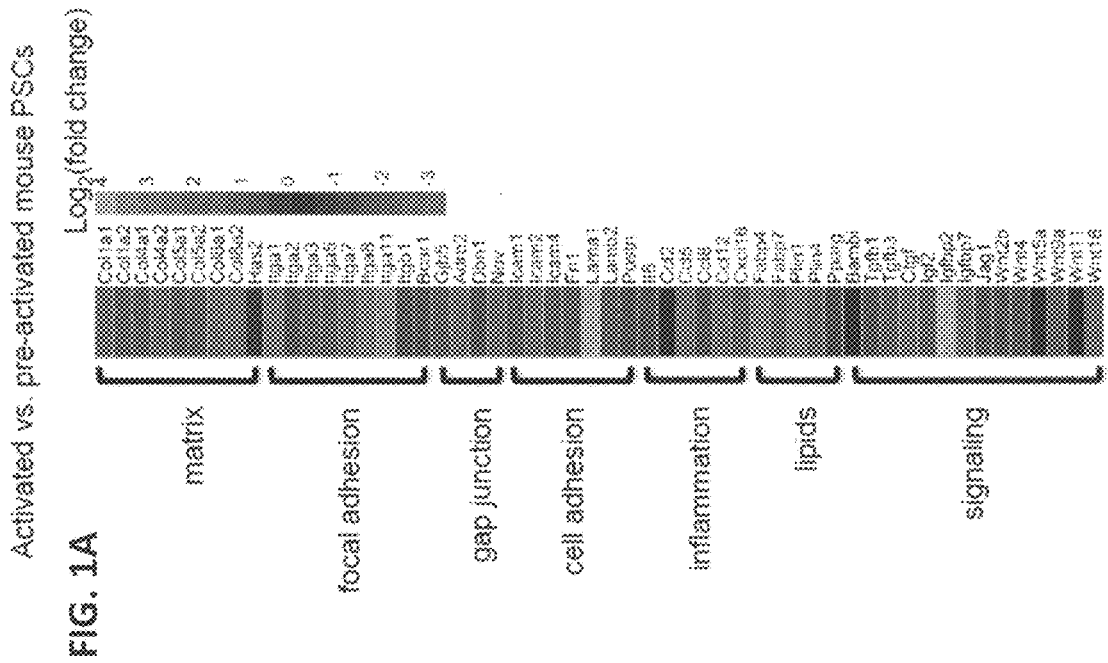

The nucleic and amino acid sequences are shown using standard letter abbreviations for nucleotide bases, as defined in 37 C.F.R. 1.822. Only one strand of each nucleic acid sequence is shown, but the complementary strand is understood as included by any reference to the displayed strand. The Sequence Listing is submitted as an ASCII text file, created on Dec. 3, 2015, 24 KB, which is incorporated by reference herein. In the accompanying sequence listing:

SEQ ID NOS: 1 to 106 show exemplary primer sequences.

DETAILED DESCRIPTION

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a VDR agonist" includes single or plural VDR agonist and is considered equivalent to the phrase "comprising at least one VDR agonist." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. All Genbank Accession numbers referenced herein are incorporated by reference for the sequence available on Jun. 5, 2014. All references, including patents and patent applications, and GenBank® Accession numbers cited herein are incorporated by reference.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

Suitable methods and materials for the practice or testing of the disclosure are described below. However, the provided materials, methods, and examples are illustrative only and are not intended to be limiting. Accordingly, except as otherwise noted, the methods and techniques of the present disclosure can be performed according to methods and materials similar or equivalent to those described and/or according to conventional methods well known in the art and as described in various general and more specific references that are cited and discussed throughout the present specification.

Terms

In order to facilitate review of the various embodiments of the disclosure, the following explanations of specific terms are provided.

Administration: Includes oral, rectal, vaginal, transdermal, and parenteral administration. Generally, parenteral formulations are those that are administered through any possible mode except ingestion. This term also refers to injections, whether administered intravenously, intrathecally, intramuscularly, intraperitoneally, intra-articularly, intratumorally, or subcutaneously, and various surface applications including intranasal, inhalational, intradermal, and topical application, for instance. Thus, a VDR agonist, as well as chemotherapies and biotherapies, can be administered by any method known in the art.

Contact: To bring one agent into close proximity to another agent, thereby permitting the agents to interact. For example, a composition containing a VDR agonist can be applied to a cell (for example in tissue culture), or administered to a subject, thereby permitting the VDR agonist to interact with cells (such as stellate cells or cancer cells) in vitro or in vivo.

C-X-C motif ligand 12 (CXCL12): OMIM 600835. Also known as a stromal cell-derived factor 1 (SDF1). A stromal cell-derived alpha chemokine member of the intercrine family. The encoded protein functions as the ligand for the G-protein coupled receptor, chemokine (C-X-C motif) receptor 4, and plays a role in many diverse cellular functions, including embryogenesis, immune surveillance, inflammation response, tissue homeostasis, and tumor growth and metastasis. CXCL12 sequences are publically available, for example from GenBank® sequence database (e.g., accession numbers NP_001171605.1, AAV49999.1, AAT76437.1, CR450283.1, NM_001009580.1, and AY802782.1). One of ordinary skill in the art can identify additional CXCL12 nucleic acid and protein sequences, including CXCL12 variants (such as variants that have CXCL12 activity and retain at least 98%, at least 95%, at least 90%, at least 85%, or at least 80% sequence identity to a native CXCL12 sequence, such as those provided above).

Isolated: An "isolated" biological component (such as a nucleic acid molecule, peptide, or cell) has been purified away from other biological components in a mixed sample (such as a cell extract). For example, an "isolated" peptide or nucleic acid molecule is a peptide or nucleic acid molecule that has been separated from the other components of a cell in which the peptide or nucleic acid molecule was present (such as an expression host cell for a recombinant peptide or nucleic acid molecule).

Pancreatic cancer: A malignant tumor within the pancreas. The prognosis is generally poor. About 95% of pancreatic cancers are adenocarcinomas. The remaining 5% are tumors of the exocrine pancreas (for example, serous cystadenomas), acinar cell cancers, and pancreatic neuroendocrine tumors (such as insulinomas). An "insulinoma" is a cancer of the beta cells that retains the ability to secrete insulin. Patients with insulinomas usually develop neuroglycopenic symptoms. These include recurrent headache, lethargy, diplopia, and blurred vision, particularly with exercise or fasting. Severe hypoglycemia may result in seizures, coma and permanent neurological damage. Symptoms resulting from the catecholaminergic response to hypoglycemia (for example, tremulousness, palpitations, tachycardia, sweating, hunger, anxiety, nausea). A pancreatic adenocarciona occurs in the glandular tissue. Symptoms include abdominal pain, loss of appetite, weight loss, jaundice and painless extension of the gallbladder.

Classical treatment for pancreatic cancer, including adenocarcinomas and insulinomas includes surgical resection (such as the Whipple procedure) and chemotherapy with agent such as one or more of fluorouracil, gemcitabine, erlotinib, and protein-bound paclitaxel (Abraxane®), such as a combination of gemcitabine/Abraxane®.

Pancreatitis: An inflammation of the pancreas. In some examples is caused by a GLP-1 agonist, such as those used to treat or manage type II diabetes. In one example, a subject having pancreatitis caused by a GLP-1 agonist is treated using the disclosed methods. In another example, a subject being treated with (or previously treated with) a GLP-1 agonist is treated using the disclosed methods in order to prevent development of pancreatitis in the future.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of the compositions herein disclosed. For example a VDR agonist, chemotherapeutic, or biologic, can be administered in the presence of on or more pharmaceutically acceptable carriers.

In general, the nature of the carrier will depend on the particular mode of administration being employed. For instance, parenteral formulations usually include injectable fluids that include pharmaceutically and physiologically acceptable fluids such as water, physiological saline, balanced salt solutions, aqueous dextrose, glycerol or the like as a vehicle. For solid compositions (for instance, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. Embodiments of other pharmaceutical compositions can be prepared with conventional pharmaceutically acceptable carriers, adjuvants, and counter-ions, as would be known to those of skill in the art. The compositions in some embodiments are in the form of a unit dose in solid, semi-solid, and liquid dosage forms, such as tablets, pills, capsules, lozenges, powders, liquid solutions, or suspensions.

Subject: Living multi-cellular vertebrate organisms, a category that includes both human and non-human mammals. The methods and compositions disclosed herein have equal applications in medical and veterinary settings. Therefore, the general term "subject" is understood to include all animals, including, but not limited to, humans or veterinary subjects, such as other primates (including monkeys), dogs, cats, horses, and cows. In one example, the subject is one who has or can develop diabetes, such as type 2 diabetes. In one example, the subject is one who has or can develop a pancreatic disorder, such as pancreatitis (such as that due to taking a GLP-1 agonist) or pancreatic cancer (such as pancreatic ductal adenocarcinoma). In one example a subject is one who has a cancer, such as a cancer of the lung (e.g., NSCLC), kidney (e.g., renal cell carcinoma), prostate, liver (e.g., hepatocellular carcinoma, cholangiocarcinoma, angiosarcoma, or hemangiosarcoma), or pancreas (e.g., PDA).

Therapeutically effective amount: An amount of a therapeutic agent (such as a VDR agonist, chemotherapeutic, or biologic), alone or in combination with other agents sufficient to prevent advancement of a disease, to cause regression of the disease, or which is capable of relieving symptoms caused by the disease. In one example a therapeutically effective amount of a vitamin D receptor agonist is used to prevent or treat a symptom associated with pancreatitis induced by GLP-1 agonists, for example vomiting, internal bleeding, increased blood pressure, pain, and inflammation or swelling of the pancreas. In one example a therapeutically effective amount of a VDR agonist in combination with a therapeutically effective amount of a chemotherapeutic or biologic is use to prevent or treat a symptom associated with cancer, such as cancer of the liver, kidney, pancreas, prostate, bile duct or lung, for example reducing the size or volume of a tumor, reducing metastasis of a tumor, reducing a number of tumor cells in a tumor, reducing the rate of growth of a tumor, and increasing an amount of chemotherapeutic or biologic in the tumor. In one example, a therapeutically effective amount is an amount of a composition provided herein that includes a vitamin D receptor agonist sufficient to reduce symptoms of pancreatitis or a cancer of the liver, kidney, pancreas, prostate, bile duct or lung, for example by at least 10%, at least 20%, at least 50%, at least 70%, or at least 90% (as compared to no administration of the VDR agonist.

Treating or preventing a disease: Treatment refers to a therapeutic intervention that ameliorates a sign or symptom of a disease or pathological condition (for instance, pancreatitis induced by a GLP-1 agonist, or cancer of the liver, kidney, pancreas, prostate, bile duct or lung) after it has begun to develop. Prevention refers to inhibiting the full development of a disease, for example in a person who is known to have a predisposition to a disease such as a person who has been or is at risk for developing pancreatitis, such as a subject receiving one or more GLP-1 agonists.

Vitamin D: A group of fat-soluble secosteroid prohormones and hormones, the two major forms of which are vitamin D2 (ergocalciferol) and vitamin D3 (cholecalciferol), which are converted to 1α,25 dihydroxyvitamin $D_3$ (1α,25-(OH)$_2$-D$_3$), also known as calcitriol, the physiologically active form of vitamin D.

Vitamin D agonist or analog: Any compound, synthetic or natural, that binds to and activates the vitamin D receptor, such as a VDR ligand (e.g., calcitriol), VDR agonist precursor, vitamin D analogs, vitamin D precursors. Specific, non-limiting examples of natural and synthetic vitamin D agonists and analogs include 1α,25(OH)$_2$D$_3$, LG190090, LG9190119, LG190155, LG190176, and LG190178 (see, for instance, Boehm et al., (1999) *Chemistry & Biology*, 6:265-275); LY2108491, and LY2109866 (Ma et al., (2006) *J Clin. Invest.*, 116:892-904); 2β-(3-Hydroxypropoxy)1α, 25-Dihydroxyvitamin D$_3$ (ED-71) (Tsurukami et al., (1994) *Calcif. Tiss. Int.* 54:142-149); EB1089 (Pepper et al., (2003) *Blood*, 101:2454-2460); OCT(22-oxa-calcitrol) (Makibayashi et al., (2001) *Am. J. Path.*, 158:1733-1741); (1αOH-2,19-nor-25hydroxyvitaminD$_3$) and (1,3-Deoxy-2-CHCH$_2$OH-19-nor-25-hydroxyvitaminD3) (Posner et al., (2005) *Bioorganic & Medicinal Chemistry*, 13:2959-2966) and any of the vitamin D analogs disclosed in Rey et al., (1999) *J. Organic Chem.*, 64:3196-3206; and bile acid derivatives such as lithochoic acid (LCA) and ursodoxycholic acid (UDCA) (see, for instance, Nehring et al., (2007) *PNAS*, 104:10006-10009; Makishima et al., (2002) *Science*, 296:1313-1316; Copaci et al., (2005) *Rom. J. Gastroenterol.*, 14:259-266). Each of these references is hereby incorporated by reference in its entirety.

Vitamin D precursor: Any compound capable of being converted to an agonist of the vitamin D receptor by an enzyme. In certain, non-limiting examples, that enzyme is CYP27B1. Specific, non-limiting examples of vitamin D precursors include vitamin D$_3$ (cholecalciferol), 25-hydroxy-vitamin D$_3$ (25-OH-D$_3$) (calcidiol), as well as vitamin D2 (ergocalciferol) and its precursors.

Vitamin D receptor (VDR): A member of the steroid hormone family of nuclear receptors. VDR possesses the common nuclear receptor structure, for example, is comprised of an N-terminal activation domain, a DNA-binding region (DBD) with two zinc finger domains, a hinge region and a ligand-binding domain (LBD). VDR activated gene transcription requires initial nuclear translocation via importin-α, heterodimerization with RXR, and binding to response elements present in target genes. VDR is known to regulate genes associated with the maintenance of calcium and phosphate homeostasis in the intestine and kidney. The signal initiated by VDR/RXR heterodimers is modulated by the association of co-activating or co-repressing proteins and also depends on other signaling partners in the nuclear compartment. The VDR/RXR heterodimer is non-permissive, in that the presence or absence of RXR ligands is not known to affect VDR responses.

Until recently the only known physiological ligand for VDR was 1α,25(OH)$_2$D3 (calcitriol). However, specific bile acids such as LCA and some derivatives (LCA-acetate, LCA-formate, 3-keto LCA) also can activate VDR.

Methods of Treating or Preventing a Disorder Due to CXCL-12 Activity

A. Overview

The poor clinical outcome in pancreatic ductal adenocarcinoma (PDA) has been attributed to intrinsic resistance to chemotherapy and a growth-permissive tumor microenvironment. Conversion of quiescent to activated pancreatic stellate cells (PSCs) is thought to be a key switch in driving the severe stromal reaction that characterizes PDA. It is shown herein that the vitamin D receptor (VDR) is expressed in activated human pancreatic tumor stroma as well as in in vivo models of pancreatitis, a known risk factor for PDA. Notably, treatment with the VDR ligand calcipotriol markedly reduced inflammation and fibrosis during pancreatitis and a more pronounced form of the disease developed in VDR knockout mice. It is shown that VDR acts as a master transcriptional regulator of PSCs to reprise the quiescent state such that ligand-induced stromal remodeling increased intratumoral gemcitabine levels 5-fold and reduced tumor volume in vivo. Thus, stromal VDR activation abates chemotherapeutic drug resistance. This disclosure describes a molecular strategy through which transcriptional reprogramming of tumor stroma rescues/fosters chemotherapeutic response and advocates a reevaluation of vitamin D as an adjunct therapy for PDA.

The emerging role for tumor stroma as the 'fuel supply-line' for cancer offers an important advance from focusing on the cancer cell itself. Indeed, the approach of targeting VDR disclosed herein to transcriptionally reprogram the stroma, simultaneously affecting multiple pathways including inflammatory cytokines, growth factors and angiogenesis, increased the efficacy of gemcitabine treatment in PDA. Furthermore, VDR ligand reduces fibrosis and inflammation in both acute and chronic murine pancreatitis. This is significant as pancreatitis lacks any mechanistic based therapy and is a known risk factor for pancreatic cancer. Recently, 'cistromic antagonism' has been demonstrated, in which VDR activation inhibits the fibrogenic program in activated stellate cells by blocking TGFβ/SMAD signaling (Ding et al., 2013). Together with the data presented herein, these results demonstrate that a wound repair response that engages the TGFβ/SMAD pathway is activated in pancreatic stellate cells by paracrine signaling from cancer cells, inflammation, or other cellular stressors, that is restricted by VDR signaling at the level of the genome. The balance between these opposing pathways may be tipped unfavorably by chronic tissue damage or by vitamin D deficiency, which may explain in part the inverse correlation between plasma vitamin D levels or vitamin D intake and pancreatic cancer risk (Skinner et al., 2006; Wolpin et al., 2012) and the link between vitamin D deficiency and chronic pancreatitis (Mann et al., 2003).

Transcriptional remodeling of pancreatic tumor stroma via VDR activation broadly impairs the capacity of PSCs to support tumor growth. Key features of tumor-stroma interaction negatively regulated by VDR include the extracellular matrix (Jacobetz et al., 2013; Provenzano et al., 2012), the Shh pathway (Olive et al., 2009), cytokines/chemokines such as IL6 and others (Fukuda et al., 2011; Ijichi et al., 2011; Lesina et al., 2011), and growth factors such as CTGF (Aikawa et al., 2006). This gains significance in light of recent work demonstrating that inhibition of stroma-derived survival factor CTGF potentiates the antitumor response to gemcitabine (Neesse et al., 2013). Differences exist between stromal ablation and stromal remodeling therapeutic strategies. The notion that cellular and structural components of a "normal" microenvironment exert tumor-suppressive forces and signals has been discussed previously (Bissell and Hines, 2011), though this remains to be demonstrated in the pancreas. As VDR ligand pushes activated PSCs toward a more quiescent, "normal" phenotype, it is conceivable that remodeled PSCs exert such homeostatic control to negatively regulate tumor growth or promote differentiation, a benefit that would not be harnessed by ablation of stroma altogether.

PDA stroma also limits chemotherapeutic efficacy by blocking drug delivery, a result of severe hypovascularity attributable in part to dense extracellular matrix. VDR ligand significantly reduced the fibrotic component of the tumor and increased intratumoral vasculature. It is shown herein that activated PSCs express antiangiogenic factors such as thrombospondin-1, predicted to contribute to the hypovascularity which characterizes PDA. The antiangiogenic subset of PSC activation signature genes was suppressed by VDR ligand in vitro and, importantly, combination therapy induced improvement of tumor vascularity and drug delivery in vivo. Matrix degradation strategies which increase intratumoral blood flow and gemcitabine delivery have been shown to improve survival in PDA (Jacobetz et al., 2012; Provenzano et al., 2012). However, the significance of VDR-mediated stromal remodeling and improved vascularity with respect to long-term tumor growth and metastatic potential are currently under investigation. Indeed, the recent failure of clinical trials exploring the therapeutic potential of Shh pathway inhibition in combination with gemcitabine in pancreatic cancer bring to light potential limitations of stromal depletion therapy in the context of current treatment strategies. Conceptually, opening the tumor stroma and increasing functional vasculature suggests the dual effect of creating a window for therapeutic delivery, and heightening the potential for dissemination through the bloodstream. Despite these caveats, the data provided herein indicates that stromal agents will show improved clinical outcome when paired with potent targeted therapies which rapidly kill cancer cells.

Consideration of VDR activation as a mechanism for signal-dependent transcriptional remodeling of stroma in pancreatitis and pancreatic cancer is important as these diseases have very limited therapeutic options. The marked reductions in fibrosis and inflammation induced by VDR activation in both acute and chronic pancreatitis models, combined with the increased therapeutic efficacy of calcipotriol+Gemcitibine treatment in PDA models, identify this pathway for the development of sorely needed therapeutic alternatives. Though cancer cell-intrinsic resistance to current chemotherapies remains a major obstacle, the VDR-mediated stromal remodeling paradigm presented here may be favorable when combined with novel therapies directly targeting the neoplasia itself. Simultaneous targeting of tumor and non-tumor components is a simple and potentially widely applicable strategy to overcome chemoresistance in pancreas and other stroma-associated cancers.

Based on the data provided herein, methods for reducing the biological activity of C-X-C motif ligand 12 (CXCL12) are provided. In some examples, such methods include contacting stellate cells (such as those expressing and secreting CXCL12) with a therapeutically effective amount of one or more VDR agonists, thereby reducing the biological activity of CXCL12 (such as its production and/or secretion). Such methods can be performed in vitro (for example by contacting cells in culture expressing the CXCL12 with one or more VDR agonists) or in vivo (for example by administering to a subject one or more VDR agonists). In some examples, the subject treated is a mammalian subject, such as a human subject.

The biological activity can include one or more of CXCL12 nucleic acid expression (such as mRNA or cDNA expression), CXCL12 protein expression, CXCL12 secretion by a cell (such as a stellate cell), CXCL12 protein stability, CXCL12 binding to tumor cells, CXCR4 signaling in tumor cells, and CXCL12 preventing T-cell binding to tumor cells. VDR agonist that reduces the biological activity of a CXCL12 protein need not completely inhibit CXCL12 protein activity. In some examples, such compounds reduce CXCL12 protein activity by at least 10%, at least 20%, at least 25%, at least 40%, at least 50%, at least 75%, at least 80%, at least 90%, or at least 95%.

Thus, in one example, a VDR agonist that reduces the biological activity of CXCL12 can reduce CXCL12 nucleic acid expression (such as mRNA or cDNA expression by a stellate cell) by at least 10%, at least 20%, at least 25%, at least 40%, at least 50%, at least 75%, at least 80%, at least 90%, or at least 95%, as compared to an absence of the VDR agonist. In one example, a VDR agonist that reduces the biological activity of CXCL12 can reduce CXCL12 protein expression (such as protein expression by a stellate cell) by at least 10%, at least 20%, at least 25%, at least 40%, at least 50%, at least 75%, at least 80%, at least 90%, or at least 95%, as compared to an absence of the VDR agonist. In one example, a VDR agonist that reduces the biological activity of CXCL12 can reduce secretion of CXCL12 by a cell (such as by a stellate cell) by at least 10%, at least 20%, at least 25%, at least 40%, at least 50%, at least 75%, at least 80%, at least 90%, or at least 95%, as compared to an absence of the VDR agonist. In one example, a VDR agonist that reduces the biological activity of CXCL12 can reduce the stability of CXCL12 protein by at least 10%, at least 20%, at least 25%, at least 40%, at least 50%, at least 75%, at least 80%, at least 90%, or at least 95%, as compared to an absence of the VDR agonist. In one example, a VDR agonist that reduces the biological activity of a CXCL12 protein can reduce the binding of CXCL12 to a tumor cell (such as a cancer cell of the liver, pancreas, lung, prostate, bile duct, or kidney) by at least 10%, at least 20%, at least 25%, at least 40%, at least 50%, at least 75%, at least 80%, at least 90%, or at least 95%, as compared to an absence of the VDR agonist. In one example, a VDR agonist that reduces the biological activity of CXCL12 can reduce CXCR4 signaling in a tumor cell (such as in a cancer cell of the liver, pancreas, lung, prostate, bile duct, or kidney) by at least 10%, at least 20%, at least 25%, at least 40%, at least 50%, at least 75%, at least 80%, at least 90%, or at least 95%, as compared to an absence of the VDR agonist. In one example, a VDR agonist that reduces the biological activity of a CXCL12 protein can reduce the ability of CXCL12 "hide" or "mask" a tumor cell (such as a cancer cell of the liver, pancreas, lung, prostate, bile duct, or kidney) from a T-cell by at least 10%, at least 20%, at least 25%, at least 40%, at least 50%, at least 75%, at least 80%, at least 90%, or at least 95%, as compared to an absence of the VDR agonist. Thus, in some examples, a VDR agonist that reduces the biological activity of a CXCL12 protein can increase the ability of a T cell to bind to or recognize a tumor cell by at least 10%, at least 20%, at least 25%, at least 40%, at least 50%, at least 75%, at least 80%, at least 90%, at least 95%, at least 100%, at least 200%, at least 300%, at least 400%, at least 500%, or at least 1000%, as compared to an absence of the VDR agonist.

Methods of treating a tumor, such as a cancer that has associated stellate cells, in a subject are provided. Such methods can include administering to the subject a therapeutically effective amount of one or more VDR agonists and a therapeutically effective amount of one or more chemotherapeutic or biological agents (such as a monoclonal antibody). The one or more chemotherapeutic or biological agents used can be determined with routine skill based on the tumor that the subject has. For example, if the tumor is a pancreatic cancer (e.g., pancreatic ductal adenocarcinoma, PDA), the one or more chemotherapeutic agents can include one or more of fluorouracil, gemcitabine, erlotinib, and protein-bound paclitaxel (e.g., Nab-paclitaxel, Abraxane®); if the tumor is non small cell lung cancer (NSCLC) the one or more chemotherapeutic agents can include one or more of methotrexate, gemcitabine, paclitaxel, cisplatin, azacitidine, and entinostat; if the tumor is a kidney cancer (e.g., renal cell carcinoma) the one or more chemotherapeutic or biological agents can include one or more of everolimus, aldesleukin, evacizumab, axitinib, bevacizumab, sorafenib tosylate, pazopanib hydrochloride, sunitinib malate, and temsirolimus; if the tumor is a prostate cancer the one or more chemotherapeutic or biological agents can include one or more of abiraterone acetate, bicalutamide, cabazitaxel, degarelix, denosumab, eocetaxel, enzalutamide, goserelin acetate, leuprolide acetate, prednisone, radium 223 dichloride, sipuleucel-T, and docetaxel; and if the tumor is a liver cancer (e.g., hepatocellular carcinoma) and the one or more chemotherapeutic agents comprise one or more of sorafenib, doxorubicin, gemcitabine, cisplatin, interferon, doxorubicin, and fluorouracil (such as PIAF: cisplatin, interferon, doxorubicin, and fluorouracil). In one example, the one or more VDR agonists can be administered prior to the one or more chemotherapeutic or biological agents. In another example, the one or more VDR agonists are administered concurrently with the one or more chemotherapeutic or biological agents.

In a specific example, the tumor is a PDA and the one or more chemotherapeutic agents comprise (a) gemcitabine, (b) gemcitabine and erlotinib, or (c) gemcitabine and protein-bound paclitaxel. Thus, the disclosure provides a method of treating pancreatic ductal adenocarcinoma by a method that includes (1) administering to a mammalian subject having a PDA a therapeutically effective amount of one or more VDR agonists, and (2) administering a therapeutically effective amount of a chemotherapy selected from the group consisting of fluorouracil, gemcitabine, erlotinib, protein-bound paclitaxel, or combinations thereof, thereby treating the pancreatic ducal adenocarcinoma in the subject. In a specific example, the one or more VDR agonists is calcipotriol or paricalcitol and the chemotherapy comprises (a) gemcitabine (e.g., 1000 mg gemcitabine /m2 over 30 minutes once weekly for up to 7 weeks followed by a week of rest, then once weekly for three weeks of every four weeks), (b) gemcitabine and erlotinib, or (c) gemcitabine and protein-bound paclitaxel.

Also provided herein are methods of using a therapeutically effective amount of one or more vitamin D receptor (VDR) agonists (including calcitriol or calcipotriol or a precursor or analog thereof, as well as other VDR ligands, vitamin D precursors, vitamin D analogs, $1\alpha,25(OH)_2$-$D_3$, VDR ligands, and precursors of VDR agonists) for the treatment of pancreatitis, for instance pancreatitis induced by glucagon-like peptide (GLP) agonists, such as GLP-1 agonists. The pancreatitis can be acute or chronic. Thus, described herein are methods of treating pancreatitis induced by GLP-1 agonists in a subject, such as a subject receiving one or more GLP-1 agonists for treatment of diabetes, such as type 2 diabetes. In some examples the method includes selecting a subject having type 2 diabetes that is currently or has previously been treated with a GLP-1 agonist. In some cases such subject will have or be at risk for developing pancreatitis. In a specific example, the present disclosure provides a method of treatment, which includes providing a human patient with features or symptoms of pancreatitis due to GLP-1 agonist administration a therapeutic composition including a VDR agonist, and administering the therapeutic composition to the patient under conditions such that said features or symptoms (such as vomiting, internal bleeding, increased blood pressure, pain or swelling) are reduced. In some examples, the subject is at risk for developing pancreatitis due to GLP-1 agonist administration, and the therapeutic composition is administered prophylactically. In one embodiment, the prophylactic administration of the VDR agonist delays the onset of the symptoms of GLP-1 agonist induced pancreatitis. For example, prophylactic administration of a VDR agonist prevents the onset of one or more symptoms or features of GLP-1 agonist induced pancreatitis.

GLP-1 agonists (also referred to in the literature as GLP-1 mimetics and incretin mimetics) are a class of drugs that lower blood glucose concentrations, and are thus used to treat or manage type 2 diabetes. As compared to older insulin secretagogues, such as sulfonylureas or meglitinides, GLP-1 agonists have a lower risk of causing hypoglycemia. However, such compounds can also have adverse effects, including pancreatitis. Exemplary GLP-1 agonists include but are not limited to exenatide, taspoglutide, insulin glargine, pioglitazone, albiglutide, lixisenatide, saxagliptin, liraglutide, linagliptin, alogliptin, sitagliptin and metformin/sitagliptin. Byetta® (exenatide, Merck) is usually administered subcutaneously twice daily; taspoglutide (Roche) is usually administered subcutaneously weekly, insulin glargine (Lantus®, Sanofi-Aventis); is usually administered subcutaneously daily, pioglitazone (Actos®, Takeda); is usually administered orally daily (e.g., 15 mg, 30 mg, or 45 mg), albiglutide (Tanzeum®, GlaxoSmithKline) is usually administered subcutaneously once weekly; lixisenatide (Lyxumia® Sanofi-Aventis) is usually administered daily by injection (e.g., 10 μg per day for 14 days, then 20 μg/day); Bydureon® (exenatide, Bristol-Myers Squibb) is usually administered weekly by injection; Onglyza® (saxagliptin, AstraZeneca) is usually administered orally daily (e.g., 2.5 mg or 5 mg); Victoza® (liraglutide, Novo Nordisk); is usually administered subcutaneously daily (e.g., 0.6, 1.2, or 1.8 mg); Tradjenta® (linagliptin, Eli Lilly and Boehringer Ingelheim) is usually administered orally daily (e.g., 5 mg); Nesina® (alogliptin, Takeda) is usually administered orally daily (e.g., 25 mg); Januvia® (sitagliptin) and the related Janumet® (a mixture of metformin and sitagliptin, Merck) are usually administered orally daily (e.g., 25, 50 or 100 mg for Januvia® and 50 or 100 mg sitagliptin and 1000 or 2000 mg metformin hydrochloride for Janumet® or Janumet XR®). In some examples, GLP-1 agonists (such as those listed above) are administered subcutaneously or orally on a daily, twice daily, biweekly or once weekly basis.

The method in particular examples includes administering a therapeutically effective amount of one or more VDR agonists to a subject having or at risk to develop pancreaitis induced by GLP-1 agonists, thereby treating or preventing the pancreatitis.

The VDR agonists contacted with cells in vitro or administered to a subject can be present in a pharmaceutically acceptable carrier. The VDR agonist in some examples is a non-naturally occurring agonist. Examples of non-naturally occurring VDR agonists include but are not limited to: KH1060 (lexacalcitol), BXL-628 (elocalcitol), MC1288, CB966, B\CB 1093, GS 1558, TX527 ([19-nor-14,20-bisepi-23-yne-1,25(OH)2D3), ED-71 (eldecalcitrol), BXL-01-0029, doxercalciferol, EB 1089 (seocalcitol), paricalcitol, calcipotriol, and combinations thereof. Other examples include maxacalcitol (OCT), tacalcitol, alfacalcidol, SM-10193, EB1072, EB1129, EB1133, EB1155, EB1270, MC1288, EB1213, CB1093, VD2656, VD2668, VD2708, VD2716, VD2728, VD2736, GS1500, GS1558, KH1060, ZK161422, and combinations thereof. The structures of some are shown below.

KH1060

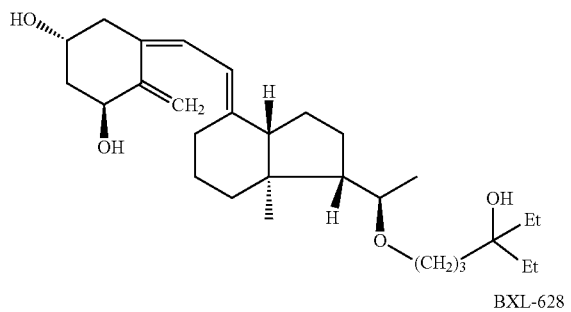

BXL-628

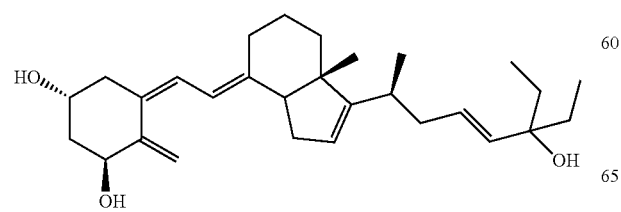

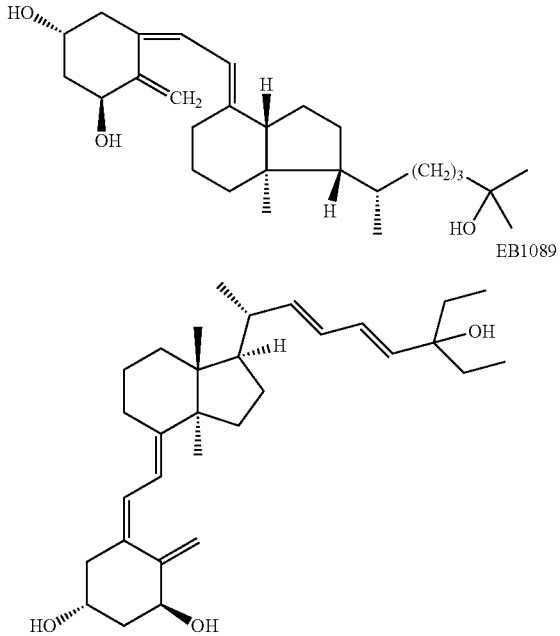

MC1288

EB1089

Exemplary VDR agonists include but are not limited to vitamin D, a vitamin D precursor, a vitamin D analog, a vitamin D receptor ligand, a vitamin D receptor agonist precursor, or combinations thereof. In certain embodiments, the treatment is a VDR agonist precursor such as 25-hydroxy-vitamin $D_3$ (25-OH-$D_3$) (calcidiol); vitamin $D_3$ (cholecalciferol); vitamin $D_2$ (ergocalciferol), or combinations thereof. In certain embodiments, the treatment is an agonist ligand of VDR, such as 1α,25-dihydroxyvitamin $D_3$ (calcitriol). Thus, in some examples subjects having or at risk to develop pancreatitis induced by GLP-1 agonists are selected for treatment with the disclosed methods (for example to treat existing pancreatitis or to prevent or delay the development of pancreatitis). In other examples, subjects having a tumor that has associated stellate cells are selected for treatment with the disclosed methods (for example to treat cancer of the liver, kidney, pancreas, lung, bile duct, or prostate).

In one example, the VDR agonist is calcipotriol, which is a synthetic derivative of calcitriol or vitamin D. Calcipotriol has minimal effects on calcium homeostasis. Calcipotriol is soluble to 100 mM in DMSO and to 100 mM in ethanol. In one example, calcipotriol has the structure:

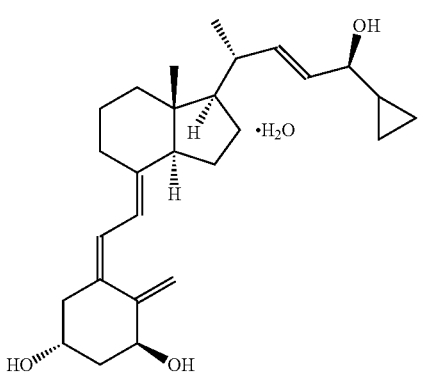

In one example, the VDR agonist is paricalcitol (19-nor-1,25-(OH)$_2$-vitamin D2). Paricalcitol has the structure:

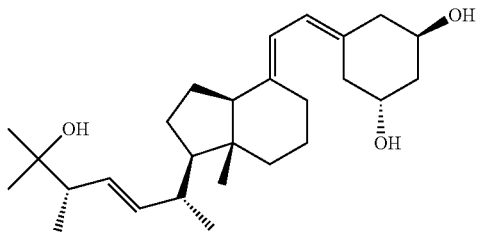 [SMILES: C[C@H](/C=C/[C@H](C)C(C)(C)O)[C@H]1CC[C@H]2/C(=C/C=C3C[C@@H](O)C[C@H](O)C3)CCC[C@]12C]

In some examples, 1α,25(OH)$_2$D$_3$ or a vitamin D precursor or analog is used as a VDR agonist. It is not necessary to use the most biologically active form of vitamin D to achieve a beneficial therapeutic effect. The naturally occurring ligand of the vitamin D receptor is calcitriol. In one embodiment, precursors of calcitriol (such as calcidiol) are administered to a subject, and are then converted within the target cell population to calcitriol. This approach has the advantage that the local intestinal as well as the systemic effects of calcitriol on calcium homeostasis can be significantly avoided, even when large doses of the precursor are administered.

In one embodiment, a VDR ligand or other VDR agonist or agonist precursor that is resistant to deactivation by CYP24A1 is used to achieve more effective and longer lasting VDR activation in target cell populations. In specific examples, the VDR ligand is one that can be activated by CYP27B1 while being resistant to deactivation by CYP24A1. This permits VDR activation in target cell populations in the pancreas, while minimizing undesirable systemic effects on calcium homeostasis.

In one embodiment, VDR ligands or other VDR agonists that can bind to and activate the VDR are used to prevent or attenuate the processes of injury in the pancreas due to GLP-1 administration. In some embodiments, ligands of VDR are used alone, whereas in other embodiments they are used in combination with other compositions routinely used to treat pancreatitis.

The effects of VDR agonists on pancreatitis or cancer are monitored, in some embodiments, by blood, serum, plasma amylase, or lipase, as well as tests of organ function (e.g., pancreatic exocrine and endocrine function). In other embodiments, pancreatitis or cancer is monitored by imaging techniques, including but not limited to radiological, nuclear medicine, ultrasound, and magnetic resonance.

In certain examples, the administration includes oral or parenteral (e.g., oral, intraperitoneal, or intravenous) administration of the VDR agonist. In particular examples, the VDR agonist is a vitamin D precursor is administered at a dose of at least 1 international units (IU), such as at least 5 IU, at least 10 IU, at least 10 IU, at least 100 IU, at least 1000 IU, at least 5000 IU, at least 10,000 IU, at least 50,000 IU, at least 100,000 IU, or at least 500,000 IU, for example from 5 IU about 50,000 IU, 5 IU to 10,000 IU, 10 to 1000 IU, or 50,000 IU to 500,000 IU. Generally, an IU is unit of measurement for the amount of a substance, such as a vitamin D precursor, based on specific biological activity or effect as defined by an international body and accepted internationally. In some examples, for vitamin D 1 IU is the biological equivalent of 0.025 μg cholecalciferol/ergocalciferol.

In certain examples, the subject is a mammalian subject, such as a human or other primate or a horse, dog, or cat. For example, the subject can be one with type 2 diabetes, such as subject receiving a GLP-1 agonist for the treatment or management of their diabetes, or a subject who has previously been treated with a GLP-1 agonist. In one example, the subject is one with a tumor, such as a cancer of the kidney, liver, pancreas, prostate, bile duct, or lung. Such subjects, such as a mammal, in some examples is administered one or more VDR agonists over a period of at least 1 day, at least 7 days, at least 14 days, at least 30 days, at least 60 days, at least 6 months, at least 1 year, at least 2 years or at least 5 years.

In another example, the subject (such as a human or laboratory mammal, such as a rat, mouse or non-human primate) can be administered a VDR agonist at concentrations and over a period of time sufficient to increase expression of VDR. In one example, a mammal is administered one or more VDR agonists over a period of at least 1 day, at least 7 days, at least 14 days, at least 30 days, at least 60 days, at least 6 months, at least 1 year, at least 2 years or at least 5 years. In some examples, a mammal is administered at least 1 international unit (IU), such as at least 5 IU, at least 10 IU, at least 10 IU, at least 100 IU, at least 1000 IU, at least 5000 IU, at least 10,000 IU, at least 50,000 IU, at least 100,000 IU, at least 500,000 IU, for example from 5 IU about 50,000 IU, 5 IU to 10,000 IU, 10 IU to 1000 IU, 1000 IU to 500,000 IU, or 50,000 IU to 500,000 IU of one or more VDR agonists.

B. Methods of Treating Tumors that have Associated Stellate Cells

Provided herein are methods of decreasing CXCL12 activity, such as CXCL12 production and/or secretion in/by a stellate cell, which can be used to treat a tumor or cancer that has associated stellate cells. Examples of cancers that can be treated with the methods provided herein include cancer of the kidney, liver, pancreas, prostate, bile duct, and lung. In some embodiments, the method can be used to treat pancreatic cancer. In one example, the cancer is pancreatic ductal adenocarcinoma. Such methods can include administering to the subject a therapeutically effective amount of one or more VDR agonists (such as calcipotriol or paricalcitol) and a therapeutically effective amount of one or more chemotherapeutic or biological agents (such as a monoclonal antibody). The disclosed methods can be combined with surgical resection for the treatment of the cancer, such as surgery following treatment of the tumor with the disclosed methods or surgery prior to treatment with the disclosed methods.

The one or more chemotherapeutic or biological agents used can be determined with routine skill based on the tumor that the subject has. For example, if the tumor is a pancreatic cancer (e.g., pancreatic ductal adenocarcinoma, PDA), the one or more chemotherapeutic agents can include one or more of fluorouracil, gemcitabine, erlotinib, and protein-bound paclitaxel (e.g., Nab-paclitaxel, Abraxane®); if the tumor is a lung cancer (e.g., NSCLC) the one or more chemotherapeutic agents can include one or more of methotrexate, gemcitabine, paclitaxel, cisplatin, azacitidine, and entinostat; if the tumor is a kidney cancer (e.g., renal cell carcinoma) the one or more chemotherapeutic or biological agents can include one or more of everolimus, aldesleukin, evacizumab, axitinib, bevacizumab, sorafenib tosylate, pazopanib hydrochloride, sunitinib malate, and temsirolimus; if the tumor is a prostate cancer the one or more chemotherapeutic or biological agents can include one or more of abiraterone acetate, bicalutamide, cabazitaxel, degarelix, denosumab, eocetaxel, enzalutamide, goserelin acetate, leuprolide acetate, prednisone, radium 223 dichloride, sipuleucel-T, and docetaxel; if the tumor is a cancer of the bile duct (cholangiocarcinoma), the one or more chemotherapeutic or biological agents can include one or more of 5-fluorouracil, leucovorin, gemcitabine, gemcitabine plus cisplatin, irinotecan, capecitabine, and erlotinib (such as 5-fluorouracil+leucovorin or gemcitabine+cisplatin); and if the tumor is a liver cancer (e.g., hepatocellular carcinoma) and the one or more chemotherapeutic agents comprise one or more of sorafenib, doxorubicin, gemcitabine, cisplatin, interferon, doxorubicin, and fluorouracil (such as PIAF: cisplatin, interferon, doxorubicin, and fluorouracil). In a specific example, the tumor is a PDA and the one or more chemotherapeutic agents comprise (a) gemcitabine, (b) gemcitabine and erlotinib, or (c) gemcitabine and protein-bound paclitaxel. Thus, the disclosure provides a method of treating pancreatic ductal adenocarcinoma by a method that includes (1) administering to a mammalian subject having a PDA a therapeutically effective amount of one or more VDR agonists, and (2) administering a therapeutically effective amount of a chemotherapy selected from the group consisting of fluorouracil, gemcitabine, erlotinib, protein-bound paclitaxel, or combinations thereof, thereby treating the pancreatic ducal adenocarcinoma in the subject.

In one embodiment, the combination of a therapeutically effective amount of both one or more VDR agonists and one or more chemotherapeutic or biological agents (such as a monoclonal antibody), synergistically enhances the effects of the one or more chemotherapeutic or biological agents. Without wishing to be bound to a particular theory, it is proposed that the use of the VDR agonist reduces the stellate cell production of CXCL12 thereby reducing the "masking" of tumor cells from T cells by CXCL12. In addition, the VDR agonist reduces the stellate cell production of pro-survival factors such as CTGF or PDGF, negative regulators of angiogenesis and extracellular matrix components making the tumor more accessible to chemotherapeutic or biological agents, thus making the tumor more vulnerable to such agents.

Thus, in some examples, the combination of a therapeutically effective amount of both one or more VDR agonists and one or more chemotherapeutic or biological agents inhibits further growth of, reduces the volume or size of, reduces metastasis of, reduces a sign or a symptom of, reduces a number of tumor cells of, or reduces the rate of growth of, a cancer of the kidney (e.g., RCC), liver (e.g., HCC), pancreas (e.g., PDA), prostate, bile duct, and lung (e.g., NSCLC). In some examples, administration of both a therapeutically effective amount of one or more VDR agonists and one or more chemotherapeutic or biological agents reduces growth or the rate of growth of such cancers by at least 10%, at least 20%, at least 25%, at least 40%, at least 50%, at least 75%, at least 80%, at least 90%, or at least 95% as compared to an absence of the VDR agonist. In one example, administration of both a therapeutically effective amount of one or more VDR agonists and one or more chemotherapeutic or biological agents reduces the volume of such cancers by at least 10%, at least 20%, at least 25%, at least 40%, at least 50%, at least 75%, at least 80%, at least 90%, or at least 95%, as compared to an absence of the VDR agonist. In one example, administration of both a therapeutically effective amount of one or more VDR agonists and one or more chemotherapeutic or biological agents reduces the size of such cancers by at least 10%, at least 20%, at least 25%, at least 40%, at least 50%, at least 75%, at least 80%, at least 90%, or at least 95%, as compared to an absence of the VDR agonist. In one example, administration of both a therapeutically effective amount of one or more VDR agonists and one or more chemotherapeutic or biological agents reduces the metastasis of such cancers by at least 10%, at least 20%, at least 25%, at least 40%, at least 50%, at least 75%, at least 80%, at least 90%, or at least 95%, as compared to an absence of the VDR agonist. In one example, administration of both a therapeutically effective amount of one or more VDR agonists and one or more chemotherapeutic or biological agents reduces a sign or a symptom of such cancers by at least 10%, at least 20%, at least 25%, at least 40%, at least 50%, at least 75%, at least 80%, at least 90%, or at least 95%, as compared to an absence of the VDR agonist. In one example, administration of both a therapeutically effective amount of one or more VDR agonists and one or more chemotherapeutic or biological agents reduces the number of such cancer cells by at least 10%, at least 20%, at least 25%, at least 40%, at least 50%, at least 75%, at least 80%, at least 90%, or at least 95%, as compared to an absence of the VDR agonist.

In one example, administration of both a therapeutically effective amount of one or more VDR agonists and one or more chemotherapeutic or biological agents can reduce the ability of CXCL12 "hide" or "mask" a tumor cell (such as a cancer cell of the liver, pancreas, lung, prostate, bile duct, or kidney) from a T-cell by at least 10%, at least 20%, at least 25%, at least 40%, at least 50%, at least 75%, at least 80%, at least 90%, or at least 95%, as compared to an absence of the VDR agonist. Thus, in some examples, administration of both a therapeutically effective amount of one or more VDR agonists and one or more chemotherapeutic or biological agents can increase the ability of a T cell to bind to or recognize a tumor cell by at least 10%, at least 20%, at least 25%, at least 40%, at least 50%, at least 75%, at least 80%, at least 90%, at least 95%, at least 100%, at least 200%, at least 300%, at least 400%, at least 500%, or at least 1000%, as compared to an absence of the VDR agonist.

In some examples, the combination of a therapeutically effective amount of both one or more VDR agonists and one or more chemotherapeutic or biological agents increases an amount of chemotherapeutic or biologic in a cancer of the kidney (e.g., RCC), liver (e.g., HCC), pancreas (e.g., PDA), prostate, bile duct, and lung (e.g., NSCLC) by at least 10%, at least 20%, at least 25%, at least 40%, at least 50%, at least 75%, at least 80%, at least 90%, at least 95%, at least 100%, at least 200%, at least 300%, at least 400%, at least 500%, or at least 1000%, as compared to an absence of the VDR agonist.

Methods of measuring such parameters of tumor growth and chemotherapeutic/biologic concentrations are known and are provided herein, and such assays can be used to determine if the combination of a therapeutically effective amount of both one or more VDR agonists and one or more chemotherapeutic or biological agents. Exemplary methods for measuring or monitoring tumors include but are not limited to, diagnostic imaging (such as CT scan, x-rays, ultrasound, and the like), microscopic imaging (such as light microscopy, immunofluorescence microscopy, flow cytometry, and the like), biopsies of the tumor, as well as blood diagnostics (e.g., measuring AFP as a marker of HCC, CA 19-9 as a biomarker of PDA, PSA as a biomarker of prostate cancer, and the like). Other exemplary diagnostic methods are provided in the examples below.

Any mode of administration of the VDR agonist and the chemotherapeutic/biologic can be used. In some examples, different modes of administration are used for the VDR agonist and for the chemotherapeutic/biologic. In one example, the VDR agonist is administered orally, intraperitoneally or intravenously and the chemotherapeutic or biologic is administered intravenously. In one example, site-specific administration of the VDR agonist and the chemotherapeutic/biologic can be used, for instance by applying the compound to an area where the tumor is or from which a tumor has been removed, or a region suspected of being prone to tumor development. In some embodiments, sustained intra-tumoral administration (or near-tumoral) is used.

C. Methods of Treating or Preventing GLP Agonist-Induced Pancreatitis

Provided herein are methods reducing inflammatory and fibrotic responses induced in chronic and acute pancreatitis by decreasing the production of inflammatory cytokines and fibrotic proteins from activated stellate cells, which can be used to treat or prevent pancreatitis. In addition, treatment of activated stellate cells will also reduce the production and/or secretion of CXCL12. For example, a therapeutically effective amount of one or more VDR agonists (such as calcitriol or calcipotriol or other non-naturally occurring VDR agonist) can be used to treat pancreatitis, for instance pancreatitis induced by GLP agonists, such as GLP-1 agonists. Such a subject can be one receiving one or more GLP-1 agonists for treatment of diabetes, such as type 2 diabetes. In a specific example, the treatment includes administering to a human patient with features or symptoms of pancreatitis due to GLP-1 agonist a therapeutic composition including a VDR agonist under conditions such that said features or symptoms (such as pain in the epigastric region or right upper quadrant that radiates to the back, mild jaundice, vomiting, internal bleeding, increased blood pressure, pain or swelling) are reduced.

In some examples, the disclosed methods are prophylactic. Thus, the subject treated can be one who is at risk for developing pancreatitis due to GLP agonist administration (e.g., GLP-1 agonist), and the therapeutic composition is administered prophylactically. In one embodiment, the prophylactic administration of the VDR agonist delays the onset of the symptoms of GLP-1 agonist induced pancreatitis.

A VDR agonist that reduces the activation of stellate cells and thereby the production of inflammatory cytokines as well as CXCL12 need not completely inhibit and/or reverse stellate cell activation to treat or prevent the pancreatitis. In some examples, such compounds reduce stellate cell activation by at least 10%, at least 20%, at least 25%, at least 40%, at least 50%, at least 75%, at least 80%, at least 90%, or at least 95%. Thus in one example, a VDR agonist that reduces stellate cell activation can reduce vomiting by at least 10%, at least 20%, at least 25%, at least 40%, at least 50%, at least 75%, at least 80%, at least 90%, or at least 95%, in a subject with or at risk for pancreatitis, as compared to an absence of the VDR agonist. In one example, a VDR agonist that reduces stellate cell activation can reduce internal bleeding by at least 10%, at least 20%, at least 25%, at least 40%, at least 50%, at least 75%, at least 80%, at least 90%, or at least 95%, in a subject with or at risk for pancreatitis, as compared to an absence of the VDR agonist. In one example, a VDR agonist that reduces stellate cell activation can reduce blood pressure by at least 10%, at least 20%, at least 25%, at least 40%, at least 50%, at least 75%, at least 80%, at least 90%, or at least 95%, in a subject with or at risk for pancreatitis, as compared to an absence of the VDR agonist. In one example, a VDR agonist that reduces stellate cell activation can reduce swelling or inflammation of the pancreas by at least 10%, at least 20%, at least 25%, at least 40%, at least 50%, at least 75%, at least 80%, at least 90%, or at least 95%, in a subject with or at risk for pancreatitis, as compared to an absence of the VDR agonist. In one example, a VDR agonist that reduces stellate cell activation can reduce fibrosis of the pancreas by at least 10%, at least 20%, at least 25%, at least 40%, at least 50%, at least 75%, at least 80%, at least 90%, or at least 95%, in a subject with or at risk for pancreatitis, as compared to an absence of the VDR agonist.

Methods of measuring such symptoms and features of pancreatitis are known and are provided herein, and such assays can be used to determine if the VDR agonist reduces such symptoms or features. Exemplary methods include but are not limited to, diagnostic imaging (e.g., radiological, nuclear medicine, ultrasound, and magnetic resonance, such as a CT scan or x-ray) and tests of the blood, serum, plasma amylase, or lipase, as well as tests of pancreatic exocrine and endocrine function (e.g., white blood cell count, glucose levels). For example, the evidence can be improved pancreatic function, lessening of pain, retention of pancreatic function, or a structural change in the pancreas of the subject. Thus, for example, the physician can measure one or more indicators of GLP-1 agonist induced pancreatitis in the subject immediately prior to, or on commencement of the treatment, and again during and after treatment. In certain embodiments, treatment is continued until evidence of relief, cure, or prevention of GLP-1 agonist induced pancreatitis has been achieved. In other embodiments, treatment is continued after evidence of relief, cure, or prevention of GLP-1 agonist induced pancreatitis s has been obtained. Such treatment, in some examples, lasts for the duration of treatment of GLP-1 agonist induced pancreatitis in the subject, or for the lifetime of the subject.

Tests measuring endocrine and/or exocrine pancreatic function can be used for monitoring GLP-1 agonist induced pancreatitis. In some embodiments, pancreatic insufficiency is diagnosed by the presence of the clinical triad of pancreatic calcification, diabetes and steatorrhea. Tests of exocrine pancreatic function include, but are not limited to CCK/secretin stimulation tests, Lundh meal tests, ERCP and pancreatic aspiration, measurement of stool fats and nitrogen or stool trypsin and chymotrypsin, and the bentiromide test and pancreolauryl test, as well as measurements of trypsinogen, lipase, or pancreatic amylase in the blood.

Other methods of diagnosing and measuring the severity of GLP-1 agonist induced pancreatitis are known to those skilled in the art, and it is contemplated that any one of these methods can be used to assess the efficacy of treatment of GLP-1 agonist induced pancreatitis.

D. Vitamin D Receptor (VDR)

VDR possesses the common nuclear receptor structure, for instance is comprised of an N-terminal activation domain, a DNA-binding region (DBD) with two zinc finger domains, a hinge region and a ligand-binding domain (LBD). VDR activated gene transcription requires initial nuclear translocation via importin-α, heterodimerization with RXR, (Yasmin et al., 2005. *J Biol Chem.,* 280(48): 40152-60), and binding to response elements present in target genes. VDR regulates genes associated with the maintenance of calcium and phosphate homeostasis in the intestine and kidney. The signal initiated by VDR/RXR heterodimers is modulated by the association of co-activating or co-repressing proteins and also depends on other signaling partners in the nuclear compartment (Ebert et al., 2006. *Mol Cell Endocrinol.,* 248(1-2):149-59). The VDR/RXR heterodimer is non-permissive, in that the presence or absence of RXR ligands does not affect VDR responses (Shulman et al., 2004. *Cell,* 116(3):417-29). Until recently, the only known physiological ligand for VDR was calcitriol. However, specific bile acids such as LCA and some derivatives (LCA-acetate, LCA-formate, 3-keto LCA) may activate VDR. These bile acid VDR agonists have been shown to induce SULT2A1 expression, a sulfo-conjugating phase II enzyme in intestinal mucosa, which may provide a key defense response of the intestine against the toxic and carcinogenic effects of bile acids (Chatterjee et al., 2005. *Methods Enzymol.*, 400:165-91).

E. Exemplary VDR Agonists

As described above, administration of VDR agonists can be used to treat cancers having active stellate cells and to treat or prevent GLP-1 induced pancreatitis. Exemplary VDR agonists include those molecules that can activate the VDR. Methods of determining if an agent is a VDR agonist are routine. For example, induction of CYP24A1 expression can be measured in VDR-expressing cells contacted with the agent, wherein an increase in CYP24A1 expression (such as a 10- to 20-fold increase in expression) indicates that the agent is a VDR agonist. Other methods include transfected reporter gene constructs and FRET assays. In some example, binding of an agonist to a purified LBD is detected by measuring induced recruitment for coactivator peptides (e.g., LXXLL). For example VDR agonists can increase CYP24A1 expression in a VDR-expressing cell by at least 20%, at least 50%, at least 75%, at least 80%, at least 90% at least 100%, at least 200% or oven at least 1000% or more as compared to the absence of the agonist.

VDR agonists include molecules that can bind to and activate the VDR, such as $1\alpha,25(OH)_2$-D3 and precursors and analogs thereof, VDR ligands, and VDR agonist precursors. The disclosure is not limited to particular vitamin D agonists. A variety of biologically active vitamin D agonists are contemplated. Exemplary agents are known in the art. The VDR agonist in one example is a non-naturally occurring VDR agonist.

VDR agonists include vitamin D compounds, precursors and analogs thereof. Vitamin D compounds useful for the methods provided herein include, but are not limited to compounds which have at least one of the following features: the C-ring, D-ring and 3β-hydroxycyclohexane A-ring of vitamin D interconnected by the 5,7 diene double bond system of vitamin D together with any side chain attached to the D-ring (e.g., compounds with a 'vitamin D nucleus' and substituted or unsubstituted A-, C-, and D-rings interconnected by a 5,7 diene double bond system typical of vitamin D together with a side chain attached to the D-ring).

Vitamin D analogs include those nonsecosteroid compounds capable of mimicking various activities of the secosteroid calcitriol. Examples of such compounds include, but are not limited to, LG190090, LG190119, LG190155, LG190176, and LG1900178 (See, Boehm et al., *Chemistry & Biology* 6:265-275, 1999).

Vitamin D compounds includes those compounds includes those vitamin D compounds and vitamin D analogs which are biologically active in vivo, or are acted upon in a mammalian subject such that the compound becomes active in vivo. Examples of such compounds include, but are not limited to: vitamin D, calcitriol, and analogs thereof [e.g., 1α-hydroxyvitamin $D_3$ (1α-OH-$D_3$), 1,25-dihydroxyvitamin $D_2$ (1,25-(OH)$_2D_2$), 1α-hydroxyvitamin $D_2$ (1α-OH-$D_2$), $1\alpha,25$-(OH)$_2$-16-ene-$D_3$, $1\alpha,25$-(OH)$_2$-24-oxo-16-ene-$D_3$, $1\alpha,24R(OH)_2$-$D_3$, $1\alpha,25(OH)_2$-22-oxa-$D_3$, 20-epi-24-oxa-24a,24b, -dihomo-$1\alpha,25(OH)_2$-$D_3$, 20-epi-22-oxa-24a, 26a,27a, -trihomo-$1\alpha25(OH)_2$-$D_3$, 20-epi-22-oxa-24homo-$1\alpha,25(OH)_2$-$D_3$, 1,25-(OH)$_2$-16,23E-diene-26-trifluoro-19-nor-$D_3$, and nonsecosteroidal vitamin D mimics.

In one example, the VDR agonist is one or more of the following: vitamin D, $1,\alpha25$ dihydroxyvitamin $D_3$, 1α-hydroxyvitamin $D_3$, 1,25-dihydroxyvitamin $D_2$, 1α-hydroxyvitamin $D_2$, $1\alpha,25$-(OH)$_2$-16-ene-$D_3$, $1\alpha,25$-(OH)$_2$-24-oxo-16-ene-$D_3$, $1\alpha,24R(OH)_2$-$D_3$, $1\alpha,25(OH)_2$-22-oxa-$D_3$, 20-epi-22-oxa-24a,24b, -dihomo-$1\alpha,25(OH)_2$-$D_3$, 20-epi-22-oxa-24a,26a,27a, -trihomo-$1\alpha25(OH)_2$-$D_3$, 20-epi-22-oxa-24homo-$1\alpha,25(OH)_2$-$D_3$, and 1,25-(OH)$_2$-16,23E-diene-26-trifluoro-19-nor-$D_3$. In a preferred embodiment, the biologically active vitamin D compound is selected from $1,\alpha25$-dihydroxyvitamin $D_3$, 19-nor-1,25-dihydroxyvitamin $D_2$, 19-nor-1,25-dihydroxy-21-epi-vitamin $D_3$, 1,25-dihydroxy-24-homo-22-dehydro-22E-vitamin $D_3$, and 19-nor-1,25-dihydroxy-24-homo-22-dehydro-22E-vitamin $D_3$, and nonsecosteroidal vitamin D mimics. In an additional example, the biologically active VDR agnoist is selected from the analogs represented by the following formula:

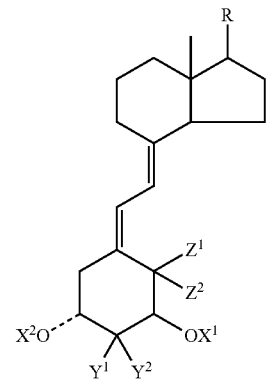

wherein $X^1$ and $X^2$ are each selected from the group consisting of hydrogen and acyl; wherein $Y^1$ and $Y^2$ can be H, or one can be O-aryl or O-alkyl while the other is hydrogen and can have a β or α configuration, $Z^1$ and $Z^2$ are both H, or $Z^1$ and $Z^2$ taken together are $CH_2$; and wherein R is an alkyl, hydroxyalkyl or fluoroalkyl group, or R may represent the following side chain:

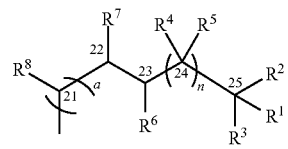

wherein (a) may have an S or R configuration and wherein $R^1$ represents hydrogen, hydroxy or O-acyl, $R^2$ and $R^3$ are each selected from the group consisting of alkyl, hydroxyalkyl and fluoroalkyl, or, when taken together represent the group —$(CH_2)m$—where m is an integer having a value of from 2 to 5, $R^4$ is selected from the group consisting of hydrogen, hydroxy, fluorine, O-acyl, alkyl, hydroxyalkyl and fluoroalkyl, $R^5$ is selected from the group consisting of hydrogen, hydroxy, fluorine, alkyl, hydroxyalkyl and fluoroalkyl, or, $R^4$ and $R^5$ taken together represent double-bonded oxygen, $R^6$ and $R^7$ taken together form a carbon-carbon double bond and $R^8$ may be H or $CH_3$, and wherein n is an integer having a value of from 1 to 5, and wherein the carbon at any one of positions 20, 22, or 23 in the side chain may be replaced by an O, S, or N atom.

In one example, the VDR agonists used in the methods provided herein do not cause symptoms of hypercalcemia when administered to a subject. In another example, the VDR agonists do not generate as much (i.e., a lesser degree) of a calcemic response as compared to calcitriol when administered to a subject. In one example, VDR agonists have low calcemic response characteristics as compared to calcitriol. In another embodiment, these compounds are selected from $1\alpha,25$-(OH)$_2$-24-epi-$D_2$, $1\alpha,25$-(OH)$_2$-24a-Homo-$D_3$, $1\alpha,25$-(OH)$_2$ 24a-Dihomo-$D_3$, $1\alpha,25$-(OH)$_2$-19-nor-$D_3$, and 20-epi-24-homo-$1\alpha,25$-(OH)$_2$-$D_3$. In another embodiment, the VDR agonist is calcipotriol or paricalcitol.

Other exemplary VDR agonists that can be used in the methods provided herein are provided in Table 1.
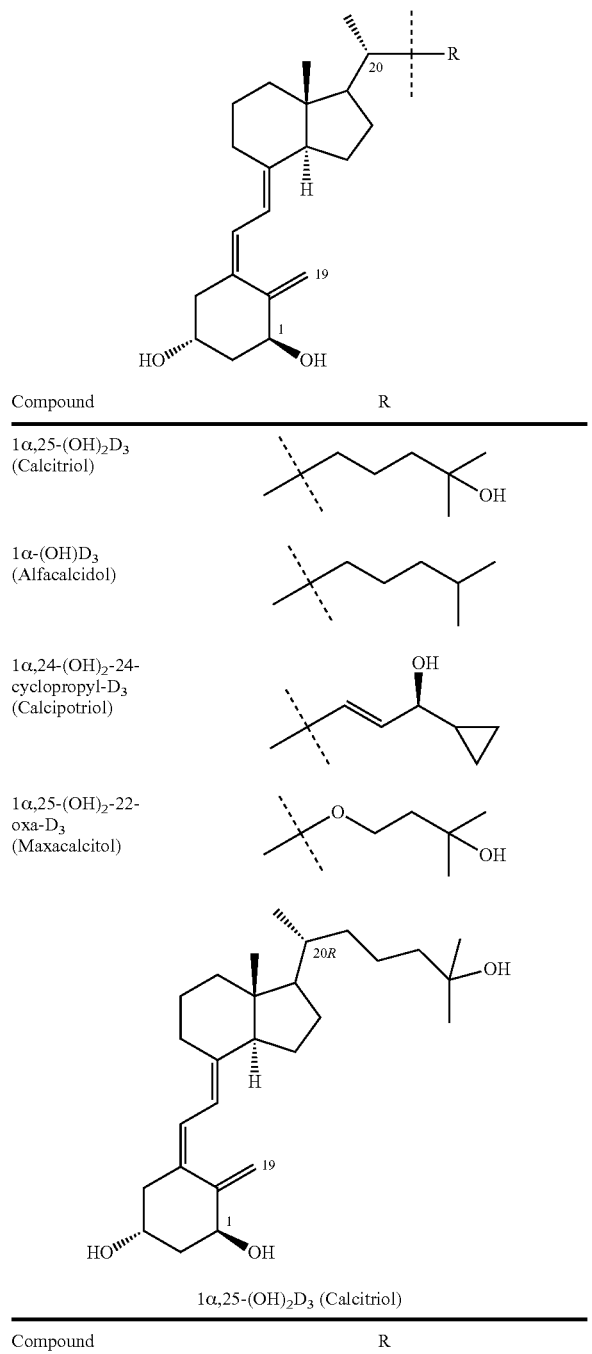
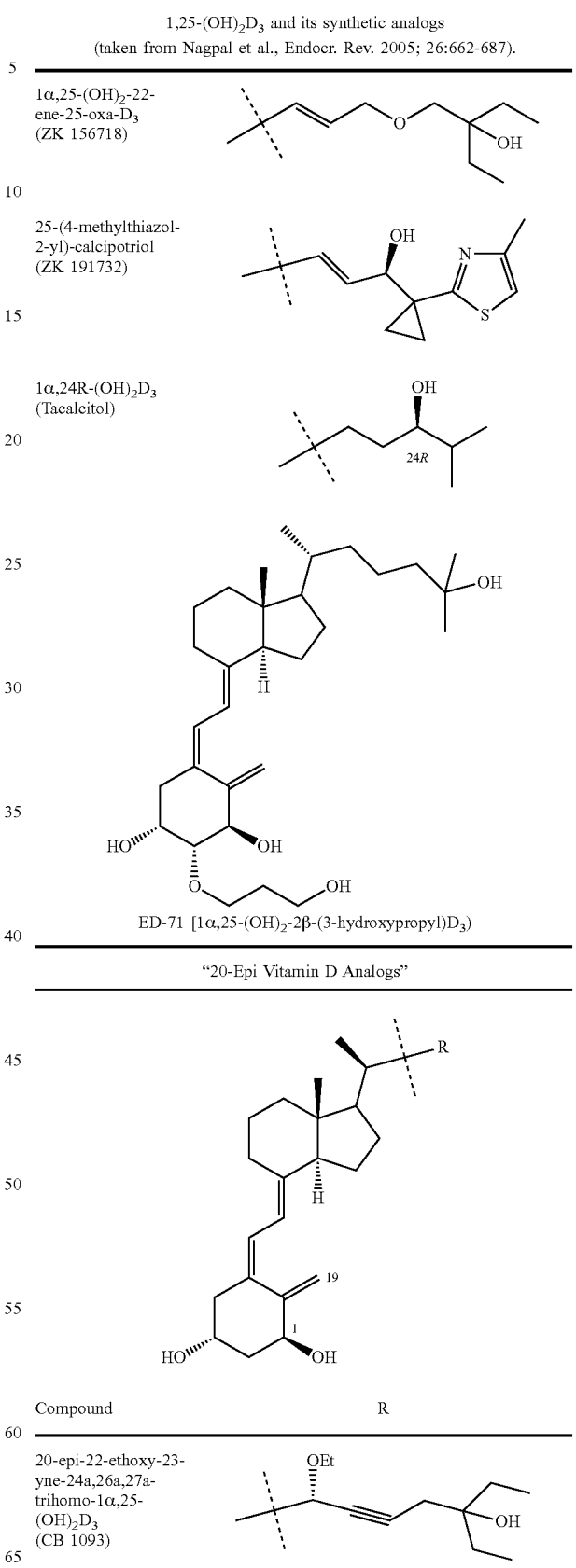

TABLE 1-continued 1,25-(OH)$_2$D$_3$ and its synthetic analogs
(taken from Nagpal et al., Endocr. Rev. 2005; 26:662-687).

1α-fluoro-25-(OH)-16,23E-diene-26,27,bishomo-20epi-cholecalciferol (Ro-26-6228, BXL-628, RS980400)

| Compound | R |
|---|---|
| 20-epi-1α,25-(OH)$_2$D$_3$ (KH 1060) | |

2-methylene-19-nor-(20S)-1α,25-(OH)$_2$D$_3$ (2MD)

In some examples the VDR agonist is used for treatment in combination with other therapeutic agents, such as one or more nuclear receptor ligands, including but not limited to ligands for peroxisome proliferator-activated receptor-gamma (PPAR-γ, NR1C3), peroxisome proliferator-activated receptor-alpha (PPAR-α, NR1C1) and peroxisome proliferator-activated receptor-delta (PPAR-δ, NR1C2), farnesoid x receptor (FXR, NR1H4), interferon-gamma (IFN-γ), angiotensin converting enzyme inhibitors, angiotensin II receptor antagonists, ursodeoxycholic acid (UDCA), curcumin, anti-oxidants including, but not limited to vitamin E, retinoids such as Vitamin A, and therapies that deliver proteases to the liver to degrade pathological ECM.

F. Incorporation of Vitamin D receptor agonists into Pharmaceuticals

The disclosed methods of treating cancer or treating/preventing pancreatitis include administering one or more VDR agonists, such as 1α,25(OH)$_2$ D$_3$, calcipotriol, paricalcitol, vitamin D precursors (for instance, 25-hydroxy-D$_3$ (25-OH-D$_3$) (calcidiol); vitamin D$_3$ (cholecalciferol); or vitamin D2 (ergocalciferol)), vitamin D analogs, and VDR agonist precursors to the subject in a pharmaceutically acceptable carrier and in an amount effective to inhibit (for example to relieve, cure, ameliorate, or prevent) the development, progression, or manifestation of pancreatitis in the subject. The present disclosure also contemplates the administration of a therapeutic composition comprising more than one VDR agonist, as well as VDR agonists in combination with other therapies (such as chemotherapy and/or biologic therapy to treat cancer as provided herein).

The vehicle in which the VDR agonist is delivered can include pharmaceutically acceptable compositions of the compounds, using methods well known to those with skill in the art. Any of the common carriers, such as sterile saline or glucose solution, can be utilized. The vehicle also can contain conventional pharmaceutical adjunct materials such as, for example, pharmaceutically acceptable salts to adjust the osmotic pressure, lipid carriers such as cyclodextrins, proteins such as serum albumin, hydrophilic agents such as methyl cellulose, detergents, buffers, preservatives and the like. A more complete explanation of parenteral pharmaceutical carriers can be found in Remington: *The Science and Practice of Pharmacy* (19th Edition, 1995) in chapter 95.

Embodiments of other pharmaceutical compositions can be prepared with conventional pharmaceutically acceptable carriers, adjuvants, and counter-ions, as would be known to those of skill in the art. The compositions in some embodiments are in the form of a unit dose in solid, semi-solid, and liquid dosage forms, such as tablets, pills, capsules, lozenges, powders, liquid solutions, or suspensions.

In some embodiments, sustained release of the pharmaceutical preparation that includes an effective amount of a VDR agonist is beneficial. Slow-release formulations are known to those of ordinary skill in the art. By way of example, sustained-release tablets can be formulated so that the active ingredient is embedded in a matrix of insoluble substance so that the dissolving drug emerges gradually through the holes in the matrix. In some formulations, the matrix physically swells to form a gel, so that the drug has first to dissolve in matrix, then exit through the outer surface.

In one example, a preferred dose of the VDR agonist for the present methods is the maximum that a patient can tolerate and not develop serious hypercalcemia. In one embodiment, the therapeutic administration of the VDR agonist compounds only causes mild hypercalcemia. In another example, the VDR agonists do not cause symptoms of hypercalcemia.

Therapeutically effective doses of vitamin D2 and D3 range, in some embodiments, from about 50 IU to about 50,000 IU. In some embodiments, for instance, vitamin D2 and/or D3 is administered in an oral dose of, for example, less than about 75 IU, about 100 IU, about 250 IU, about 500 IU, about 750 IU, about 1,000 IU, about 1,500 IU, about 2,000 IU, about 2,500 IU, about 5,000 IU, about 7,500 IU, about 10,000 IU, about 15,000 IU, about 20,000 IU, about 25,000 IU, about 40,000 IU, or about 50,000 IU, or more. In other embodiments, calcitriol is administered in a dose of from 0.001 to 10 micrograms. For instance, calcitrol is administered, in some embodiments, in a dose of about 0.01 µg, about 0.05 µg, about 0.1 µg, about 0.25 µg, about 0.5 µg, about 1 µg, about 5 µg, or about 10 µg. In one embodiment, the VDR agonist is calcipotriol administered at a dose of at least 1 µg/kg, at least 10 µg/kg, at least 25 µg/kg, at least 50 µg/kg, at least 60 µg/kg, or at least 100 µg/kg, such as 1 to 1000 µg/kg, 1 to 100 µg/kg, 1 to 75 µg/kg, 10 to 80 µg/kg, 30 to 75 µg/kg, or 50 to 70 µg/kg, such as 10 µg/kg, 20 µg/kg, 30 µg/kg, 40 µg/kg, 50 µg/kg, 60 µg/kg, 70 µg/kg, 80 µg/kg, 90 µg/kg, 100 µg/kg, 110 µg/kg or 120 µg/kg. In some examples, such doses of calcipotriol are administered by intraperitoneal or intravenous injection. In one embodiment, the VDR agonist is paricalcitol administered at a dose of at least 0.1 µg, at least 1 µg, at least 5 µg at least 10 µg, at least 20 µg, at least 50 µg, or at least 100 µg, such as 1 to 20 µg, 5 to 15 µg or 8 to 12 µg, such as 1 µg, 2 µg, 3 µg, 4 µg, 5 µg, 6 µg, 7 µg, 8 µg, 9 µg, 10 µg, 11 µg, 12 µg, 13 µg, 14 µg, 15 µg, 16 µg, 17 µg, 18 µg, 19 µg, or 20 µg. In some examples, such doses of calcipotriol are administered by intravenous injection 3 times weekly. In some embodiments, larger doses of VDR agonists are administered via a delivery route that targets the organ of interest, for instance the pancreas, liver, kidney, lung or prostate. Such targeting methods are described more fully below.

In certain embodiments, the VDR agonist is administered orally, for instance, in single or divided doses. For oral administration, the compositions are, for example, provided in the form of a tablet containing 1.0 to 1000 mg of the active ingredient, such as at least 75 IU, at least 100 IU, at least 250 IU, at least 500 IU, at least 750 IU, at least 800 IU, at least 1,000 IU, at least 1,500 IU, at least 2,000 IU, at least 2,500 IU, at least 5,000 IU, at least 7,500 IU, at least 10,000 IU, at least 15,000 IU, at least 20,000 IU, at least 25,000 IU, at least 40,000 IU, or 5 at least 0,000 IU per day, for example 50 IU to 2000 IU per day, 100 IU to 1000 IU per day, such as 800 IU per day, or more of the active ingredient for the symptomatic adjustment of the dosage to the subject being treated.

An effective parenteral dose could be expected to be lower, for example in the range of about 0.001 µg to about 10 µg, depending on the compound. Because the dosage and dosage regimen must be individually considered in the case of each subject according to sound professional judgment taking into account for example the age, body weight, general health, sex, diet, mode and time of administration, rate of excretion, drug combination, and severity of the condition of the host undergoing therapy, in some instances lower doses will be desirable, while in others larger doses will be required.

In another embodiment, if the VDR agonist is not a 1α-hydroxy compound, a daily dose between 1.0 and 100 µg per day per 160 pound patient is administered, such as between 5.0 and 50 µg per day per 160 pound patient. In a different embodiment, if the biologically active vitamin D compound is a 1α-hydroxy compound, a daily dose of between 0.1 and 20 µg per day per 160 pound patient is administered, while a preferred dose is between 0.5 and 10µ per day per 160 pound patient. In a particular example, the dose is between 3-10 µg per day.

In one example, the VDR agonists is cholecalciferol or calcidiol. In some examples, a higher dose than usual is administered, but with less frequency, for example, 50,000 to 500,000 units weekly.

The present disclosure also includes combinations of vitamin D receptor agonists with one or more other agents useful in the treatment of GLP-1 agonist induced pancreatitis. For example, in some embodiments, a VDR agonist is administered in combination with effective doses of other medicinal and pharmaceutical agents. In some embodiments, one or more known anti-pancreatitis drugs are included with the vitamin D receptor agonist.

The present disclosure also includes combinations of VDR agonists with one or more other agents useful in the treatment of cancer, such as a chemotherapeutic and/or biologic. For example, in some embodiments, a VDR agonist is administered in combination with effective doses of other medicinal and pharmaceutical chemotherapeutic and/or biologic agents (such as simultaneously, concurrently or one before the other). In some embodiments, one or more chemotherapeutic and/or biologic agent are included with the VDR agonist.

G. Exemplary Chemotherapies and Biologic Therapies

The disclosed methods of treating a cancer that has active stellate cells (such as those with CXCL12 activity) can use VDR agonists in combination with other therapeutic agents, such as chemotherapies and biotherapies. Chemotherapies and biotherapies can include anti-neoplastic chemotherapeutic agents, antibiotics, alkylating agents and antioxidants, kinase inhibitors, and other agents such as antibodies. Methods and therapeutic dosages of such agents are known to those skilled in the art, and can be determined by a skilled clinician. Other therapeutic agents, for example anti-tumor agents, that may or may not fall under one or more of the classifications below, also are suitable for administration in combination with the described VDR agonists. Selection and therapeutic dosages of such agents are known to those skilled in the art, and can be determined by a skilled clinician. For example, the chemotherapy and/or biologic used in the treatment in combination with one or more VDR agonists can be selected based on the cancer to be treated.

In one example, a chemotherapy or biotherapy increases killing of cancer cells (or reduces their viability). Such killing need not result in 100% reduction of cancer cells; for example a cancer chemotherapy that results in reduction in the number of viable cancer cells by at least 10%, at least 20%, at least 30%, at least 40%, at least 50%, at least 75%, at least 90%, or at least 95% (for example as compared to no treatment with the cancer chemotherapy or bio-therapy) can be used in the methods provided herein. For example, the cancer chemotherapy or bio-therapy can reduce the growth of cancer cells by at least 10%, at least 20%, at least 30%, at least 40%, at least 50%, at least 75%, at least 90%, or at least 95% (for example as compared to no chemotherapy or bio-therapy).

Particular examples of chemotherapeutic agents that can be used include alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; folic acid (for example, methotrexate, pemetrexed, and raltitrexed), purine (for example, cladribine, clofarabine, fludarabine, mercaptopurine, and tioguanine), pyrimidine (for example, capecitabine), cytarabine, fluorouracil, and gemcitabine; plant alkaloids, such as podophyllum (for example, etoposide, and teniposide); microtubule binding agents (such as paclitaxel, docetaxel, vinblastine, vindesine, vinorelbine (navelbine) vincristine, the epothilones, colchicine, dolastatin 15, nocodazole, podophyllotoxin, rhizoxin, and derivatives and analogs thereof), DNA intercalators or cross-linkers (such as cisplatin, carboplatin, oxaliplatin, mitomycins, such as mitomycin C, bleomycin, chlorambucil, cyclophosphamide, and derivatives and analogs thereof), DNA synthesis inhibitors (such as methotrexate, 5-fluoro-5'-deoxyuridine, 5-fluorouracil and analogs thereof); anthracycline family members (for example, daunorubicin, doxorubicin, epirubicin, idarubicin, mitoxantrone, and valrubicin); antimetabolites, such as cytotoxic/antitumor antibiotics, bleomycin, rifampicin, hydroxyurea, and mitomycin; topoisomerase inhibitors, such as topotecan and irinotecan; photosensitizers, such as aminolevulinic acid, methyl aminolevulinate, porfimer sodium, and verteporfin, enzymes, enzyme inhibitors (such as camptothecin, etoposide, formestane, trichostatin and derivatives and analogs thereof), kinase inhibitors (such as imatinib, gefitinib, and erolitinib), gene regulators (such as raloxifene, 5-azacytidine, 5-aza-2'-deoxycytidine, tamoxifen, 4-hydroxytamoxifen, mifepristone and derivatives and analogs thereof); and other agents, such as alitretinoin, altretamine, amsacrine, anagrelide, arsenic trioxide, asparaginase, axitinib, bexarotene, bevacizumab, bortezomib, celecoxib, denileukin diftitox, estramustine, hydroxycarbamide, lapatinib, pazopanib, pentostatin, masoprocol, mitotane, pegaspargase, tamoxifen, sorafenib, sunitinib, vemurafinib, vandetanib, and tretinoin.

In one example, a bio-therapy includes or consists of an antibody, such as a humanized antibody. Such antibodies can be polyclonal, monoclonal, or chimeric antibodies. As noted above, methods of making antibodies specific for a particular target is routine. In some example, the therapeutic antibody is conjugated to a toxin. Exemplary biotherapies include alemtuzumab, bevacizumab, cetuximab, gemtuzumab, rituximab, panitumumab, pertuzumab, and trastuzumab.

Other examples of bio-therapy include inhibitory nucleic acid molecules, such as an antisense oligonucleotide, a siRNA, a microRNA (miRNA), a shRNA or a ribozyme. Any type of antisense compound that specifically targets and regulates expression of a target nucleic acid is contemplated for use. An antisense compound is one which specifically hybridizes with and modulates expression of a target nucleic acid molecule. These compounds can be introduced as single-stranded, double-stranded, circular, branched or hairpin compounds and can contain structural elements such as internal or terminal bulges or loops. Double-stranded antisense compounds can be two strands hybridized to form double-stranded compounds or a single strand with sufficient self complementarity to allow for hybridization and formation of a fully or partially double-stranded compound. In some examples, an antisense oligonucleotide is a single stranded antisense compound, such that when the antisense oligonucleotide hybridizes to a target mRNA, the duplex is recognized by RNaseH, resulting in cleavage of the mRNA. In other examples, a miRNA is a single-stranded RNA molecule of about 21-23 nucleotides that is at least partially complementary to an mRNA molecule that regulates gene expression through an RNAi pathway. In further examples, a shRNA is an RNA oligonucleotide that forms a tight hairpin, which is cleaved into siRNA. siRNA molecules are generally about 20-25 nucleotides in length and may have a two nucleotide overhang on the 3' ends, or may be blunt ended. Generally, one strand of a siRNA is at least partially complementary to a target nucleic acid. Antisense compounds specifically targeting a gene can be prepared by designing compounds that are complementary to a target nucleotide sequence, such as a mRNA sequence. Antisense compounds need not be 100% complementary to the target nucleic acid molecule to specifically hybridize and regulate expression of the target. For example, the antisense compound, or antisense strand of the compound if a double-stranded compound, can be at least 75%, at least 80%, at least 85%, at least 90%, at least 95%, at least 99% or 100% complementary to a target nucleic acid sequence. Methods of screening antisense compounds for specificity are well known (see, for example, U.S. Publication No. 2003-0228689). In addition, methods of designing, preparing and using inhibitory nucleic acid molecules are within the abilities of one of skill in the art.

H. Routes of Administration

It is not intended that the present disclosure be limited to a particular mode of administering the VDR agonists, chemotherapies and biotherapies. A variety of modes of administration are contemplated, including intravenously, intramuscularly, subcutaneously, intradermally, intraperitoneally, intrapleurally, intrathecally, orally, rectally, transdermally, by inhalation, and topically. In certain embodiments, the therapeutic compositions are administered via suppository, or in tablet or capsule formulations for oral delivery. In one embodiment, administration of the therapeutic compositions occurs at night. In another embodiment, multiple doses (e.g., 3 or 4) are provided in a 24 hour period. In a further embodiment, the administration of the therapeutic composition is by pulse intravenous therapy. In one example, the therapeutic compositions are administered via a transdermal patch (skin patch).

For instance a VDR agonist, chemotherapy and/or biotherapy is administered, in one embodiment, intravenously in any conventional medium for intravenous injection, such as an aqueous saline medium, or in blood plasma medium. In other embodiments, administration is oral, for instance as a liquid or a pill. In other embodiments, administration is rectal, for example via a suppository containing the VDR agonist, chemotherapy and/or biotherapy. In still other embodiments, administration is by direct infusion into an artery of the lung, kidney, pancreas, prostate, or liver with a pharmaceutical composition that contains a VDR agonist, chemotherapy and/or biotherapy. In yet other embodiments, a target delivery technology is used to deliver the composition to the target tissue, for instance the lung, kidney, pancreas, prostate, or liver. In one specific, non-limiting example, the VDR agonist, chemotherapy and/or biotherapy is designed to be taken up by the target tissue, or is linked to a target-specific carrier molecule that facilitates uptake by the target cells. For instance, for stellate cells, the VDR agonist can be conjugated to a receptor for low- and/or high-density lipoproteins (LDL and/or HDL receptors).

The present disclosure also provides a transdermal patch that includes a therapeutic composition comprising a VDR agonist, chemotherapy and/or biotherapy. In one embodiment, the transdermal patch includes a therapeutically effective amount of a VDR agonist, chemotherapy and/or biotherapy. In another embodiment, the transdermal patch further includes a single polymer or multiple polymers. In one example, the transdermal patch further includes a polyurethane acrylic copolymer. In one embodiment, the transdermal patch further includes silicone or polyisobutylene or both. In one embodiment, the transdermal patch is worn by a subject at risk for developing GLP-1 agonist induced pancreatitis. In another embodiment, the transdermal patch is worn by a subject with symptoms of GLP-1 agonist induced pancreatitis. In another embodiment, the transdermal patch delivers a VDR agonist to a subject in a continuous manner under conditions such that symptoms of GLP-1 agonist induced pancreatitis are reduced. In one embodiment, the transdermal patch is worn by a subject having a cancer of the lung, kidney, pancreas, prostate, or liver.

Pharmaceutical compositions of VDR agonist, chemotherapy and/or biotherapy according to the present disclosure can be administered at about the same dose throughout a treatment period, in an escalating dose regimen, or in a loading-dose regime (for instance, in which the loading dose is about two to five times the maintenance dose). In some embodiments, the dose is varied during the course of a treatment based on the condition of the subject being treated, the severity of the disease or condition, the apparent response to the therapy, and/or other factors as judged by one of ordinary skill in the art. In some embodiments long-term treatment with the drug is contemplated, for instance in order to prevent or reduce the re-occurrence of GLP-1 agonist induced pancreatitis in a subject.

Example 1

Experimental Procedures

Cell Lines

The human pancreatic cancer cell lines MiaPaCa-2 (CRL-1420), BxPC-3 (CRL-1687), HPAC (CRL-2119), Panc1 (CRL-1469), and AsPC1 (CRL-1682) were acquired from ATCC and cultured according to supplier's instructions. The mouse pancreatic cancer cell lines p53 2.1.1, p53 4.4, and Ink 2.2 were derived from PDA in LSL-$Kras^{G12D/+}$; $Trp53^{lox/lox}$; Pdx1-Cre mice or LSL-$Kras^{G12D}$; $Ink4\alpha/Arf^{lox/lox}$; Pdx1-Cre mice (Bardeesy et al., 2006; Collisson et al., 2011) and cultured as described previously (Collisson et al., 2011; Collisson et al., 2012). The spontaneously immortalized human pancreatic stellate cell line hPSC was isolated and established from a pancreatic cancer patient after surgical resection, as previously described (Mantoni et al., 2011).

Primary Pancreatic Stellate Cell Isolation and Culture

Mouse PSC Isolation

Pancreatic stellate cells (PSCs) were isolated from pancreata of wild-type C57BL6/J mice at 8 weeks of age by a modification of the method described by Apte et al. (Apte et al., 1998). Briefly, pancreatic tissue was minced with scissors and digested with 0.02% Pronase (Roche, Indianapolis, Ind.), 0.05% Collagenase P (Roche), and 0.1% DNase (Roche) in Gey's balanced salt solution (GBSS; Sigma Aldrich, St. Louis, Mo.) at 37° C. for 20 mM Digested tissue was then filtered through a 100 μm nylon mesh. Cells were washed once with GBSS, pelleted, and resuspended in 9.5 ml GBSS containing 0.3% bovine serum albumin (BSA) and 8 ml 28.7% Nycodenz solution (Sigma Aldrich; approximate density of the solution is 1.070). The cell suspension was layered beneath GBSS containing 0.3% BSA, and centrifuged at 1400×g for 20 min at 4° C. The cells of interest were harvested from the interface of the Nycodenz solution at the bottom and the aqueous solution at the top. Isolated PSCs were washed with GBSS and resuspended in DMEM (Invitrogen) containing 10% characterized FBS (HyClone) and antibiotics (penicillin 100 U/ml and streptomycin 100 μg/ml, Invitrogen). Cells were maintained at 37° C. in a humidified atmosphere of 7% $CO_2$. After reaching 80% confluence, cells were briefly trypsinized (0.25% Trypsin-EDTA, Invitrogen) and subcultured.

Human PSC Isolation

Pancreatic stellate shaped cells were isolated by a modification of the method described by Schafer et al. in the liver (Schafer et al., 1987). Briefly, pancreatic tissue from human pancreatic cancers was minced with scissors, and digested with 0.02% pronase, 0.05% collagenase P, and 0.1% DNase for 20 minutes at 37° C. Tissue pieces were washed and resuspended in 9.5 ml Gey's balanced salt solution (GBSS). After a second wash, tissue pieces were resuspended in Iscove's modified Dulbecco's medium containing 10% fetal calf serum, 4 mM glutamine, and antibiotics (penicillin 100 units/ml; streptomycin 100 μg/ml), seeded in plastic six well culture plates in Dulbecco's medium with fetal calf serum, glutamine, and antibiotics as detailed above, and allowed to adhere overnight. The tissue was maintained at 37° C. in a humidified atmosphere of 5% $CO_2$/95% air, and maintained until stellate cells emerged (three to five weeks to reach 60-80% confluence). The tissue pieces were removed when the PSCs were about 20% confluent. The medium was replenished once weekly, and cells were grown to 80% confluence before being harvested and frozen down in liquid nitrogen.

Animals

LSL-$Kras^{G12D/+}$;LSL-$Trp53^{R172H/+}$;Pdx-1-Cre (KPC) mice were described previously (Hingorani et al., 2005), as were $Vdr^{-/-}$ mice (Yoshizawa et al., 1997).

RNA-Seq

Total RNA from human and mouse PSCs was isolated using Trizol (Invitrogen) and the RNeasy mini kit with on-column DNase digestion (Qiagen) according to the manufacturers' instructions. Biological quadruplicates were used for human samples, and biological triplicates used for mouse samples. For transcriptome studies with VDR activation, PSCs were treated with vehicle (DMSO) or 100 nM calcipotriol (Tocris) and harvested at the indicated time points. Sequencing libraries were prepared from 100-500 ng total RNA using the TruSeq RNA Sample Preparation Kit v2 (Illumina) according to the manufacturer's protocol. The Gene Expression Omnibus accession number for the RNA-Seq data is GSE43770.

Quantitative RT-PCR

Total RNA was purified following Trizol extraction according to the manufacturer's instructions. cDNA synthesis was carried out using iScript reagent (Bio-Rad), and qRT-PCR performed using SsoAdvanced SYBR Green reagent on the CFX384 detection system (Bio-Rad). Relative expression values were determined using the standard curve method. Primer sequences can be found in Table 2.

TABLE 2

Primer sequences

| Gene | | Forward primer sequence | SEQ ID NO: | Reverse primer sequence | SEQ ID NO: |
|---|---|---|---|---|---|
| Mouse/ Human | 36b4 | GTGCTGATGGGCAAG AAC | 1 | AGGTCCTCCTTGGTG AAC | 34 |
| Mouse | Vdr | GCTGAACCTCCATGA GGAAG | 2 | GGATCATCTTGGCGT AGAGC | 35 |
| | Ccl2 | CCCAATGAGTAGGCT GGAGA | 3 | TCTGGACCCATTCCT TCTTG | 36 |
| | Col1a1 | ACGCATGGCCAAGAA GAC | 4 | GGTTTCCACGTCTCA CCATT | 37 |
| | Cxcl13 | CAGAATGAGGCTCAG CACAG | 5 | TTGTGTAATGGGCTT CCAGA | 38 |

TABLE 2-continued

Primer sequences

| Gene | Forward primer sequence | SEQ ID NO: | Reverse primer sequence | SEQ ID NO: |
| --- | --- | --- | --- | --- |
| Il6 | TTCTCTGGGAAATCGTGGAAA | 6 | TGCAAGTGCATCATCGTTGT | 39 |
| Wnt2b | GCTGCTGCTGCTACTCCTGA | 7 | GCTCCCAGAGCCCCTATGTA | 40 |
| Wnt9a | CGAGTGGACTTCCACAACAA | 8 | GCAAGTGGTTTCCACTCCAG | 41 |
| Mmp2 | GATGTCGCCCCTAAAACAGA | 9 | GGGCAGCCATAGAAAGTGTT | 42 |
| Idi1 | TTGGGAATACCCTTGGAAGA | 10 | CATGTTCACCCCAGATACCA | 43 |
| Nsdh1 | GCAAGCTGAGGTCGATCATT | 11 | TGGCTCAAAGTATGGTTTCGT | 44 |
| Insig1 | ATCTTCTCCTCCGCCTGGT | 12 | TGGTTCTCCCAGGTGACTGT | 45 |
| Acta2 | TGACAGGATGCAGAAGGAGA | 13 | CCACCGATCCAGACAGAGTA | 46 |
| Prss3 | TCTGTCCCCTACCAGGTGTC | 14 | GTTGGGGTGCTTGATGATCT | 47 |
| Ins2 | TTTGTCAAGCAGCACCTTTG | 15 | TCTACAATGCCACGCTTCTG | 48 |
| Krt19 | ACCCTCCCGAGATTACAACC | 16 | GGCGAGCATTGTCAATCTGT | 49 |
| Cdkn1a | ACTACCAGCTGTGGGGTGAG | 17 | GGACATCACCAGGATTGGAC | 50 |
| Has2 | CGGAGGACGAGTCTATGAGC | 18 | CTGTGATTCCGAGGAGGAGA | 51 |
| Cyp24a1 | CCAGCGGCTAGAGATCAAAC | 19 | CACGGGCTTCATGAGTTTCT | 52 |
| Col1a2 | CCGTGCTTCTCAGAACATCA | 20 | CTTGCCCCATTCATTTGTCT | 53 |
| Shh | CTGGCCAGATGTTTTCTGGT | 21 | CTCGGCTACGTTGGGAATAA | 54 |
| Pkm2 | TGTCTGGAGAAACAGCCAAG | 22 | TCCTCGAATAGCTGCAAGTG | 55 |
| Ccnb1 | ATCGGGGAACCTCTGATTTT | 23 | GGCTTGGAAGCAGCAGTAAC | 56 |
| Tnfa | CGAGTGACAAGCCTGTAGCC | 24 | AGCTGCTCCTCCACTTGGT | 57 |
| B2M | GGTCTTTCTGGTGCTTGTCT | 25 | TATGTTCGGCTTCCCATTCT | 58 |
| Des | CGAGCTCTACGAGGAGGAGA | 26 | GAAGGCAGCCAAGTTGTTCT | 59 |
| Thbs1 | GACTCGGGACCCATCTATGA | 27 | GGGGTTTCTCTAGCCCTTGT | 60 |
| Ctgf | AGAGTGGAGCGCCTGTTCTA | 28 | GACAGGCTTGGCGATTTTAG | 61 |
| Postn | CCTGCAAATGCCAACAGTTA | 29 | TTTCTTCCCGCAGATAGCAC | 62 |
| Fabp4 | GATGGTGACAAGCTGGTGGT | 30 | AATTTCCATCCAGGCCTCTT | 63 |

TABLE 2-continued

Primer sequences

| | Gene | Forward primer sequence | SEQ ID NO: | Reverse primer sequence | SEQ ID NO: |
|---|---|---|---|---|---|
| | Cda | TCAGCCTACTGCCCCTACAG | 31 | GAGATGGCAATAGCCCTGAA | 64 |
| | Dck | GACAAACACGAAAGCCTGGT | 32 | TCAAGCAATGGCAGTACACA | 65 |
| | Amy2a | CATCTGTTTGAATGGCGATG | 33 | TTCCCACCAAGGTCTGAAAG | 66 |
| Human | ACTA2 | CGATGCTCCCAGGGCTGTTT | 67 | TTCGTCACCCACGTAGCTGTCTTT | 87 |
| | CXCL1 | GAAAGCTTGCCTCAATCCTG | 68 | CACCAGTGAGCTTCCTCCTC | 88 |
| | CSF2 | CAGCCACTACAAGCAGCACT | 69 | AAGGGGATGACAAGCAGAAA | 89 |
| | AURKB | GGGAGAGCTGAAGATTGCTG | 70 | GCACCACAGATCCACCTTCT | 90 |
| | WNT2B | ACATAATAACCGCTGTGGTCGCAC | 71 | TGGCACTTACACTCCAGCTTCAGA | 91 |
| | JAG1 | CCCCTAAGCCTCCTGCTC | 72 | GCATGGACAGGATCTCCAAC | 92 |
| | MMP2 | CCAAGTGGGACAAGAACCAGATCA | 73 | GTCCAGATCAGGTGTGTAGCCAAT | 93 |
| | COL1A1 | ACAGCCGCTTCACCTACAGC | 74 | CGGTGTGACTCGTGCAGC | 94 |
| | COL3A1 | AGAGGGGCTCCTGGTGAG | 75 | GCAGTTCCAGGAGGACCAG | 95 |
| | IDI1 | TGATCACCATTGGCTGGGAAGGAA | 76 | GCTGCCACAAACCTCCACTTTGTA | 96 |
| | NSDHL | TTGCGAGCTGAGGCCAGACA | 77 | AAACTCCTGTGACTCTGCTGATGAGG | 97 |
| | INSIG1 | TTTCCTCCGCCTGGTGGGT | 78 | GTTCTCCGAGGTGACTGTCGATACA | 98 |
| | IL6 | AAAGAGGCACTGGCAGAAAA | 79 | AGCTCTGGCTTGTTCCTCAC | 99 |
| | CCL2 | GCCTCCAGCATGAAAGTCTC | 80 | CACTTGCTGCTGGTGATTCT | 100 |
| | HAS2 | ACAGACAGGCTGAGGACGAC | 81 | GCTGTGATTCCAAGGAGGAG | 101 |
| | HAS2 promoter | ACGTCGGAATTGGCTCTG | 82 | CAGATAGGAGCGGGAGGAG | 102 |
| | COL1A1 promoter | ACATGGAAAAGCCTTGATGG | 83 | GCAGCAGTCTGGAAGGTAGG | 103 |
| | VDR | ACTTGCATGAGGAGGAGCAT | 84 | TCGGCTAGCTTCTGGATCAT | 104 |
| | CYP24A1 | CCAGCGATAATACGCCTCA | 85 | ACCCTGTAGAATGCCTTGGA | 105 |
| | THBS1 | GGGAAGAAAATCATGGCTGA | 86 | CAGAAGGTGCAATACCAGCA | 106 |

Lipid Droplet Accumulation Assay

Primary human CAPSCs were seeded onto glass coverslips. After overnight attachment, cells were treated with vehicle (DMSO) or 100 nM calcipotriol for 48 h. Media was aspirated, cells were washed twice with PBS (Gibco) and fixed in 10% buffered formalin at room temperature for 15 minutes. Fixative was removed and cells were washed three times with PBS. Cells were then stained with 1 µg/ml 4,4-Difluoro-1,3,5,7,8-Pentamethyl-4-Bora-3a,4a-Diaza-s-Indacene (BODIPY 493/503, Molecular Probes) for 1 h at room temperature, protected from light. Dye was removed and cells were washed three times with PBS, then mounted using Vectastain mounting medium (Vector Labs). Fluorescence was visualized through the GFP filter on a Leica DM5000B fluorescent microscope and quantification performed using ImageJ.

Conditioned Media Experiments

Primary CAPSCs were grown to 100% confluency. Fresh media was added to the cultures, and at this time, CAPSCs were treated with 100 nM calcipotriol. After 48 h, conditioned media was harvested, sterile-filtered through 0.45 µm pores, and added to pancreatic cancer cells (PCCs) at 50-60% confluency. PCCs were treated directly with 100 nM calcipotriol at the onset of conditioned media incubation. After 48 h, PCCs were harvested and RNA and protein isolated for analysis.

In Vitro Viability Assay

MiaPaCa-2 cells were seeded into 96-well plates (1×104 cells/well) in DMEM+10% FBS. After incubation overnight, cells were washed and medium was changed to DMEM+10% FBS, with or without 100 nM calcipotriol; or CAPSC conditioned media (CM), from CAPSC incubated with or without 100 nM for 48 h prior to CM collection. Cells were incubated for 24 h, then treated with the indicated doses of gemcitabine (Sigma) or vehicle alone. After 48 h, viability was measured using the CellTiter-Glo luminscence-based viability assay (Promega) according to the manufacturer's instructions. Experiments were done in triplicate.

Orthotopic Transplant/Allograft Model

The orthotopic transplant model used was described previously (Collisson et al., 2012). Briefly, $1 \times 10^3$ p53 2.1.1 cells were orthotopically injected into 6-8 week old FVB/n mice in 50% Matrigel. After bioluminescent imaging on day 7, mice were randomized into one of four treatment groups: saline, calcipotriol (60 µg/kg i.p., QDX20), gemcitabine (20 mg/kg i.p., Q3DX4), or calcipotriol+gemcitabine. For combination-treated mice, calcipotriol treatment began on day 7 and gemcitabine treatment began on day 14. Mice were euthanized on day 26 or when distressed, and pancreata were harvested, sliced, and flash frozen in liquid nitrogen or immediately fixed in formalin.

PH3 Quantification

Pancreata were fixed overnight in zinc-containing neutral-buffered formalin (Anatech Ltd.), embedded in paraffin, cut into 5 µm sections and placed onto Superfrost Plus slides (Fisher Scientific). Following citrate mediated antigen retrieval in a pressure cooker, endogenous peroxidases were quenched in 3% H2O2/PBS for 15 minutes. Sections were deparaffinized and hydrated through a xylenes/ethanol series. The remaining steps were carried out using the Vectastain Elite ABC staining kit (Vector Labs). Primary antibody was used at 1:100 (Cell Signaling Technology). Slides were counterstained with hematoxylin. Six 200× images were captured and scored per tumor (n=5) on a Zeiss Axio Imager.M2 microscope. Images were acquired using Nuance 3.0.1.2 multispectral imaging software, and positive cells were identified and scored using inForm 1.4.0 Advanced Image Analysis software (PerkinElmer).

KPC Study Design

KPC mice with pancreatic ductal adenocarcinoma were used based on tumor size, as described previously (Olive et al., 2009). In this study, enrollment was restricted to mice with tumors of a mean diameter between 6 and 9 mm, as determined by high resolution ultrasound imaging. Suitable mice were assigned to a treatment group: gemcitabine; calcipotriol; or gemcitabine and calcipotriol combination. Gemcitabine was administered as a saline solution at 100 mg/kg by intraperitoneal injection, once every three days; when appropriate, a final dose was given two hours prior to euthanasia. Calcipotriol was administered as a saline solution daily at 60 µg/kg by intraperitoneal injection. Mice were euthanized after nine days of treatment or at the onset of clinical signs such as abdominal ascites, severe cachexia, significant weight loss or inactivity. Tumors were imaged by high resolution ultrasound up to twice during the nine day treatment study.

Imaging and Quantification of KPC Tumors

High resolution ultrasound imaging of mouse pancreas was carried out using a Vevo 770 system with a 35 MHz RMV scanhead (Visual Sonics, Inc.) as described previously (Dowell and Tofts, 2007). Serial 3D images were collected at 0.25 mm intervals. Tumors were outlined on each 2D image and reconstructed to measure the 3D volume using the integrated Vevo 770 software package.

Quantification of Intratumoral dFdC, dFdU, and dFdCTP by LC-MS/MS

LC-MS/MS was performed as described by Bapiro et al. (Bapiro et al., 2011). Weighed tumor samples (10 mg) were homogenized in 200 µl ice-cold 50% acetonitrile (v/v) containing 25 µg/ml tetrahydrouridine (Millipore). Homogenization was performed in 2 30-second pulses at 3000 rpm in ceramic bead tubes in a PowerLyzer 24 (MO BIO Laboratories, Inc.). After short-term storage at −80° C., samples were thawed on ice and further homogenized with a single 3-second pulse in a Sonic Dismembrator 550 ultrasonic homogenizer (Fisher Scientific) set to power level 2. 50 µl of tissue homogenate was then combined with 200 µl of ice-cold acetonitrile (50%, v/v) containing internal standards [$^{13}C_9{}^{15}N_3$ CTP (50 ng/ml; Sigma); $^{13}C^{15}N_2$ dFdC (25 ng/ml; Toronto Research Chemicals); $^{13}C^{15}N_2$ dFdU (50 ng/ml; Toronto Research Chemicals)], vortexed, and centrifuged at 15,000 rpm for 25 min. 200 µl of supernatant was dried down, resuspended in 100 µl water, and 15 µl injected onto a Hypercarb column (100×2.1 ID, 5 µm; Thermo Fisher Scientific) fitted with a Hypercarb guard column (10×2.1, 5 µm; Thermo Fisher Scientific). Analytes were separated using a gradient of acetonitrile in 10 mM ammonium acetate, pH 10 and detected using a Thermo LTQ-XL mass spectrometer (Thermo Fisher Scientific). Drugs recoveries were normalized using the internal standards and quantified using calibration standards generated from untreated tissue homogenates as described (Bapiro et al., 2011).

Immunohistochemistry

Tumors harvested from treated KPC mice were immediately fixed in buffered formalin. Fixed tissues were embedded in paraffin and cut into 5 µm sections. Antigen retrieval was performed using 10 mM citric acid, pH 6.0 in a pressure cooker to unmask CC3, or using 10 mM EDTA, pH 8.0 in a pressure cooker to unmask CD31. Endogenous peroxidases were quenched using 3% H2O2 in methanol. Immunohistochemical staining for CC3 (primary antibody 1:100, Cell Signaling Technology) or for CD31 (primary antibody 1:100, Santa Cruz Biotechnology) was performed using the Vectastain ABC kit as described above. Six 400× fields were captured per tumor (gemcitabine: n=4, calcipotriol: n=7, gemcitabine+calcipotriol: n=7) on a Zeiss Axio Imager.M2 microscope using Nuance 3.0.1.2 multispectral analysis software. CD31-positive area was quantified in each section using Nuance software. For CC3 quantification, sections stained with hematoxylin alone were used to train inForm 1.4.0 Advanced Image Analysis software to distinguish tumor from stroma. Total tumor cells were quantified per field, as well as total and percent CC3-positive tumor cells per field. Data are plotted as percent CC3-positive cells due to variability of total tumor cell number per field.

Immunostaining
Mouse Pancreas

Tissues were embedded in O.C.T. and frozen sections were fixed in ice-cold methanol at −20° C. for 20 min. Sections were blocked in PBS+0.2% BSA+0.05% Triton X-100 (blocking solution) for 1 h at room temperature. Primary antibody dilutions in blocking solution were as follows: anti-phospho-STAT3(Tyr705), 1:100 (Cell Signaling Technology); anti-Collagen I, 1:500 (Abcam), anti-GFAP, 1:100 (Abcam); anti-CD45, 1:100 (BD Pharmingen). Primary antibody incubations were performed in a humidified chamber at 4° C. overnight. Sections were washed 3 times with PBS+0.05% Triton X-100, then incubated in secondary antibodies for 1 h at room temperature, protected from light. Secondary antibodies used included Alexa Fluor 594 goat anti-rabbit IgG, Alexa Fluor 488 goat anti-rabbit IgG, Alexa Fluor 594 goat anti-rat IgG, and Alexa Fluor 488 goat anti-mouse IgG (Molecular Probes) and were used at 1:250 in blocking solution. Sections were washed 3 times with PBS and mounted using Vectastain mounting medium with or without DAPI. Fluorescence was visualized on a Leica DM5000B fluorescent microscope and quantified using ImageJ.

Human PDA
1) Immunohistochemical Staining

The pancreas tissues were removed from patients undergoing operation for PDA, and fixed by immersing in 4% paraformaldehyde overnight at 4° C. The specimens were embedded in regular paraffin wax and cut into 4-µm sections Immunohistochemical staining for VDR was performed using an avidin-biotin-peroxidase complex detection kit (VECTASTAIN Elite ABC Rat IgG Kit; Vector Laboratories). Briefly, tissue sections were deparaffinized and rehydrated in PBS. Following antigen retrieval with the target retrieval solution (Dako, Glostrup, Denmark), endogenous peroxidase activity was blocked by incubation with 0.3% hydrogen peroxide. After immersion in diluted normal rabbit serum, the sections were incubated with rat anti-VDR antibody (at 1:100 dilution; Abcam) overnight at 4° C. The slides were incubated with biotinylated rabbit anti-rat IgG antibody, followed by biotinylated enzyme-conjugated avidin. Finally, the color was developed by incubating the slides for several minutes with diaminobenzidine (Dojindo, Kumamoto, Japan).

2) Immunofluorescent Staining

Tissue sections were deparaffinized and rehydrated in PBS. Following antigen retrieval with the target retrieval solution, the slides were blocked with 3% BSA and incubated with rabbit anti-α-SMA antibody (at 1:200 dilution; Abcam) and rat anti-VDR antibody (at 1:100 dilution) overnight at 4° C. After washing, the slides were incubated for 1 h with Alexa Fluor$^{546}$-labeled donkey anti-rabbit IgG antibody (at 1:200 dilution; Invitrogen) and Alexa Fluor$^{488}$-labeled goat anti-rat IgG antibody (at 1:200 dilution; Invitrogen). After washing, the slides were analyzed for fluorescence using an all-in-one type fluorescent microscope (BioZero BZ-9000; Keyence, Osaka, Japan). Nuclear counterstaining was performed using DAPI.

siRNA

VDR knockdowns were performed in CAPSCs using the ON-TARGETplus VDR siRNA SMARTpool (Dharmacon) alongside a non-targeting control. Cells were transfected with siRNA pools using the DharmaFECT1 reagent according to the manufacturer's instructions. Calcipotriol treatments were initiated 24 h post-transfection, and cells were harvested after 48 h treatments (72 h post-transfection).

Gene Expression Analysis in Pancreas Tissue Subtypes
Laser Capture Microdissection Pancreata were harvested from wild-type C57BL/6J mice at 8 weeks of age and immediately embedded in O.C.T. and frozen. A piece of each pancreas was reserved for PSC isolation (below). Tissues were cut at 5 µm thickness, fixed and hydrated through an ethanol series, stained with H&E, then cleared through an ethanol series and xylenes. Sections were dessicated completely, then imaged and microdissected using the MMI CellCut Laser Capture Microdissection system. Acini, ducts, and islets were identified and microdissected from ~10-20 sections per animal (n=5).

Gene Expression Analysis qRNA was extracted from the laser captured samples described above, and from PSCs derived from the same animals by density centrifugation as clean laser capture of these cells proved difficult. RNA samples (20 ng) were reverse-transcribed using the ABI High-Capacity RT Kit. Due to low yield, cDNA samples were then subject to preamplification using the Taqman PreAmp Master Mix Kit (Life Technologies) per manufacturer's instructions, using the appropriate primer pairs followed by digestion of primer oligonucleotides with ExoI (NEB). Preamplified cDNA was then used for qRT-PCR for Vdr and the appropriate control genes.

RNA-Seq
Sample Preparation

Briefly, mRNA was purified, fragmented, and used for first-, then second-strand cDNA synthesis followed by adenylation of 3' ends. Samples were ligated to unique adapters and subject to PCR amplification. Libraries were then validated using the 2100 BioAnalyzer (Agilent), normalized, and pooled for sequencing. Human normal and cancer-associated PSCs were sequenced on the Illumina GAII platform with a 41 bp read length, while mouse PSCs and human MiaPaCa-2 cells were sequenced on the Illumina HiSeq 2000 using bar-coded multiplexing and a 51 bp read length.

Data Analysis

Read alignment and junction mapping was accomplished using TopHat2 v2.0.4 using a 25 bp 5' segment seed for initial mapping followed by differential gene expression analysis using Cuffdiff v2.0.2 to map reads to the reference genome annotation, NCBI mouse build 37.2 and human build 37.2 (Trapnell et al., 2012). Median sequencing read yield per replicate sample was 49.2M for MiaPaCa-2 cells, 25.4M for mouse PSCs and 53.8M for human PSCs. Data were expressed as fragments per kilobase of exon per million fragments mapped (FPKM). Volcano plots were generated from Cuffdiff output using CummeRbund v2.0.0 (Trapnell et al., 2012).

Drug Preparation

Cerulein was purchased from Sigma-Aldrich and resuspended in sterile normal saline at 10 µg/ml, and stored at −20° C. for up to 6 months. Calcipotriol (Tocris) was resuspended as a concentrated stock solution at 100 mM in DMSO, then diluted to 20 μM in normal sterile saline. Diluted aliquots of calcipotriol were stored at −20° C. protected from light for up to 6 months. Gemcitabine (Gemzar, Eli Lilly) was resuspended in normal sterile saline at 5 mg/ml dFdC and stored at room temperature.

Chronic Pancreatitis Model

Chronic pancreatitis was induced in wild-type C57BL6/J mice beginning at 8 weeks of age. Ten animals per cohort received intraperitoneal injections of saline, 50 μg/kg cerulein, or cerulein plus 40 μg/kg calcipotriol. Cerulein injections were administered as 6 hourly injections 2 times per week for 12 weeks and analyzed 1 week after final cerulein injection, adapted from previous studies (Sah et al., 2013; Treiber et al., 2011; Yoo et al., 2005). Calcipotriol injections were administered 3 times per week for the duration of the chronic pancreatitis study. For acute pancreatitis studies, 8-week-old wild-type or Vdr−/− mice received 6 hourly intraperitoneal injections of 50 μg/kg cerulein on days 1, 3, and 5, with or without single daily injections of 40 μg/kg calcipotriol. Mice were sacrificed on day 6. At necropsy, pancreata were harvested and digested for PSC isolation as described above, or prepared for histological analysis as described herein.

Masson's Trichrome Staining

Formalin-fixed, paraffin-embedded tissues were cut into 5 μm sections and stained using a Masson's trichrome staining kit (IMED Inc.) according to the manufacturer's protocol. For quantification of fibrous area, multispectral imaging was performed, and aniline blue-positive area was determined and quantified using Nuance 3.0.1.2 software. Six independent fields were captured per sample.

Sirius Red Staining

Histological sections were cut from formalin-fixed tissues at 7 μm thickness Sirius Red/Fast Green staining (Chondrex) was performed per manufacturer's instructions. Images were obtained and quantification of Sirius Red-positive area performed using Nuance 3.0.1.2 software. Six independent fields were captured per sample.

Immunoblotting

Whole-cell extracts were prepared in lysis buffer containing 1% Triton X-100, protease inhibitor cocktail (Roche), and PhosSTOP phosphatase inhibitor cocktail (Roche) Immunoblotting was performed as previously described (Sherman et al., 2010). Primary antibodies used included phospho-STAT3 (Tyr705) 1:1000 (Cell Signaling Technology), VDR D-6 1:1000 (Santa Cruz Biotechnology), and Actin 1:5000 (Sigma). Anti-rabbit IgG-HRP was used as a secondary antibody 1:5000 (Jackson Immunoresearch).

Chromatin Immunoprecipitation

The hPSC cell line was utilized for chromatin immunoprecipitation, which was described previously (Barish et al., 2010). Briefly, cells were fixed in 1% formaldehyde, and nuclei were isolated and lysed in buffer containing 1% SDS, 10 mM EDTA, 50 mM Tris-HCl pH 8.0, and protease inhibitors, and sheared with a Diagenode Bioruptor to chromatin fragment sizes of 200-1000 base pairs. Chromatin was immunoprecipitated with antibodies to VDR (C-20, Santa Cruz Biotechnology), SMAD3 (Abcam), or rabbit IgG (Santa Cruz Biotechnology).

Example 2

Identification of Cancer-Associated Gene Signatures in PSCs

To characterize cancer-associated changes in PSCs, massively parallel sequencing (RNA-Seq) of the PSC transcriptome was performed at various stages of activation. The progressive activation of primary PSCs in culture (Omary et al., 2007) was capitalized, and the transcriptome of pre-activated (3-day culture) and activated (7-day culture) PSCs isolated from healthy mouse pancreas were analyzed (FIG. 1A and FIGS. 2A-2C). This analysis revealed that, during activation, PSCs decrease expression of genes implicated in lipid storage and lipid metabolism, consistent with loss of the lipid droplet phenotype associated with quiescence. Activation also resulted in increased expression of a cadre of genes previously associated with tumor-supporting potential including cytokines, growth factors, ECM components, and signaling molecules such as Wnts. Concurrent induction of inflammatory genes was of particular interest, as cytokine induction by the stroma has been shown to promote pancreatic cancer initiation and progression in a paracrine manner (Fukuda et al., 2011; Lesina et al., 2011).

In addition to the PSC "activation signature" resulting from transdifferentiation in culture, the PSC "cancer signature" was analyzed to further define the cancer-associated PSC phenotype. Human PSCs isolated from patients with PDA (CAPSCs) or from patients undergoing resection for benign conditions were also subjected to transcriptome analysis (FIG. 1B). These human PSCs were cultured (and thus culture-activated) for 15 days to achieve adequate yield and purity. This comparison of activated non-cancer associated PSCs to cancer-associated PSCs reveals changes to the activated phenotype resulting from exposure to the tumor microenvironment. Both the activation and cancer signatures include gene classes from a previously identified stromal signature which predicts poor survival and chemoresistance in PDA (Garrido-Laguna et al., 2011). In addition, lipid storage genes such as fatty acid binding proteins were downregulated in both signatures, and were accompanied by increased expression of genes implicated in the cholesterol biosynthesis and uptake pathway, consistent with an increased proliferative capacity. Given a tenuous blood supply and the severely avascular nature of PDA, particularly within stromal regions, the reciprocal induction of negative angiogenic regulators and suppression of angiogenic inducers is auspicious (FIG. 1C). In particular the induction of thrombospondin-1 (Thbs1), a well-described and potent endogenous inhibitor of angiogenesis and a marker of solid tumors (Lawler, 2002), was observed. Both gene signatures include ECM components, cell adhesion molecules, inflammatory mediators, paracrine growth and survival factors, genes implicated in lipid/cholesterol metabolism and modulators of signal transduction.

Example 3

VDR Regulates the PSC Activation Network

These analyses also revealed that PSCs unexpectedly express high levels of the vitamin D receptor (VDR), previously thought not to be expressed in the exocrine pancreas (Zeitz et al., 2003) (FIGS. 1D, 1E, 2D and 2E). VDR expression was maintained in the cancer-associated PSCs (FIG. 1F). This druggable receptor was examined in light of previous work implicating VDR as a critical regulator of the fibrogenic gene network in closely related hepatic stellate cells (Ding et al., 2013) and due to the established anti-inflammatory (Cantorna et al., 1996, 1998; Cantorna et al., 2000; Ma et al., 2006; Nagpal et al., 2005; Deeb et al., 2007) actions of $1,25(OH)_2D_3$ and its analogues. Also germane to this study is the strong inverse correlation between plasma vitamin D levels and pancreatic cancer risk (Wolpin et al., 2012), a relationship that remains unexplained. Further, vitamin D deficiency has been linked to chronic pancreatitis (Mann et al., 2003).

Calcipotriol (Cal), a potent and nonhypercalcemic vitamin D analog was used to control VDR induction (Naveh-Many and Silver, 1993). While not present in any post-surgical CAPSCs, surprisingly, Cal treatment induced lipid droplet formation in 19/27 primary patient samples (FIGS. 3A and 4A), and decreased expression of αSMA (ACTA2) in 24/27 patient samples (FIG. 3B), consistent with reversion to quiescence.

To assess the genome-wide effects of VDR activation in PSCs, transcriptome analysis of pre-activated and activated PSCs grown in the presence or absence of VDR ligand was performed. While Cal treatment affected gene expression in pre-activated PSCs (significantly increased and decreased expression of 307 and 431 genes, respectively), VDR activation had a more widespread transcriptional response in activated PSCs (664 and 1616 genes with significantly increased and decreased expression, respectively). A Cal-dependent inhibition of the activation and cancer signatures in PSCs was observed (FIG. 3C, Table 3), including suppression of negative regulators of angiogenesis such as Thbs1 and induction of positive regulators of angiogenesis like Mmp9 (Bergers et al., 2000) (FIG. 3D).

TABLE 3

Figures 3C, 3D:
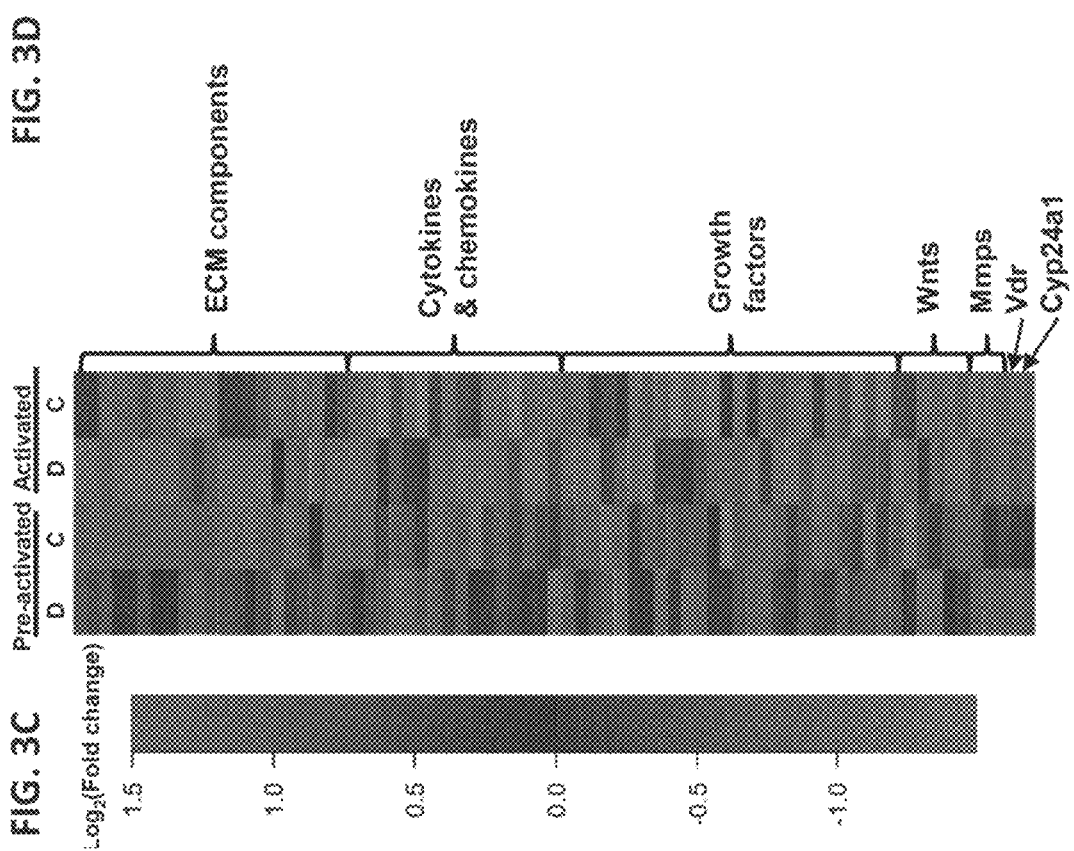

Identity and relative expression of genes displayed in FIG. 3C heatmap

| Gene | Day 3 Cont | Day 3 Cal | Day 7 Cont | Day 7 Cal |
|---|---|---|---|---|
| Ccl12 | 16.9948 | 13.3834 | 58.2957 | 40.9571 |
| Ccl2 | 366.439 | 333.506 | 252.69 | 100.24 |
| Ccl7 | 221.806 | 181.021 | 175.22 | 58.6016 |
| Ccr3 | 0.415907 | 0.072491 | 0.092766 | 0.103886 |
| Ccrl1 | 2.9583 | 0.589842 | 4.62141 | 0.409244 |
| Col12a1 | 140.814 | 115.39 | 275.661 | 132.257 |
| Col15a1 | 42.408 | 8.16068 | 16.5464 | 0.701157 |
| Col16a1 | 17.4914 | 10.6773 | 21.9624 | 11.8557 |
| Col18a1 | 8.72832 | 4.37402 | 10.2631 | 3.05216 |
| Col1a1 | 613.367 | 413.35 | 1918.31 | 868.766 |
| Col1a2 | 904.514 | 635.492 | 1759.65 | 1001.73 |
| Col3a1 | 1304.26 | 489.804 | 1399.98 | 453.127 |
| Col4a1 | 169.341 | 73.1517 | 355.835 | 56.1611 |
| Col4a2 | 108.476 | 53.1738 | 267.076 | 45.2753 |
| Col4a6 | 1.45562 | 1.0448 | 4.6817 | 1.49136 |
| Col5a1 | 82.0461 | 32.308 | 178.049 | 33.0804 |
| Col5a2 | 263.412 | 130.308 | 528.559 | 159.263 |
| Col6a1 | 123.801 | 33.8934 | 121.164 | 19.1727 |
| Col6a2 | 90.0004 | 21.6395 | 64.456 | 4.21871 |
| Col6a3 | 43.4765 | 8.13687 | 47.6343 | 0.171989 |
| Col8a1 | 26.3985 | 16.6737 | 67.3703 | 31.9871 |
| Col8a2 | 0.835173 | 0.414594 | 2.0817 | 0.998107 |
| Col11a1 | 5.6209 | 1.13347 | 12.2119 | 4.92214 |
| Ctgf | 234.261 | 59.7465 | 713.016 | 42.1781 |
| Cx3cr1 | 0.009934 | 0.01077 | 1.11327 | 0.147291 |
| Cxcl12 | 211.644 | 172.155 | 251.048 | 202.677 |
| Cxcl13 | 1.29477 | 1.00293 | 2.91399 | 0.413939 |
| Cxcl14 | 2.43062 | 1.02379 | 2.9176 | 0.685428 |
| Cxcr7 | 10.3703 | 10.7976 | 11.3594 | 4.38706 |
| Fgf10 | 7.94396 | 3.2629 | 6.70396 | 1.42587 |
| Fgf18 | 15.3986 | 14.5143 | 24.8602 | 0.598877 |
| Fgf2 | 119.673 | 63.0183 | 82.197 | 51.3796 |
| Figf | 385.683 | 212.818 | 496.112 | 371.873 |
| Gli2 | 2.47507 | 1.03512 | 2.7476 | 0.579735 |
| Igf1 | 1.59133 | 1.8811 | 28.2601 | 14.46 |
| Igfbp2 | 5.85068 | 4.14298 | 79.7814 | 121.9 |
| Igfbp3 | 407.298 | 77.1041 | 1854.91 | 71.9932 |
| Igfbp4 | 751.247 | 711.902 | 617.533 | 864.825 |
| Igfbp6 | 34.5017 | 36.7414 | 31.8129 | 135.16 |
| Igfbp7 | 386.784 | 223.35 | 897.296 | 431.085 |
| Il18 | 3.16248 | 2.85743 | 5.09757 | 2.07638 |
| Il1r1 | 62.9344 | 44.222 | 40.9406 | 34.7225 |

TABLE 3-continued

Identity and relative expression of genes displayed in FIG. 3C heatmap

| Gene | Day 3 Cont | Day 3 Cal | Day 7 Cont | Day 7 Cal |
|---|---|---|---|---|
| Il6 | 11.9258 | 4.37981 | 33.6427 | 2.4147 |
| Jag1 | 9.48772 | 3.61568 | 13.0127 | 2.73067 |
| Jag2 | 0.050902 | 0.068209 | 0.222199 | 0.062845 |
| Mmp2 | 125.748 | 52.4985 | 108.486 | 23.0001 |
| Nfib | 26.1479 | 25.3524 | 19.8548 | 21.0298 |
| Pdgfc | 8.23967 | 4.70026 | 8.48986 | 1.18999 |
| Pgf | 0.775123 | 0.464103 | 0.761592 | 0.547427 |
| Postn | 205.001 | 18.8806 | 273.757 | 2.07276 |
| Serpine1 | 679.572 | 390.829 | 1029.43 | 363.168 |
| Smo | 32.4758 | 30.5639 | 27.6884 | 24.9848 |
| Tgfb3 | 15.1534 | 11.3445 | 34.2448 | 18.1723 |
| Timp1 | 591.947 | 685.894 | 447.617 | 974.12 |
| Timp2 | 163.712 | 144.858 | 358.136 | 212.664 |
| Timp3 | 60.7974 | 27.9158 | 200.794 | 52.971 |
| Tlr2 | 5.3732 | 6.86588 | 5.73998 | 5.67479 |
| Tlr8 | 4.11176 | 2.55335 | 2.7055 | 3.30651 |
| Tnfaip1 | 37.0789 | 32.9495 | 44.4728 | 24.6246 |
| Tnfrsf11b | 7.10046 | 1.36394 | 22.1842 | 0.815075 |
| Tnfrsf12a | 52.7738 | 68.2134 | 95.4918 | 122.576 |
| Vgf | 0.32529 | 0.28662 | 1.50623 | 0.462996 |
| Wnt2b | 5.28217 | 3.34356 | 6.36536 | 4.6132 |
| Wnt7a | 1.09498 | 0.613477 | 0.102948 | 0.107783 |
| Wnt9a | 1.22649 | 0.856486 | 2.27415 | 0.482617 |
| Vdr | 6.77742 | 12.8055 | 9.05893 | 26.6317 |
| Cyp24a1 | 0.743448 | 132.874 | 0.328976 | 402.257 |

Figure 3F:
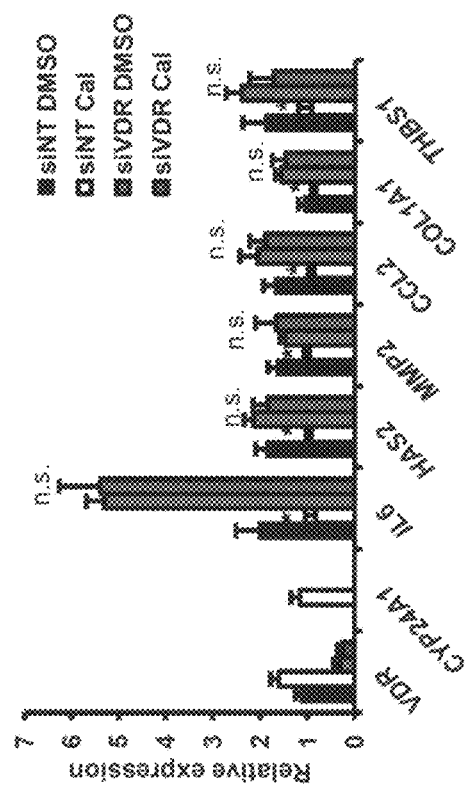
Figure 3E:
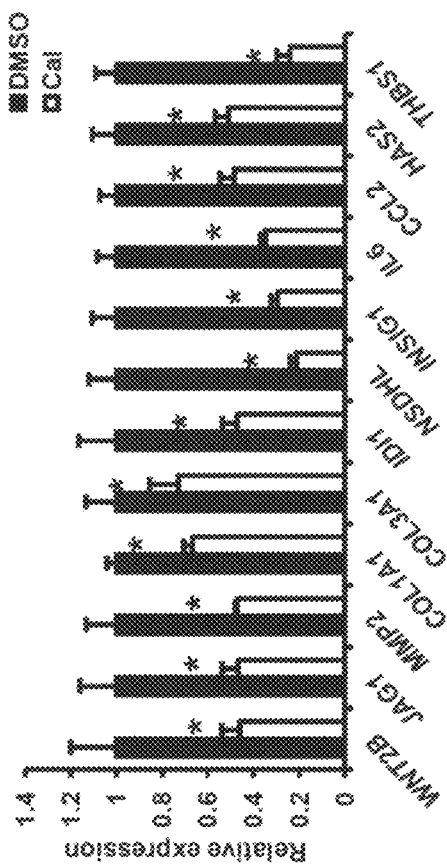

Similar effects of Cal treatment were observed on selected candidate genes in human CAPSCs (FIG. 3E). Furthermore, these effects were dependent on VDR, as siRNA-mediated knockdown of the receptor abrogated Cal-induced expression changes (FIG. 3F). To explain, in part, the broad impact of VDR on the PSC activation program, genomic crosstalk between VDR and the TGFβ/SMAD pathway was assessed (Schneider et al., 2001; Yanagisawa et al., 1999), which was previously demonstrated in hepatic stellate cells (Ding et al., 2013). Consistent with an inhibitory effect on TGFβ/SMAD signaling, Cal increased VDR binding while decreasing SMAD3 binding in the promoter regions of fibrogenic genes (FIGS. 4B and 4C).

Figures 6A, 6B:
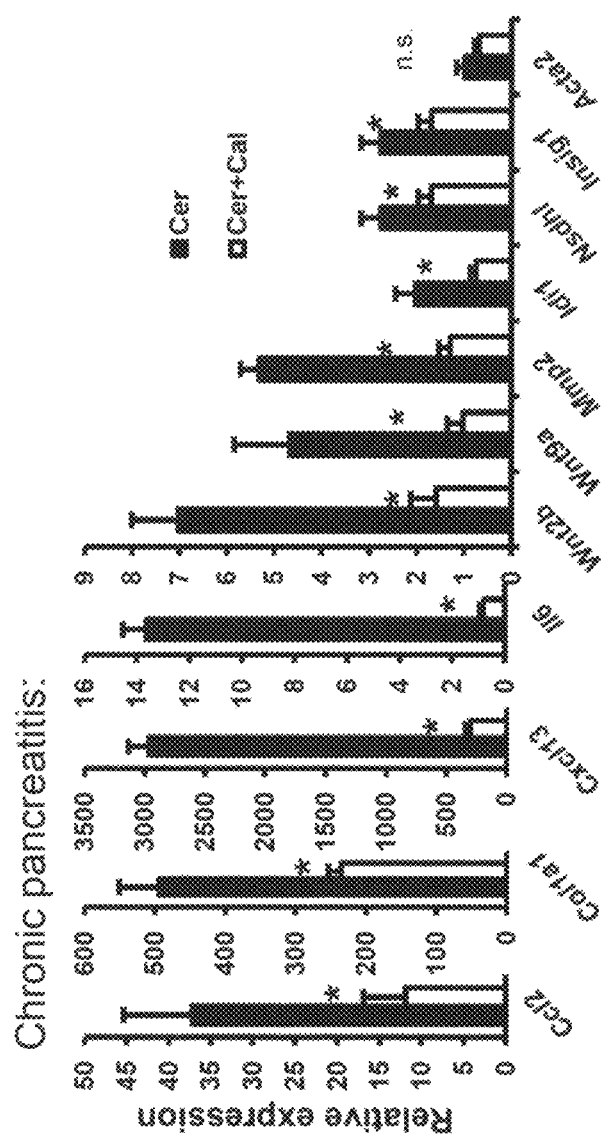
FIGS. 6A-6H. VDR ligand modulates PSC activation in vivo. (A) Expression levels of selected genes in PSCs isolated from mice injected with cerulein (Cer) or cerulein+Cal for 12 weeks (n=10). Values were normalized to 36b4 and are plotted as the mean+SD. (B) Quantification of immunofluorescent staining for phospho-Stat3 (p-Stat3) on frozen sections from wild-type mice treated with cerulein or cerulein+Cal for 12 weeks (n=5). (C) Expression levels of selected genes in PSCs isolated from mice injected with Cer or Cer+Cal to induce acute pancreatitis (for details see Example 1; n=5). Values were normalized to 36b4 and are plotted as the mean+SD. (D) Leukocyte recruitment, as measured by CD45-positive cells, in mice with acute pancreatitis (immunofluorescent staining of frozen sections, positive cells in 200× field, n=5). (E) Fibrosis, as measured by Sirius red staining, in mice with acute pancreatitis (per 200× field, n=5). (F) Expression levels of selected genes in PSCs isolated from Vdr+/+ and Vdr−/− mice injected with cerulein to induce acute pancreatitis (n=5). Means+SD are shown; values normalized to B2M. (G) Sirius red-positive area in Vdr+/+ and Vdr−/− mice with acute pancreatitis (per 200× field, n=5). Statistical significance determined by Student's unpaired t-test (*p<0.05). (H) Expression levels of selected genes in PSCs isolated from Vdr+/+ and Vdr−/− mice after treatment with DMSO or 100 nM Cal for 48 h. Statistical significance determined by Student's unpaired t-test (*p<0.05; n.s.=not significant).
Figure 6D:
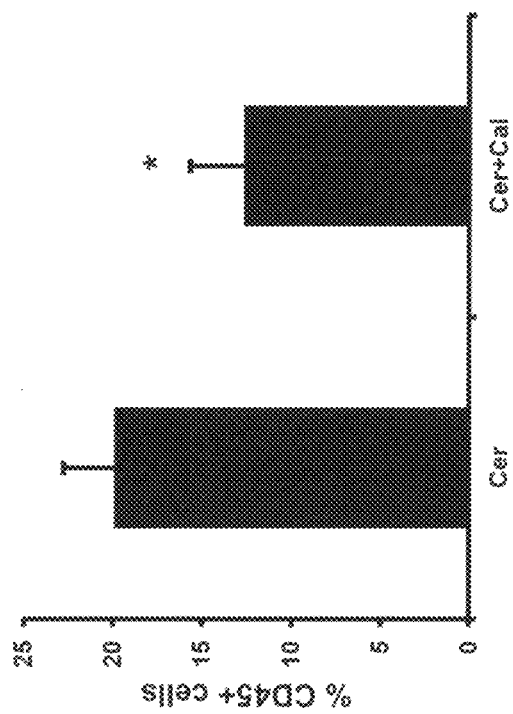
Figure 6C:
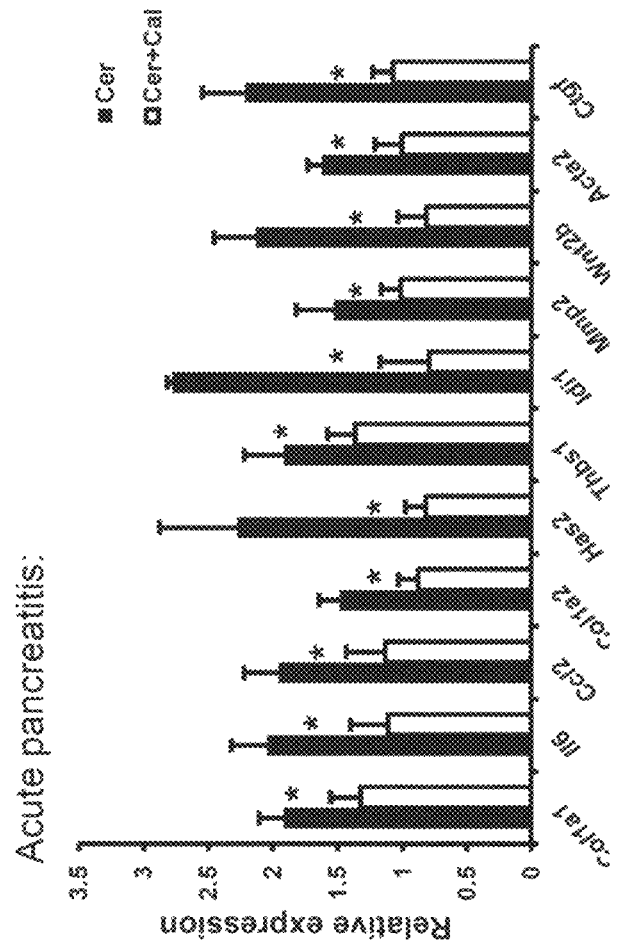

To determine whether VDR activation decreased PSC activation in vivo, we induced experimental chronic pancreatitis in wild type mice using the cholecystokinin analog cerulein (Willemer et al., 1992), and co-administered Cal throughout disease progression. Compared to mice receiving cerulein alone, Cal-treated animals displayed attenuated inflammation and fibrosis, consistent with decreased PSC activation (FIGS. 5A and 5B). Expression of activation and cancer signature genes was decreased in isolated PSCs from mice treated with Cal compared to controls (FIG. 6A). Reductions were observed on activation signature genes which are of functional significance in the tumor microenvironment, including ECM components, inflammatory cytokines and growth factors. In addition, Acta2 expression, which is associated with cell motility, trended downwards. Further, reduced induction of phospho-Stat3 was observed in Cal-treated mice (FIG. 6B), consistent with decreased inflammatory signaling from the stroma. Notably, Stat3 activation has been established as a mechanistic link between inflammatory damage and initiation of PDA (Fukuda et al., 2011; Lesina et al., 2011).

Figure 6F:
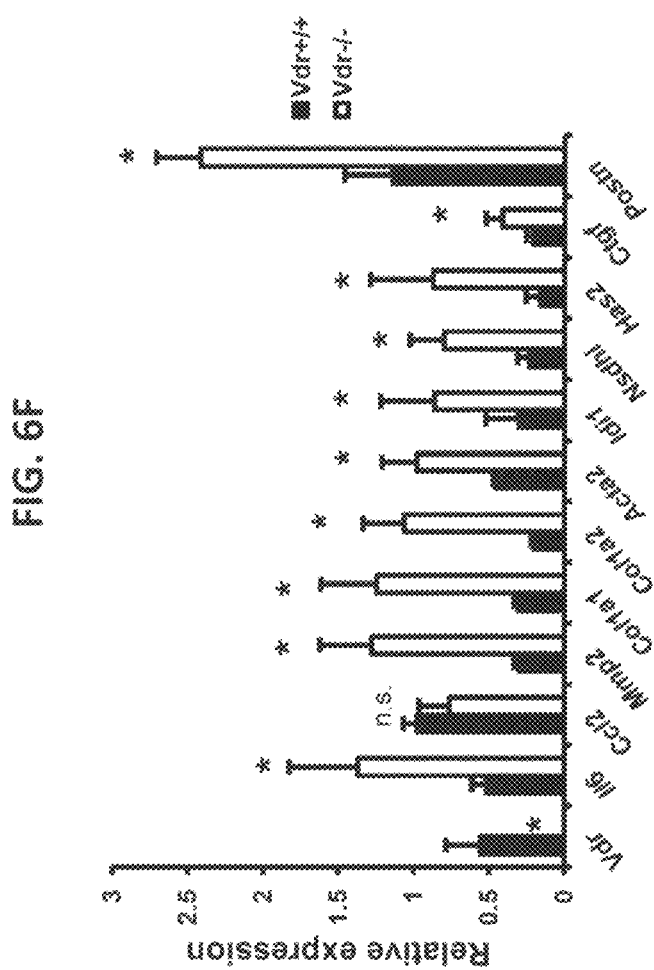
Figure 6E:
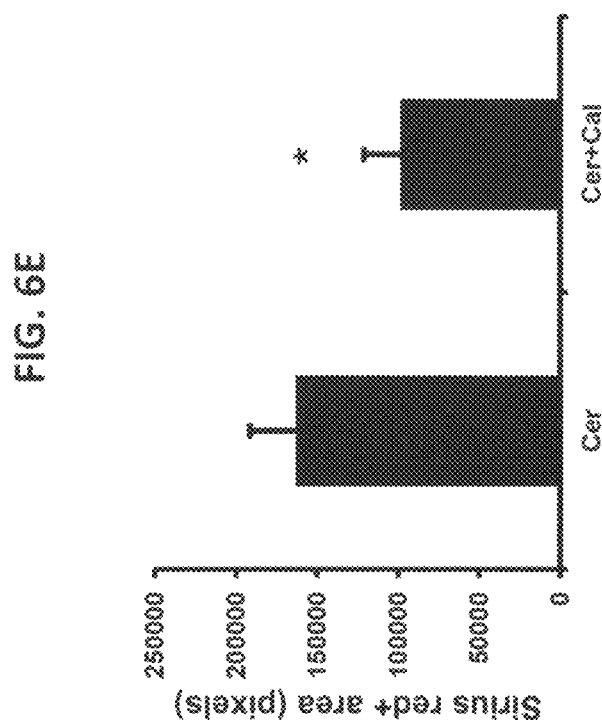
Figure 6H:
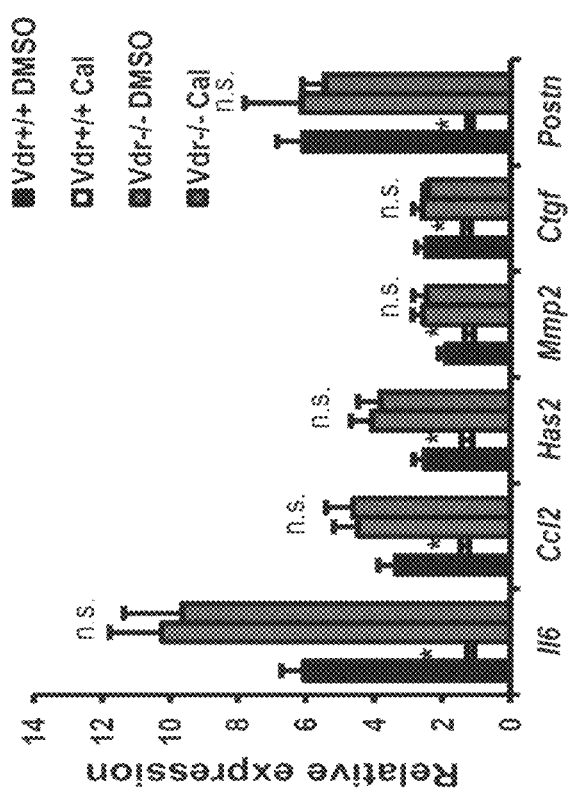
Figure 6G:
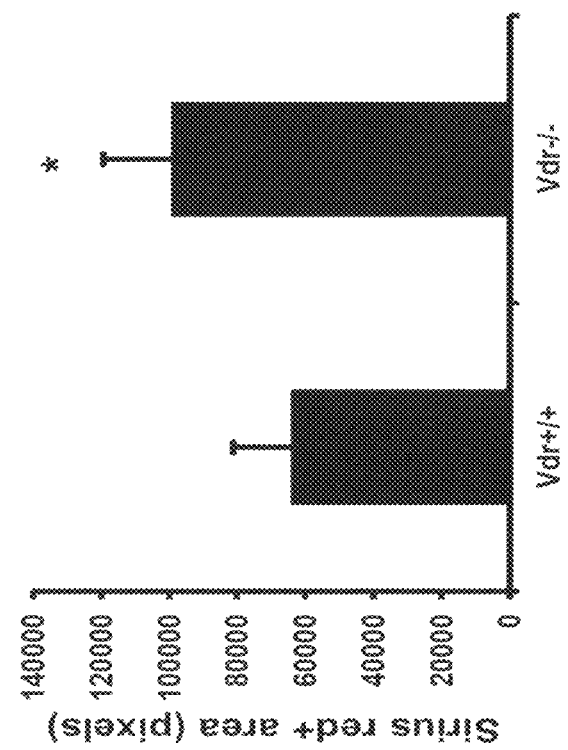

Cal treatment during acute pancreatitis in wild type mice similarly impaired activation-associated changes in PSC gene expression (FIG. 3C), and reduced leukocyte infiltration and fibrosis (FIGS. 3D and 3E). Given the impressive inhibition of PSC activation upon Cal treatment, PSC states were determined in mice lacking a functional VDR. Strikingly, pancreata from Vdr$^{-/-}$ mice displayed spontaneous periacinar and periductal fibrosis (FIG. 5C), further supporting a role for VDR in opposing PSC activation. Consistent with this notion, activation-associated changes in PSC gene expression were augmented in cerulein-induced acute pancreatitis in Vdr$^{-/-}$ mice (FIG. 6F) and were accompanied by increased fibrosis (FIG. 6G). Furthermore, Cal treatment of culture-activated PSCs from Vdr$^{-/-}$ mice demonstrated the VDR dependence of the observed gene expression changes (FIG. 6H).

Together, these results indicate that VDR acts as a master genomic regulator of the PSC activation program, and that VDR induction by ligand restores and promotes the quiescent PSC state both in vitro and in vivo.

Example 4

Stromal VDR Activation Inhibits Tumor-Supportive Signaling Events

The impact of VDR activation in PSCs on crosstalk to tumor cells was determined. While CAPSCs consistently expressed VDR and responded to ligand, pancreatic cancer cell lines displayed varying VDR expression, and typically low VDR activity (FIGS. 7A and 7B). This was also observed in human PDA samples (FIG. 7C).

Figure 8A:
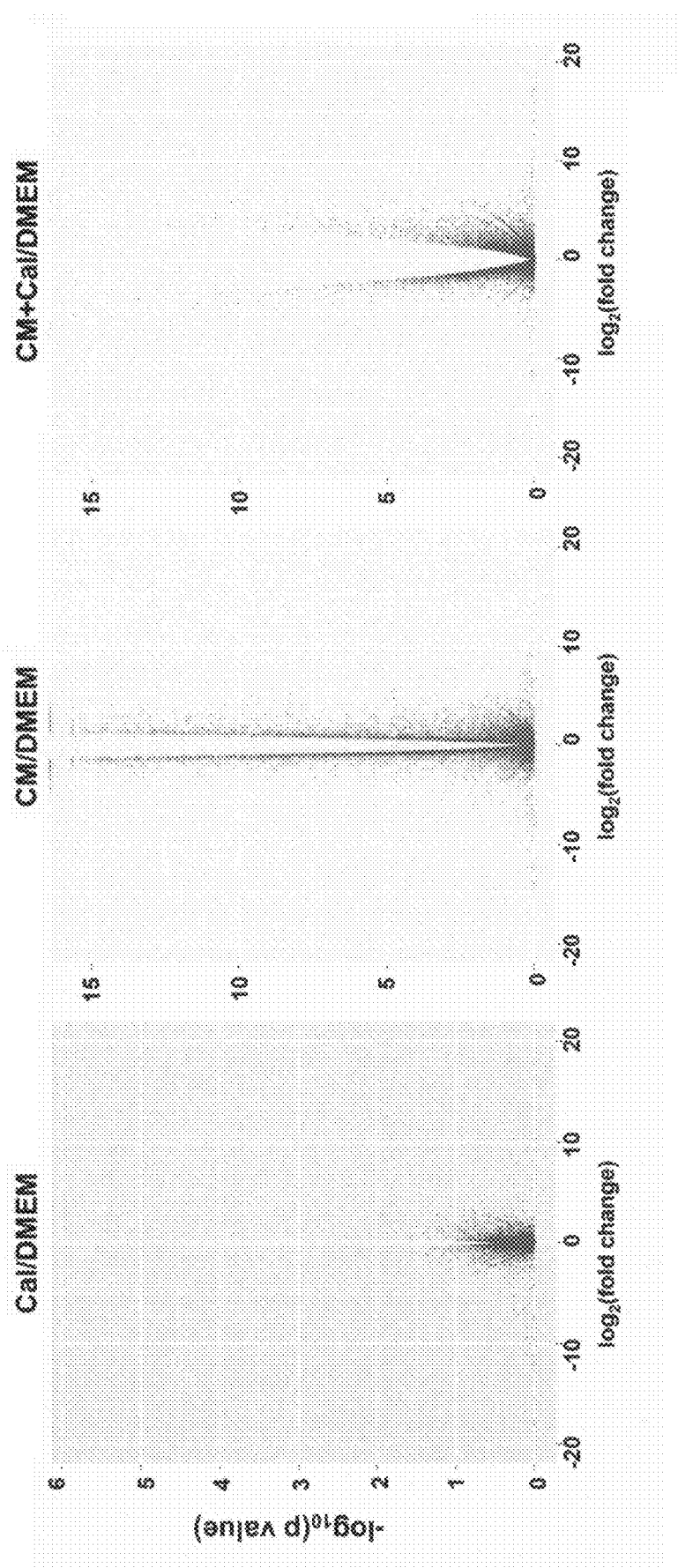
Figures 8C, 8D, 8E:
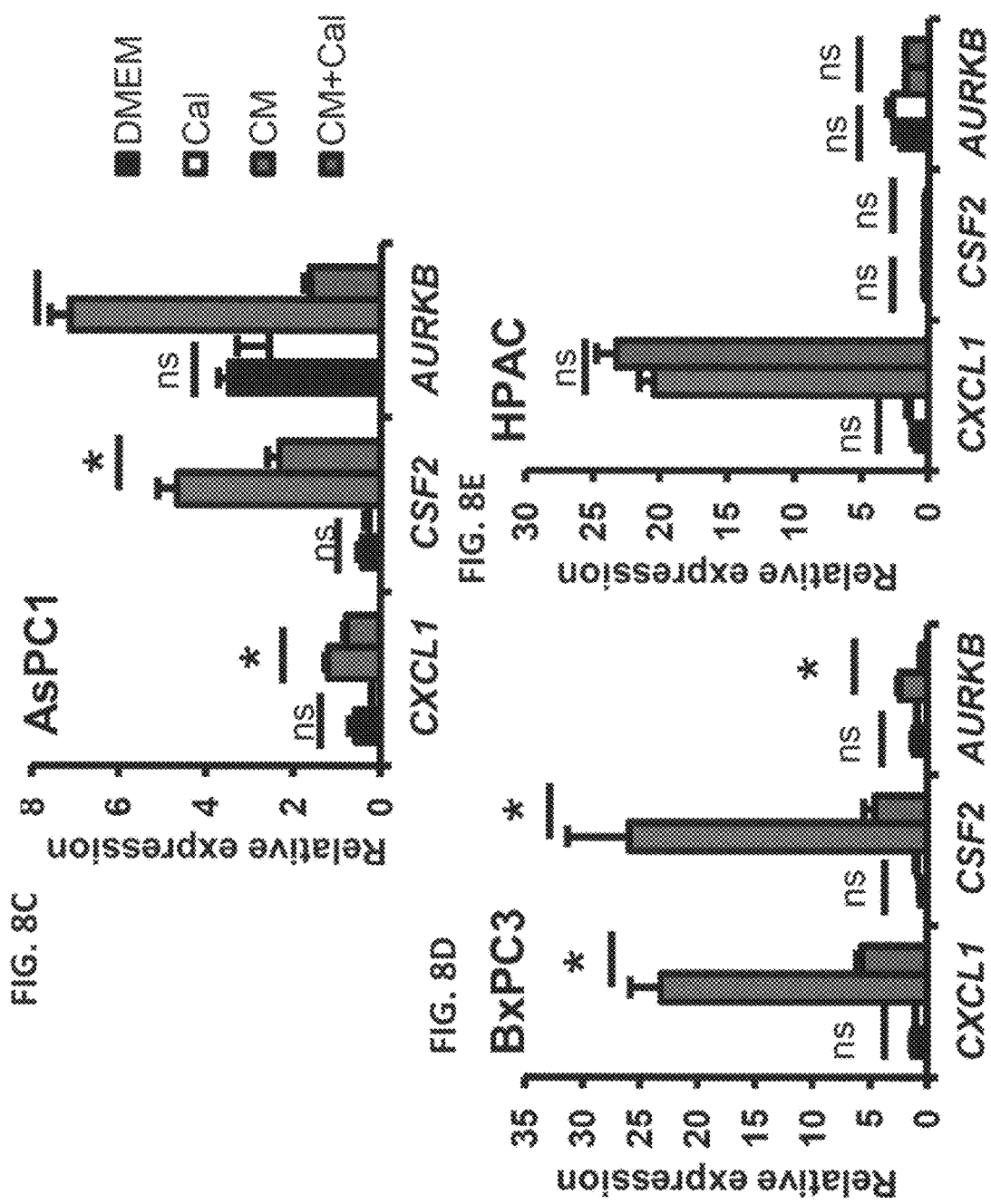

To specifically assess the contribution of stromal VDR activation on the epithelial compartment, the effects of CAPSC-derived secreted factors on the MiaPaCa-2 cell line, which has extremely low VDR expression and no significant response to VDR ligand, were examined (FIGS. 7A and 7B). Primary CAPSCs were grown to confluency, and cultured in the presence or absence of Cal for the final 48 hours of culture. CAPSC conditioned media (CM) was then collected from these cultures, and transferred to MiaPaCa-2 cells for 48 hours. Volcano plot analysis of gene expression in MiaPaCa-2 cells incubated in CAPSC CM revealed broad changes (center panel), which were largely abrogated (right panel) when CM from Cal-treated CAPSCs was used (FIG. 8A). CAPSC CM induced gene expression changes in epithelial cells implicated in proliferation (Table 4), survival, epithelial-mesenchymal transition, and chemoresistance.

TABLE 4

VDR activation in PSCs broadly impacts stroma→tumor crosstalk.

| # | Pathway | Total genes | Genes in data | p-value | FDR |
|---|---|---|---|---|---|
| 1 | Cell cycle_Role of APC in cell cycle regulation | 32 | 18 | 8.840E−20 | 1.633E+01 |
| 2 | Cell cycle_Start of DNA replication in early S phase | 32 | 15 | 4.186E−15 | 1.195E+01 |
| 3 | Cell cycle_The metaphase checkpoint | 36 | 14 | 8.511E−13 | 9.820E+00 |
| 4 | Cell cycle_Chromosome condensation in prometaphase | 21 | 11 | 4.487E−12 | 9.223E+00 |
| 5 | Cell cycle_Transition and termination of DNA replication | 28 | 11 | 2.261E−10 | 7.617E+00 |
| 6 | Cell cycle_Spindle assembly and chromosome separation | 33 | 11 | 1.780E−09 | 6.800E+00 |
| 7 | Cell cycle_Cell cycle (generic schema) | 21 | 9 | 4.135E−09 | 6.501E+00 |
| 8 | Cell cycle_Regulation of G1/S transition | 26 | 9 | 3.845E−08 | 5.591E+00 |
| 9 | Cell cycle_Initiation of mitosis | 25 | 8 | 4.532E−07 | 4.570E+00 |
| 10 | Cell cycle_Role of SCF complex in cell cycle regulation | 29 | 8 | 1.618E−06 | 4.064E+00 |

Figure 8I:
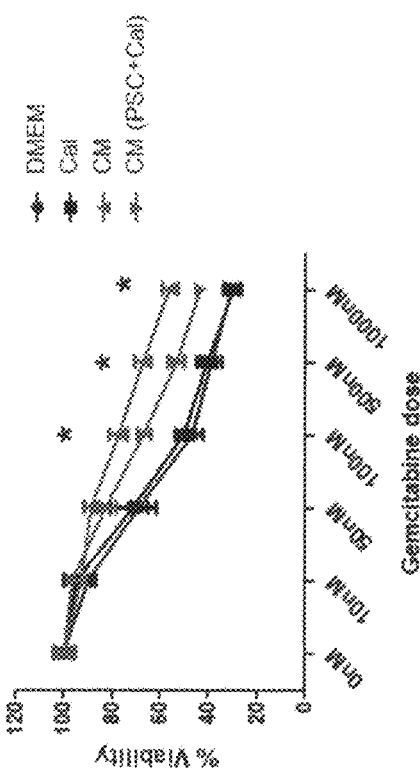
Figure 8H:
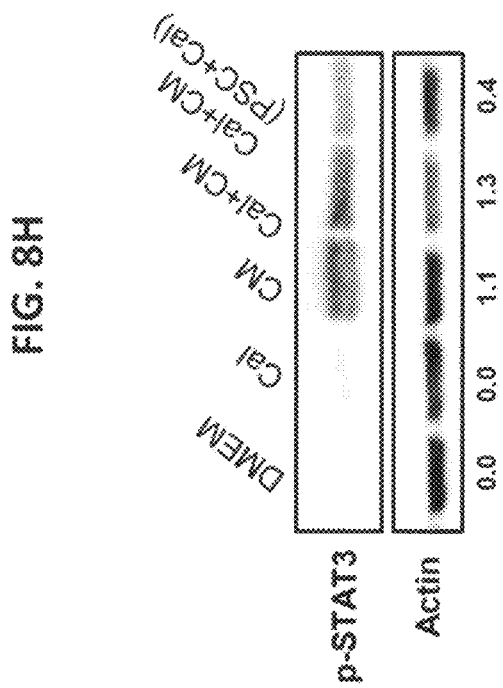

These changes were broadly inhibited by stromal, but not epithelial, VDR activation (FIG. 8B), though direct antiproliferative and pro-apoptotic effects of VDR activation in pancreatic cancer cells have been reported in other experimental systems (Persons et al., 2010; Yu et al., 2010). This sensitivity to stromal but not epithelial VDR activation was replicated in pancreatic cancer cell lines with variable VDR expression (FIGS. 8C-8G). Stromal VDR activation significantly reduced CSF2 expression, which has recently been implicated in pancreatic tumor progression and evasion of antitumor immunity (Bayne et al., 2012; Pylayeva-Gupta et al., 2012). Gene expression changes were accompanied by decreased induction of phospho-STAT3 (FIG. 8H) and decreased resistance to chemotherapy in vitro (FIG. 8I).

These results demonstrate that VDR activation in PSCs negatively regulates the tumor-supporting PSC secretome.

Example 5

VDR Ligand Plus Gemcitabine Shows Efficacy Against PDA In Vivo

The above results indicate that apparent failure of single agent 'Vitamin D therapy' in treating human PDA may reflect that treatment of the stroma alone may be insufficient to achieve a therapeutic benefit. In addition, agents directly targeting the tumor may have limited impact due to intrinsic chemoresistance associated with tumor hypovascularity. A principal goal for PSC targeted therapy is to exploit the inhibition of tumor-stroma crosstalk to enhance efficacy of a cytotoxic (or immunologic) agent, which in the case of gemcitabine, though standard of care, offers minimal (1.5 month) benefit to PDA patients (Burris et al., 1997).

Figure 9A:
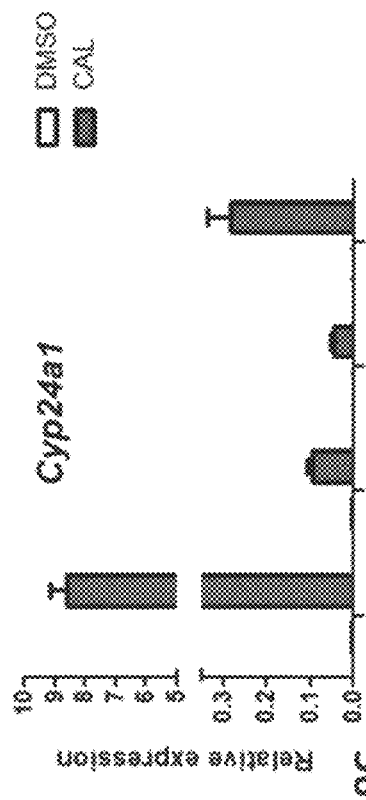
FIGS. 9A-9G. VDR ligand decreases stromal activation in PDA in vivo, related to FIG. 10. Three pancreatic cancer cell lines derived from mouse PDA were compared to mouse PSCs with respect to VDR expression and activity. (A) RNA was isolated from the indicated cell lines and activated mouse PSCs (culture day 7), and Vdr expression was measured by qRT-PCR. (B) The indicated cell types were treated with vehicle (DMSO) or 100 nM calcipotriol for 16 h. RNA was isolated, and expression of Vdr target gene Cyp24α1 was measured by qRT-PCR. Values were normalized to 36b4. Bars indicate mean+SD. (C) PSCs were isolated from mock surgery and allograft recipients. RNA was isolated and qRT-PCR performed to measure expression of PSC activation markers. Values were normalized to 36b4. Bars indicate mean+SD. (D) Pancreata from mock surgery or allograft recipients were harvested and formalin-fixed. FFPE sections were used for Masson's trichrome staining. A representative trichrome stain from PDA in a KPC mouse is shown for comparison. Scale bar=100 μm. (E) PDA allograft recipients received daily intraperitoneal injections of 60 μg/kg calcipotriol or saline for 21 days. Pancreata were harvested and fixed in formalin. FFPE sections were stained with Masson's trichrome (quantification per 200× field below; n=5, *p<0.05 by Student's t-test). Scale bar=100 μm. (F&G) PDA allograft recipients received daily intraperitoneal injections of 60 μg/kg calcipotriol or saline for 21 days, and intraperitoneal injections of 20 mg/kg gemcitabine Q3DX4 for the final 12 days of treatment. Pancreata were harvested, sliced, and immediately fixed in formalin or frozen in liquid nitrogen. (F) FFPE sections were used for immunohistochemical staining of phospho-histone H3 and subsequent quantification (see Experimental Procedures). Plot indicates range, median, and quartiles. *p<0.05 by Student's t-test. (G) Flash-frozen pancreata were homogenized, RNA isolated, and expression of stromal and epithelial genes from our gene signatures were measured by qRT-PCR. Values were normalized to 36b4. Bars indicate mean+SD. *p<0.05 by Student's t-test. n.s.=not significant.
Figure 9B:
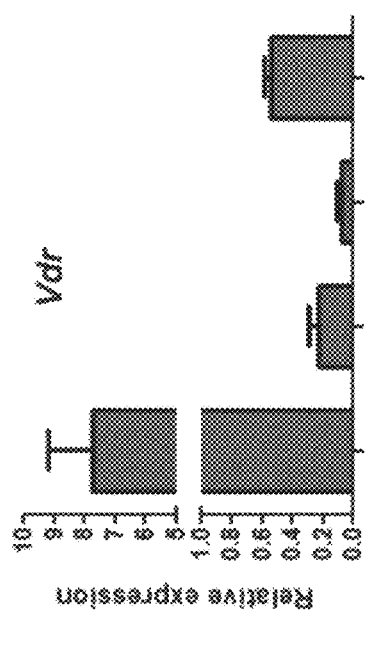
Figure 9C:
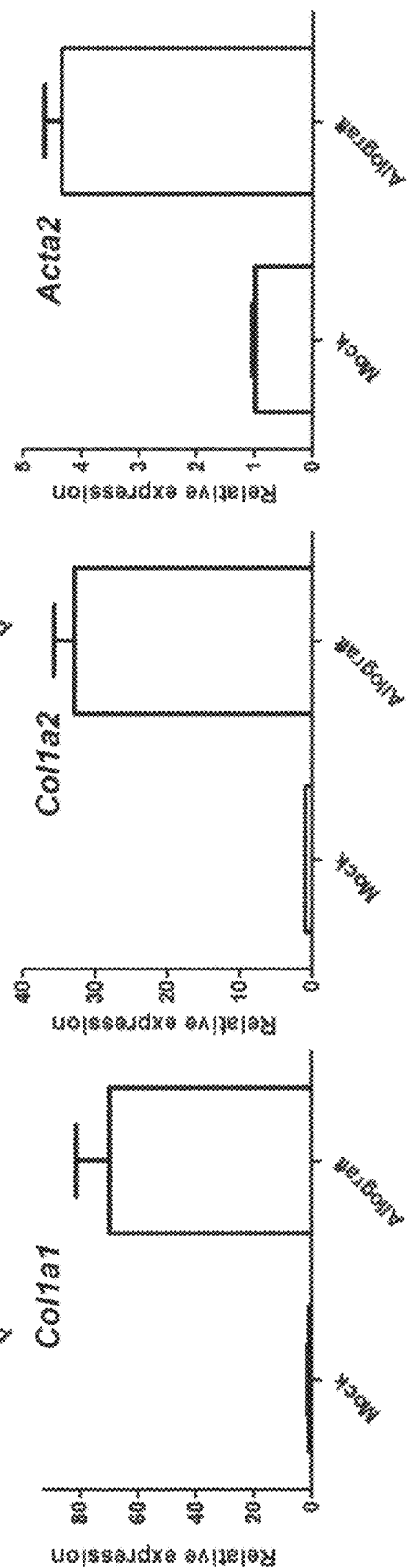
Figures 9D, 9E:
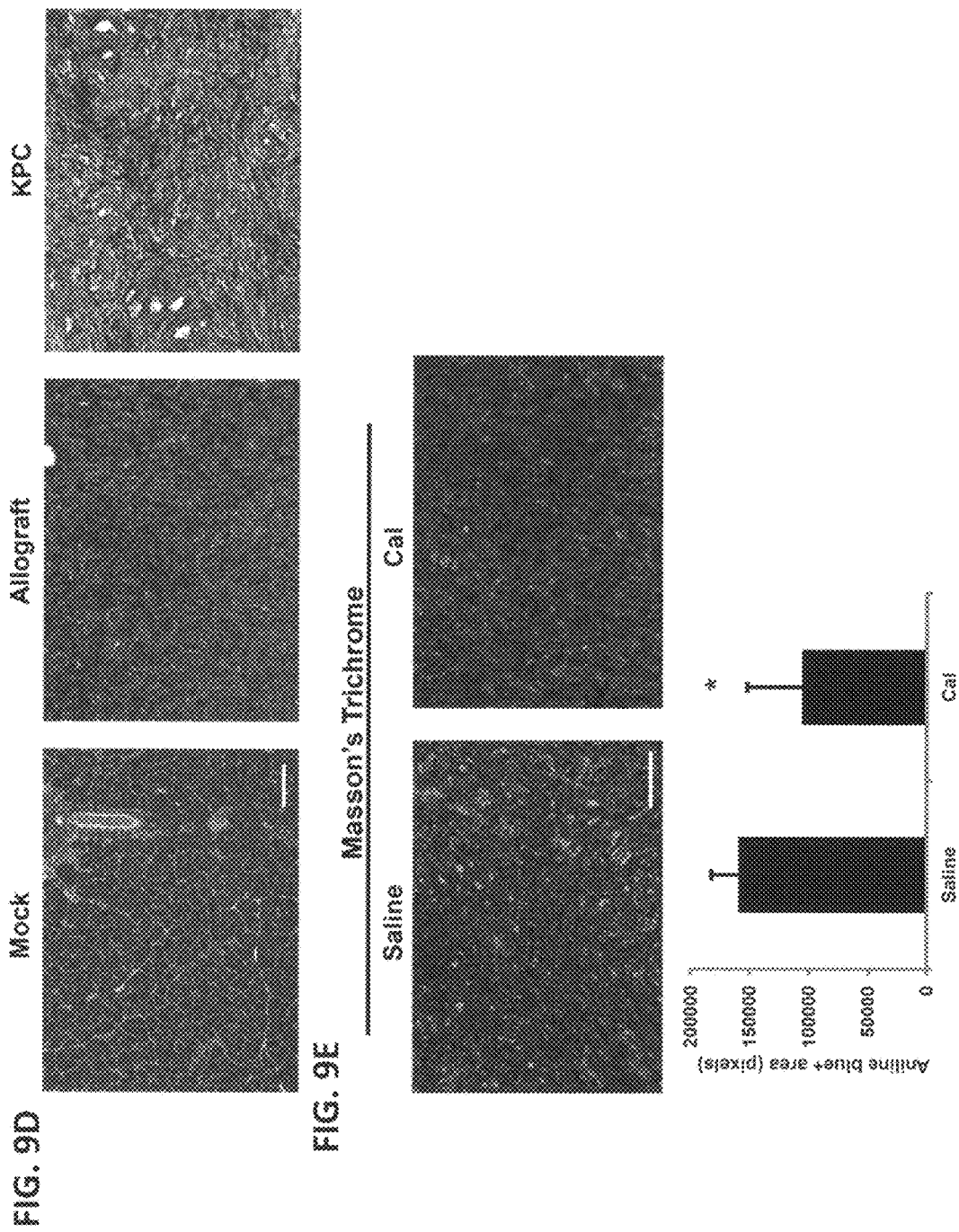
Figure 9F:
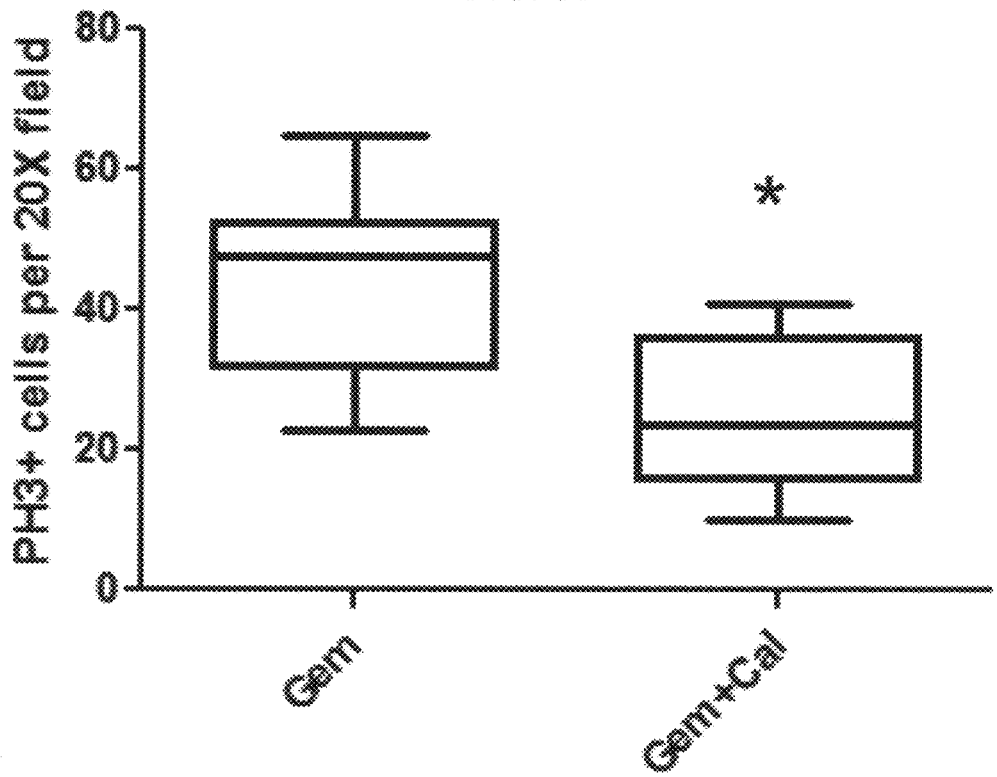
Figure 9G:
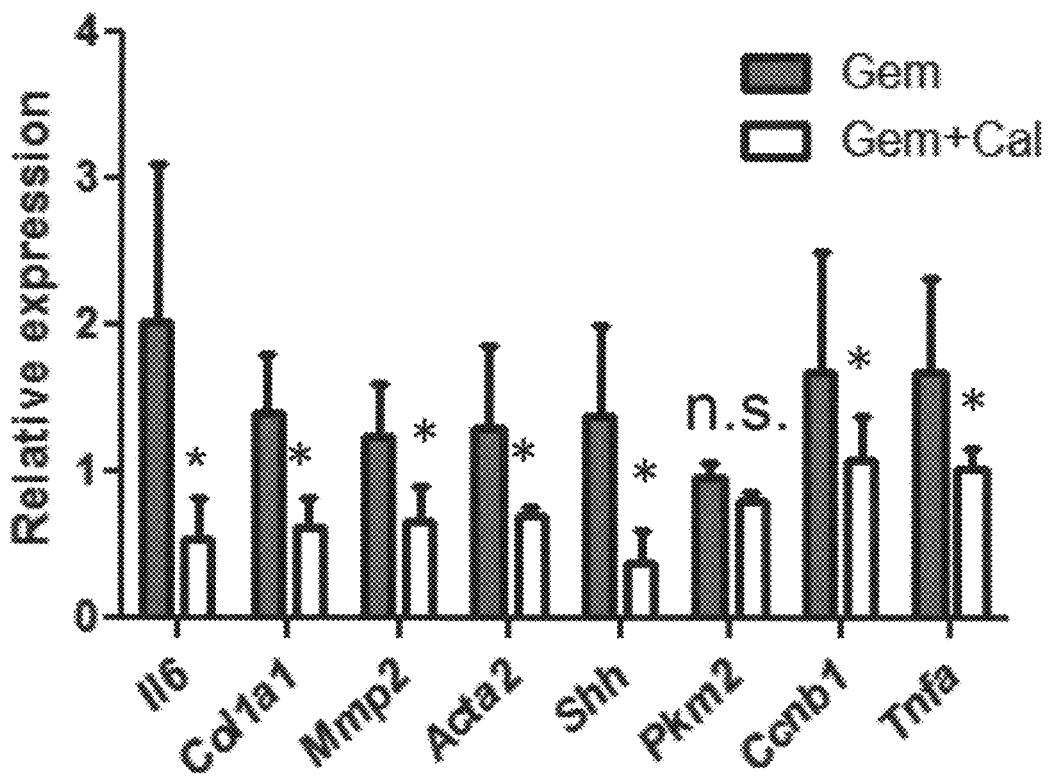

To demonstrate the potential of vitamin D combination therapy, Cal treatment in an orthotopic allograft model utilizing immune-competent hosts was examined (Collisson et al., 2012). The tumor cells for transplantation were derived from mice which conditionally express endogenous mutant Kras, lack p53 in the pancreas (Bardeesy et al., 2006), and express low levels of Vdr (FIGS. 9A and 9B). Two other mouse PDA-derived cell lines demonstrated low VDR expression and activity as well (FIGS. 9A and 9B). This indicates that any observed therapeutic effect would likely result from host-derived stromal VDR activation, though some contribution from the epithelial compartment is not excluded. Though the stromal reaction in transplant models of PDA is subdued compared to the spontaneous KPC (LSL-Kras$^{G12D/+}$;LSL-Trp53$^{R172H/+}$;Pdx-1-Cre) model (Hingorani et al., 2005; Olive et al., 2009), measureable PSC activation of Col1α1, Col1α2, and Acta2 was observed in allograft recipients, accompanied by fibrosis (FIGS. 9C and 9D). Cal treatment decreased stromal activation and fibrosis in transplanted mice (FIG. 9E). Though transplant models are responsive to gemcitabine, mice treated with gemcitabine were compared to those treated with a combination of gemcitabine and Cal Importantly, in combination therapy recipients, a clear improvement in gemcitabine responsiveness was observed with respect to inhibition of proliferation and expression of stromal and epithelial genes from the observed signatures for PSC activation (FIGS. 9F and 9G).

Figure 10E:
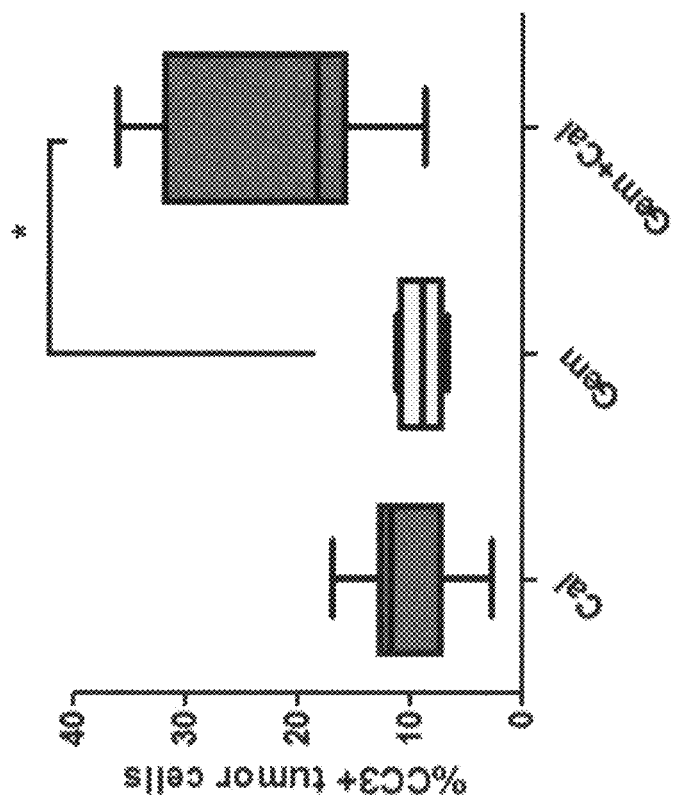
Figure 11A:
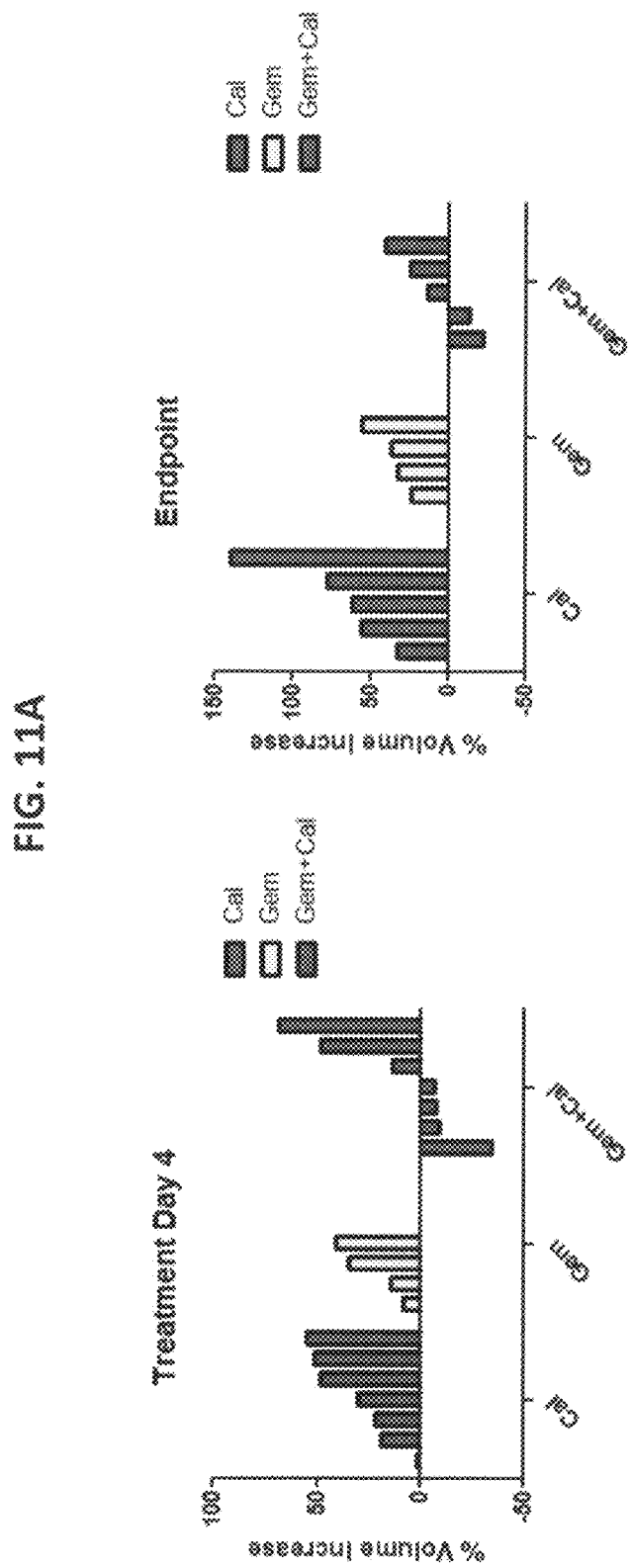
FIGS. 11A-11B. VDR ligand increases gemcitabine efficacy in vivo, related to FIG. 12. (A) PDA-bearing KPC mice were treated as indicated and imaged by high-resolution ultrasound before the start of treatment, on day 4 of treatment, and at study endpoint (see Example 1). One mouse in the gemcitabine cohort was not imaged on day 4, and 2 mice from both the Cal and Gem+Cal cohorts were sacrificed before the endpoint per institutional guidelines. Waterfall plots indicate % volume increase from pre-treatment tumor volumes on treatment day 4 (top) and at study endpoint (bottom). (B) Tumors were harvested from KPC mice treated with the indicated regimen, and homogenates were analyzed by LC-MS/MS to determine intratumoral concentrations of gemcitabine (dFdC; top left), and its deaminated metabolite (dFdU; top right). Ratio of dFdC/dFdU appears in the bottom row. Lines indicate mean±SD. Outliers were identified and appear in red boxes.

The efficacy of gemcitabine plus Cal combination therapy was examined in the KPC model, which recapitulates human PDA in poor uptake of and response to gemcitabine (Olive et al., 2009). Combination therapy significantly reduced tumor volume with transient or sustained tumor regression observed in ~70% of mice (FIGS. 10A and 11A). In agreement with the induction of stromal remodeling, reduced tumor-associated fibrosis was observed in mice which received combination therapy compared to controls (FIG. 10B). Further, combination-treated mice demonstrated significantly altered expression of genes from the stromal and epithelial gene signatures associated with PSC activation (FIG. 10C).

The decreased expression of PSC activation genes and induction of quiescence marker Fabp4 indicates that the tumor-associated PSCs are shifting from an activated toward a quiescent state. The observed differential sensitivity of individual genes to the drug treatment regimens may be the result of specific perturbations to stromal-tumor paracrine signaling in vivo.

Figure 10D:
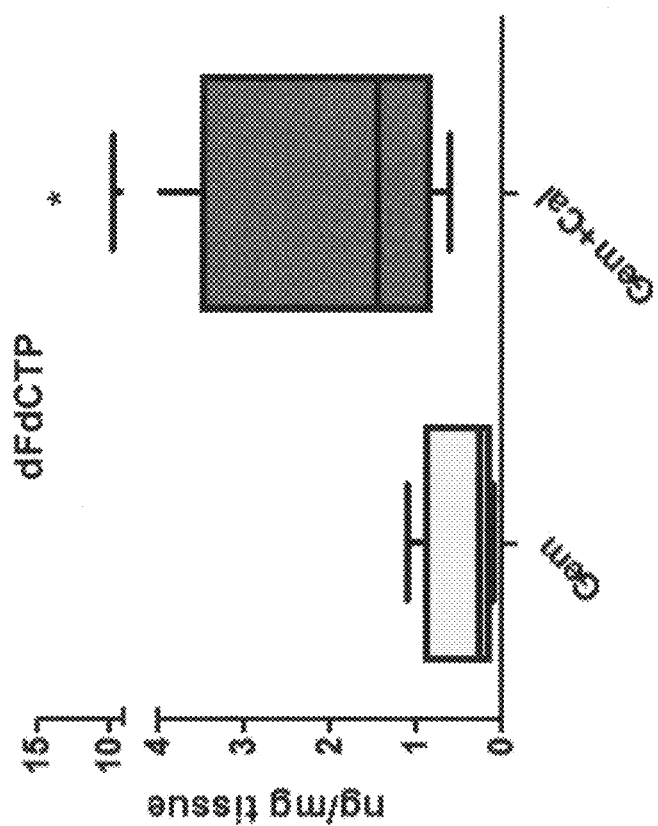
Figure 11B:
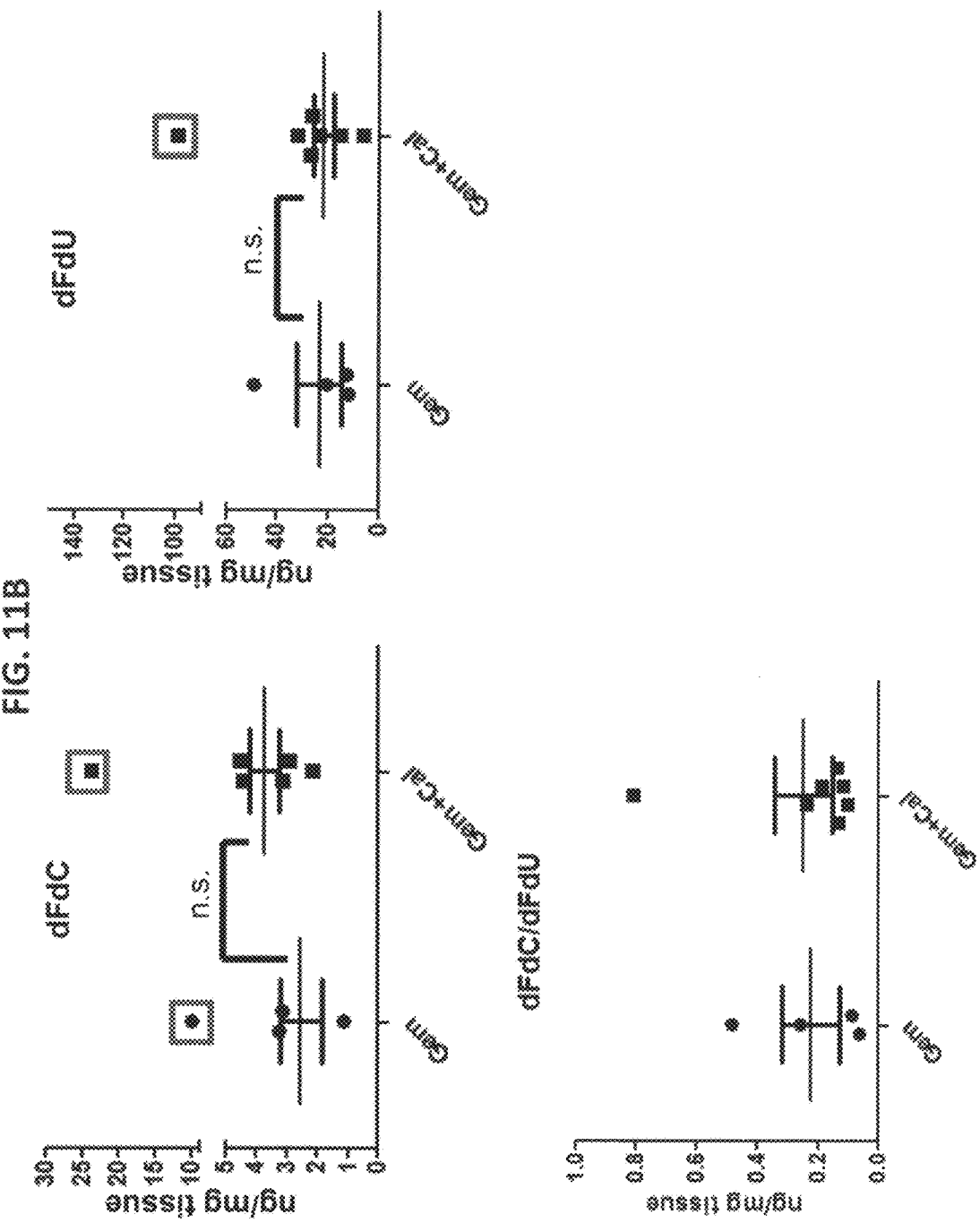
Figure 12A:
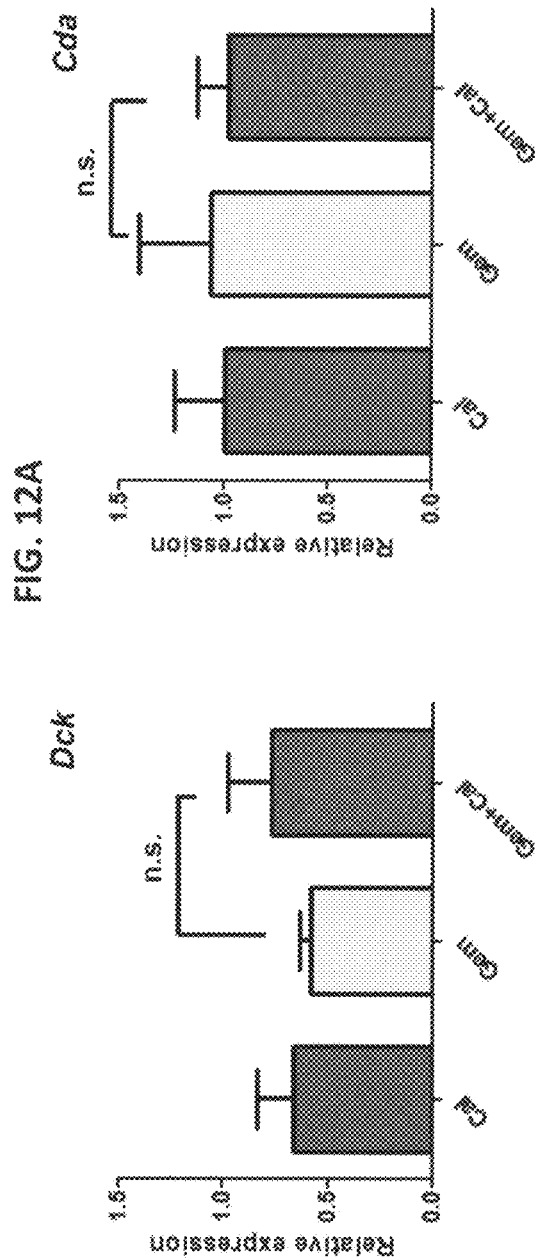

Combination therapy also increased intratumoral concentration and efficacy of gemcitabine (FIGS. 10D and 11B), with ~500% increase in the median concentration of dFdCTP, an active metabolite of gemcitabine, in mice that received combination therapy compared to gemcitabine alone. No drug-induced changes were seen in the expression levels of the gemcitabine degrading enzyme cytidine deaminase (Cda) or the rate-limiting deoxycytidine kinase (dCK) (FIG. 12A), though allosteric effects are possible. Increased dFdCTP was accompanied by increased positivity for apoptotic marker CC3, indicating improved chemotherapeutic efficacy (FIG. 10E).

Figure 12B:
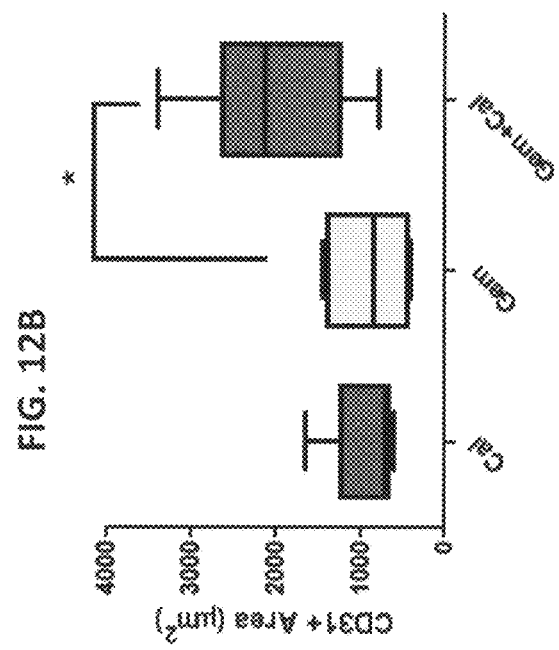
Figure 13:
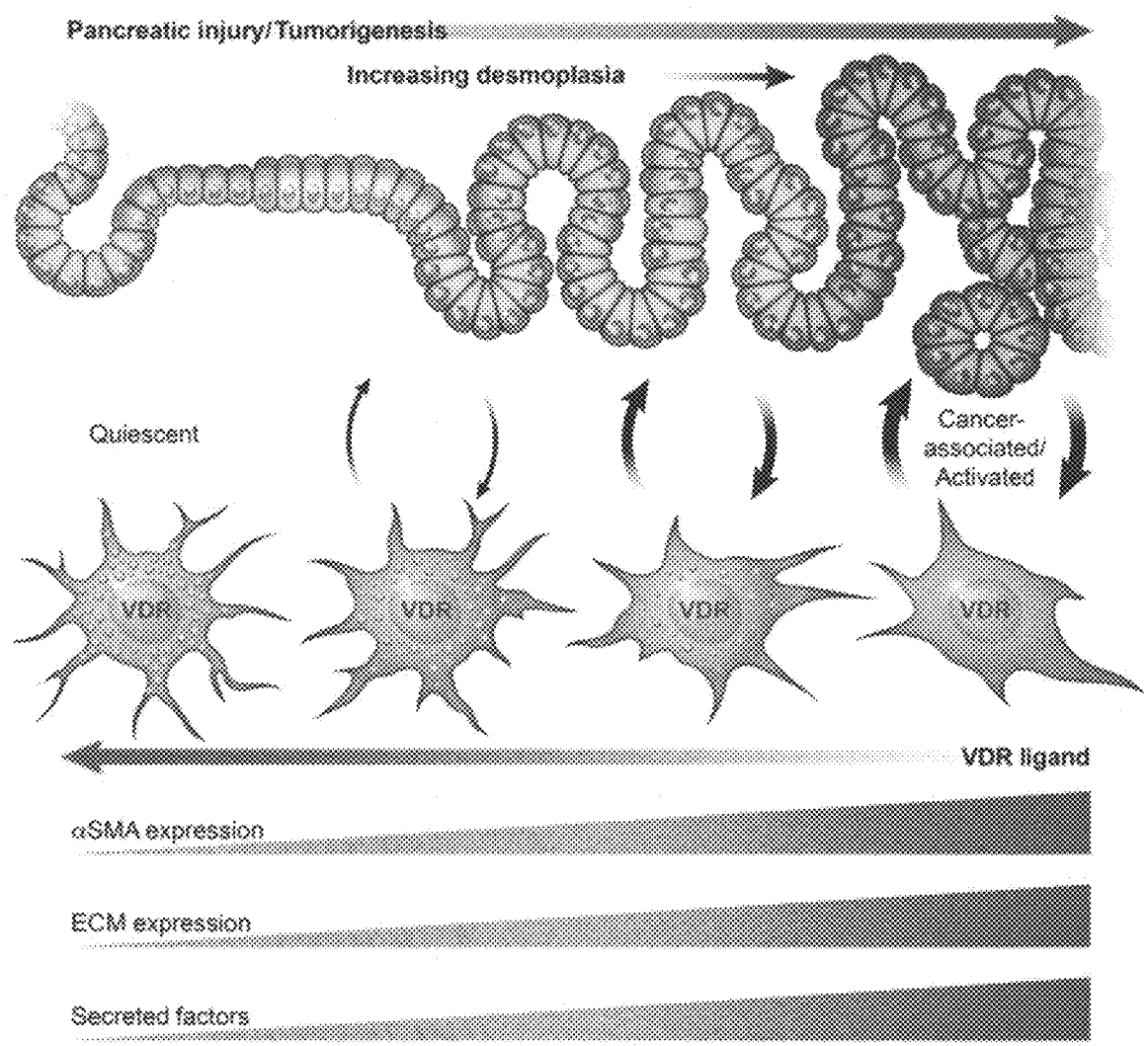
FIG. 13. Model depicting a role for VDR in signal-dependent stromal remodeling, limiting pancreatic tumor-stroma crosstalk. PSCs progressively acquire tumor-supporting functions during activation, a process that is driven by pancreatic injury and tumor progression via secreted factors from the epithelial compartment (and possibly from immune/inflammatory cells). VDR activation drives reversion of PSCs to a more quiescent, less tumor-supportive state. As such, co-treatment of pancreatic tumors with gemcitabine to target the tumor cells and VDR ligand to deactivate PSCs leads to an overall decrease in the reciprocal tumor-stroma crosstalk that presents a major barrier to the delivery and efficacy of gemcitabine alone.

Furthermore, intratumoral vasculature was significantly increased by combination therapy, evidenced by increased CD31 positivity and apparent vessel patency (FIGS. 12B and 12C). Immunohistochemical analysis of tumor sections showed that the collapsed vascular network that characterizes PDA was markedly revitalized after combination therapy, indicating that intratumoral gemcitabine concentration was increased by means of improved drug delivery. While the combination of Cal with gemcitabine markedly improved therapeutic efficacy, Cal showed no measurable beneficial effects as a single agent in the KPC model (FIG. 13).

Example 6

Randomized Phase II/Pharmacodynamic/Genomic Study of Neoadjuvant Paricalcitol to Target the Microenvironment in Resectable Pancreatic Cancer This example describes methods used to demonstrate the synergistic effects of combining a VDR agonist with a chemotherapeutic, to treat a cancer traditionally resistant to chemotherapy or immunotherapy. Although specific VDR agonists and chemotherapeutics for pancreatic cancer are disclosed, one skilled in the art will appreciate that other VDR agonists can be combined with other chemotherapies or biologic therapies (e.g., using known dosages and modes of administration for each) for a particular cancer, such as a cancer of the lung, kidney, prostate, bile duct, or liver.

The effect of targeting the VDR transcriptional pathway in the tumors of patients treated with one cycle of gemcitabine/abraxane with or without paricalcitol prior to surgery for resectable pancreatic cancer can be determined through an assessment of cellular and imaging markers. The methods were also performed to determine the effect of gemcitabine/abraxane with or without paricalcitol on tumor response to neoadjuvant chemotherapy in the primary tumor in resectable pancreatic cancer; identify effects of paricalcitol on the VDR-regulated pancreatic stellate cell gene expression program; determine the safety of this neoadjuvant approach; and analyze circulating markers of endothelial cell function and oxidative stress in paricalcitol-treated patients.

Abraxane (nab-paclitaxel) is a cremophor-free formulation of nanoparticle paclitaxel stabilized with human serum albumin (130 nm particles). The drug achieves enhanced tumor penetration through gp60 albumin receptor-mediated endothelial transcytosis, which enables transit across the vessel endothelium, and makes the active paclitaxel available to the tumor. An additional pharmacodynamic consideration is that the albumin scaffold also binds a tumor-related protein SPARC, which may further enhance localization of this molecule in the tumor tissue. Preliminary data suggest that SPARC-expressing tumors may have better responses to abraxane. In the phase II trial of gemcitabine/abraxane, among 58 evaluable patients there were 23 partial responses (40%) and equivalent number of patients with stable disease (SD) of 4 months or longer, and a median survival of 10.3 months (Von Hoff et al., *J Clin Oncol.* 2011; 29:4548-54). Toxicity was generally well-tolerated, though greater than expected with gemcitabine alone. Dose delays were mainly due to blood/bone marrow treatment-related AEs (mostly neutrophils). There were no nab-paclitaxel dose interruptions due to treatment-related AEs, and 2 instances of dose interruptions for gemcitabine (dermatology/skin: injection site reaction). Also, 2 patients had a total of 3 treatment-related AEs involving blood/bone marrow (neutrophils and platelets) resulting in dose reductions and 2 treatment-related AE resulted in dose discontinuation (gastrointestinal: diarrhea and infection: systemic). There were 3 treatment-emergent AEs resulting in death (lung infection, systemic infection, and gastrointestinal obstruction), but only systemic infection was considered treatment-related. Patients treated with nab-paclitaxel in combination with gemcitabine had levels of myelosuppression consistent with those expected following treatment with taxanes (Von Hoff et al., *J Clin Oncol.* 2011; 29:4548-54).

The neoadjuvant setting provides a framework to combine clinical results and advanced tissue biomarkers to address key questions for targeted cancer therapy. Despite the advances afforded by targeted therapies in selected solid tumors, in pancreatic as in other epithelial cancers progress been modest in the past ten years. One advance has been in the application of systemic therapy and radiation therapy in advance of, instead of after surgery. The advantages of this neoadjuvant approach are many, and include: earlier systemic therapy of what is usually systemic (i.e., not local) disease; better tolerability of chemotherapy and of chemoradiation than in the post-operative setting, allowing more patients to receive the full doses and duration of therapy; smaller radiation fields when the tissue planes have not been disrupted by surgery; shrinkage of the primary tumor to facilitate surgical resection; and, no loss of patients who would benefit from surgery, i.e., no progression during this phase to render a potentially operable patient inoperable. Neoadjuvant therapy is now widely used in locoregionally advanced cancers of lung, breast, gastrointestinal, head and neck, urological, and gynecological origin.

In this trial, an analysis of the effects of VDR activation in stellate cells in the initial therapy of pancreatic cancer will be performed. The paricalcitol (25 µg) dose was selected based on its broad use over a decade in the management of calcium and vitamin D homeostasis in patients undergoing renal dialysis. Paricalcitol is chemically designated as 19-nor-1α,3β,25-trihydroxy-9,10-secoergosta5(Z),7(E),22 (E)-triene, and is a non-metabolized vitamin D analogue that has little hypercalcemic activity. As such, it is a good exemplary compound to effect the desired transcriptional change in the stellate cells. The recommended starting dose of paricalcitol is 0.04 µg/kg (or about 3 µg per dose), but total weekly doses of 15 to 30 µg are reported in the literature without safety concerns (Izquierdo et al., *BMC nephrology* 13:159, 2012; Ketteler et al., *Nephrol Dial Transplant.* 27(8):3270-8, 2012; Tonbul et al. *Ren Fail.* 34(3):297-303,12012), and a trial in combination with taxol in breast cancer patients gave up to 7 µg per day for 12 weeks (Lawrence et al., *Cancer Biol Ther* 14: 476-80, 2013). Accordingly a three times weekly IV schedule (given concerns regarding oral absorption in pancreatic cancer patients) at a flat dose of 10 µg is provided. A detailed population pharmacokinetic analysis including over 600 patients showed mean plasma clearance of 1.75 l/h, and stable phosphorus and calcium levels in the first 30 days of treatment (Noertersheuser et al., *J Clin Pharmacol.* 52(8): 1162-73, 2012). This analysis lends support to the dose and schedule chosen here, and to the schedule of weekly electrolyte monitoring.

In this study, pre-treatment chemotherapy (1 cycle, 4 weeks) alone or in combination with intravenous paricalcitol three times weekly, continuing the Vitamin D preparation up to the day before surgery, will be analyzed. The approach will be assessed in the completion of the therapy: success will be defined by over 90% of the patients getting to surgery. The primary endpoint of interest will be in the effects on tumor: compared with previous tumors examined is there evidence of a difference in fibrosis (qualitative, by immunohistochemistry), or in the appearance or proportion of the tumor cells, or infiltrating lymphocytes? Stellate cells will be microdissected for gene expression profiling, with a view to detecting a VDR-regulated signature in the paricalcitol-treated tumors. Stellate cells will be cultured from tumor fragments, and analyzed genomically and functionally. An immunological and inflammatory assessment at intervals can be performed.

Patients have previously, untreated apparently, resectable adenocarcinoma of the pancreas at registration. It is recognized that a few patients thought to have a cancer, and for whom surgery is indicated, may turn out not to have an adenocarcinoma (these patients will be replaced for the total accrual goal, but where possible samples of primary tumor will be obtained for the endpoints of the study), or may have previously unrecognized criteria for unresectability (these patients will continue to be treated with gemcitabine/abraxane/paricalcitol in the absence of progression, and their outcomes recorded). Patients are age 18 years or older and have an ECOG performance status of 0-2.

Therapy will be administered as follows:

| Agent | Dose | Route | Treatment Administration |
|---|---|---|---|
| Abraxane ® | 125 mg/m2 | IV infusion over 30 minutes | Day 1, 8, 15 |
| Gemcitabine | 1000 mg/m2 | IV infusion over 30-100 minutes | Day 1, 8, 15 |
| Paricalcitol | 10 µg | Three times weekly | From day 1 of therapy until the day before surgery |

In some examples, Abraxane® is given first. Gemcitabine (2'-Deoxy-2',2'-difluorocytidine monohydrochloride) administration may be either over 30 minutes (as in label) or at a rate of 10 mg/m2/minute as recommended elsewhere (Tempero et al., *J Clin Oncol.* 21(18):3402-8, 2003). Dose modifications may therefore lead to changes in the infusion time if the latter approach is used. This cycle will be repeated every 4 weeks for two cycles (that is 8 weeks preoperative therapy in total). Surgery will occur (schedules permitting) within 4 weeks of the last dose of chemotherapy. Post-operative adjuvant chemotherapy will be at the discretion of the treating physician. Patients will receive an appropriate anti-emetic regimen usually including dexamethasone 10-20 mg IV and a 5-HT3 agent of choice, (i.e., ondansetron or granisetron) prior to administration of chemotherapy to decrease the incidence and severity of chemotherapy-associated nausea and vomiting. Drugs such as lorazepam may also be used if clinically indicated.

Patients will begin treatment with intravenous paricalcitol at 10 µg three times weekly. There will be no dose escalation, but toxicity can be monitored weekly to detect calcium or phosphorous elevation which would require a 50% dose decrease (for Calcium>11.5, hold therapy until return to normal).

Dose Limiting Toxicities will be defined by toxicity occurring during the first 4 weeks of this study. A DLT will be considered as any non-hematologic AE of Grade 3 or higher that is judged by the investigators to be probably treatment-related with the exception of nausea and vomiting which have not been treated with optimal anti-emetic therapy. The following hematologic toxicities will be considered a DLT if any occurs in the first cycle:

1) grade 4 neutropenia lasting more than 7 days, 2) febrile neutropenia, 3) platelet count less than 10,000/mm$^3$.

Tolerability of the regimen will be determined by analysis of toxicity after every five patients in conference with the investigators of this trial.

Patients will continue gemcitabine/abraxane/paricalcitol through two cycles of chemotherapy until the day before surgery. Post-operative treatment will be at the discretion of the treating physician.

Tumor will be dissected in the pathology department at the time of surgery, and portions of the tumor mass allocated to various laboratories following verification of diagnosis. Samples will be allocated for detailed immunohistochemical staining for stellate cell isolation, and for CGH and sequencing.

All laboratory measures for routine testing obtained within 2 weeks of the start of each cycle of chemotherapy will be acceptable.

Patients can be assessed by imaging after one cycle of neoadjuvant chemotherapy to determine gross effects on tumor size and conventional markers of therapy effect. A CT or MRI of the abdomen/pelvis and chest (if thoracic disease is present) will be obtained at 6 month intervals after surgery for the first year, and at annual intervals thereafter.

Toxicity will be graded using the NCI Common Toxicity Criteria which is available on the NCI website (www.ctep.cancer.gov). The main toxicities reported with the combination gemcitabine/abraxane are neutropenia, nausea/vomiting, reversible elevations of liver enzymes, and neuropathy. The main toxicities reported with vitamin D preparations are hypercalcemia, which will be tested for every cycle.

Laboratory abnormalities on the day of treatment for second and subsequent courses will be considered in treatment decisions. Values that deviate from eligibility criteria for the study may cause a delay of up to three weeks for recovery to occur. If the abnormalities have not resolved by then, the patient should ordinarily be taken off study. Exceptions may be made.

As specified in the following tables, dose modification should be based upon the worst grade of toxicity experienced. Any dose reduction is continued for all subsequent cycles; therefore, dose re-escalation is not allowed following a dose reduction. Patients who require discontinuation of both gemcitabine and abraxane for toxicity will discontinue protocol therapy, and be scheduled for surgery.

Gemcitabine and nab-Paclitaxel

Rules for Dose Omissions and Modified Schedules

Day 1 dose missed: If the dose held or missed was to be given on Day 1 of the next cycle, that next cycle will not be considered to start until the day the first dose is actually administered to the patient (i.e., 1-2-3-Rest, X-1-2-3-Rest, etc.).

Day 8 dose is missed: Cycle continues per protocol, with one dose not given (i.e., 1-2-3-Rest, 1-X-3-Rest, 1-2-3-Rest, etc.). Day 15 is administered as per cycle calendar if counts and chemistries permit.

Day 15 dose missed: That week becomes the week of rest. Next dose (if counts and chemistries permit) becomes Day 1 of a new cycle, and the patient is considered to have had a x2q3 (21-day) cycle (i.e., 1-2-3-Rest, 1-2-X, 1-2-3-Rest, etc).

Doses will be reduced for hematologic and other non-hematologic toxicities. Dose adjustments are to be made according to the system showing the greatest degree of toxicity. Toxicities will be graded using the NCI CTCAE Version 4.0.

TABLE 5

Dose Levels of Gemcitabine and Abraxane

| Dose Level | nab-Paclitaxel (mg/m$^2$) | Gemcitabine (mg/m$^2$)$^a$ |
|---|---|---|
| Study Dose | 125 | 1000 |
| 1 | 100 | 800 |
| 2 $^b$ | 75 | 600 |

$^a$Dose reductions may or may not be concomitant. Refer to Tables 6-8 for specific recommendations regarding dose reductions
$^b$Additional 25% dose modifications are permissible to establish the tolerable dose for an individual patient Patients who experience study drug-related toxicities that require a delay in scheduled nab-paclitaxel and gemcitabine dosing for ≥14 days will be discontinued from further participation in this study. When a dose reduction is required for Day 1 of any cycle, no dose re-escalation will be permitted for the duration of study treatment.

Dose Modifications at Day 1

In the event dose modifications are required at the beginning of a cycle due to AEs or hematologic toxicities, the doses and schedule of nab-paclitaxel and/or gemcitabine may be adjusted as detailed in Tables 6 and 7 below:

TABLE 6

Dose Modifications for Hematologic Toxicities (Day 1 of Each Cycle)

For counts on Day 1:

| Absolute Granulocytes | | Platelets | Timing |
|---|---|---|---|
| ≥1.5 × 109/L | AND | ≥100 × 109/L | Treat on time |
| <1.5 × 109/L | OR | <100 × 109/L | Delay by one week intervals until recovery |

In the case of dose delays to allow chemotherapy-related toxicity to resolve, HCQ dosing should continue as scheduled.

TABLE 7

Dose Modifications for Non-Hematologic Toxicity (Day 1 of Each Cycle)
Non-hematologic toxicity (except neuropathy, alopecia) ordinarily should have resolved to Grade 0 or 1 before initiating the next cycle. If such toxicity resulted in a dose hold in the previous cycle, the following will determine dosing for the current cycle:

| Toxicity in previous cycle causing dose to be held | Gemcitabine + nab-paclitaxel dose this cycle $^a$ |
|---|---|
| Grade 0, 1 or 2 | Same as day 1 previous cycle |
| Grade 3 toxicity | Decrease gemcitabine by one level |
| Grade 4 toxicity | Decrease gemcitabine two levels$^b$ |
| Dose held in 2 previous consecutive cycles | Decrease gemcitabine by one level |

$^a$ If the toxicity only affects neuropathy, then only nab-paclitaxel should be reduced
$^b$Pulmonary embolism (a Grade 4 toxicity in CTCAE tables) if mild or asymptomatic, will be exempt from this requirement.

Dose Adjustments within a Treatment Cycle

In the event that patients must have treatment delayed within a treatment cycle due to toxicities, those doses held during a cycle will not be made up. Dose modifications due to hematologic toxicity (as represented by the blood counts and toxicities, below) within a treatment cycle should be adjusted as outlined in Table 8.

TABLE 8

Dose Modifications for Hematologic Toxicity within a Cycle (days 8, 15)

| ANC | | Platelets | Nab-paclitaxel | Gemcitabine |
|---|---|---|---|---|
| ≥1500 | AND | ≥100,000 | 100% | 100% |
| 1000-1499 | OR | 75,000-99,000 | 100% | 100% |
| 500-999 | OR | 50,000-74,000 | Decrease one dose level $^a$ | Decrease one dose level |
| <500 Febrile Neutropenia (Grade 3 or 4) | OR | <50,000 | hold Hold. Upon resuming dosing, decrease to next lower level and do not re-escalate throughout the rest of treatment | hold Hold. Upon resuming dosing, decrease to next lower level and do not re-escalate throughout the rest of treatment |

TABLE 8-continued

Dose Modifications for Hematologic Toxicity within a Cycle (days 8, 15)

| ANC | Platelets | Nab- paclitaxel | Gemcitabine |
| --- | --- | --- | --- |
| Recurrent Febrile neutropenia (Grade 3 or 4) | | Decrease to next lower dose level and do not re-escalate throughout the rest of treatment | Decrease 2 dose levels and continue throughout the rest of treatment |

[a] GCSF may be used (at dose and schedule per institutional guidelines) at the discretion of the investigator to maintain 'nab-paclitaxel dose intensity Because of significant risk of non-neutropenic sepsis, at the first occurrence of fever >38.5 degrees Celsius, regardless of the neutrophil count, either ciprofloxacin (500 mg orally bid) or amoxicillin/clavulinate (Augmentin, 500 mg orally bid or tid) should be instituted. At initiation of the study treatment, patients should be provided prescriptions for one or other antibiotic, and instructed to begin treatment at the first observation of a fever or 38.5° C. or more, or if they feel they are developing a fever and a thermometer is not available. They should follow a clear plan for blood count evaluation, and clinical assessment for infection, and/or the need for hospitalization.

Febrile patients will have their treatment interrupted until recovery (temperature below 100F for >3 days), and will be managed according to standard practice for this disorder. The HCQ dosing may continued at the discretion of the physician. Upon resolution of this condition, abraxane and gemcitabine therapy can resume at the next lowest dose. Dose modifications may also be made for non-hematological toxicity within a cycle as specified in Table 9.

TABLE 9

Dose Modifications for Non-Hematological Toxicity within a Cycle CTC Grade

| CTC Grade | Percent of Day 1 |
| --- | --- |
| 0-2 (and Grade 3 nausea/vomiting and alopecia) | 100% |
| 3 (except nausea/vomiting and alopecia) | 50% or Hold[a] |
| 4 | Hold[a] |

[a]This decision as to which drug should be modified will depend upon the type of non-hematologic toxicity seen and which course is medically most sound in the judgment of the physician/investigator. Treatment may be reinstated on Day 1 of the next cycle.

Nab-Paclitaxel treatment can be withheld in patients who experience ≥Grade 3 peripheral neuropathy. Gemcitabine administration can continue during this period at the discretion of the investigator. Nab-Paclitaxel treatment may be resumed at the next lower dose level in subsequent cycles after the peripheral neuropathy improves to ≤Grade 1. Patients experiencing peripheral neuropathy may require an extended delay in scheduled nab-Paclitaxel dosing, but can remain on gemcitabine/HCQ, and have 'nab-paclitaxel reintroduced at a subsequent cycle should the neuropathy improve as above. Patients receiving a reduced dose of nab-Paclitaxel who experience ≥Grade 3 peripheral neuropathy at that dose level requiring a dose delay ≥21 days without resolving to ≤Grade 1 should have 'nab-paclitaxel discontinued.

As observed in other clinical trials, ≥Grade 3 neuropathy related to nab-Paclitaxel is usually seen in later phases of the treatment (cycle 6 and beyond). If ≥Grade 3 neuropathy occurs in early treatment cycles, other factors predisposing the patient to neuropathy might be present (e.g., diabetes, alcohol consumption, concomitant medications). To maintain dose intensity during the first 6 treatment cycles, careful consideration should be exercised when these predisposing factors are present.

Patients who develop Grade 2 or 3 cutaneous toxicity should have their dose reduced to the next lower dose level of both drugs. If the patient continues to experience these reactions, treatment should be discontinued. Patients who develop Grade 4 cutaneous toxicity should have treatment discontinued.

If Grade 3 mucositis or diarrhea occurs, study drug should be withheld until resolution to ≤Grade 1, then reinstituted at the next lower dose level of both drugs. Patients who develop Grade 4 mucositis or diarrhea should have treatment discontinued.

The use of growth factors to support neutrophil counts is permissible after cycle 1 if neutropenia would otherwise require a dose reduction to less than 100 mg/m2 of abraxane. GCSF may also be considered for therapeutic administration in the event of febrile neutropenia as noted above, according to institutional practice.

Thus, in some examples, paricalcitol is administered at 5 or 10 µg IV three times weekly for two-three weeks before surgery. One cycle of gemcitabine/abraxane can be given before surgery, and a 1-2 week interval or longer can be used to permit count recovery. Paricalcitol can be given for 28 days approximately prior to planned surgery, and can be continued up to the day before surgery, since there is no relevant toxicity of this micronutrient. Last dose can be 24 h before surgery (if surgery is delayed, and additional days of therapy may be given to reach the day before surgery). Post-operatively, beginning approximately 4-8 weeks after surgery, patients can be treated with gemcitabine/abraxane.paricalcitol for 3-5 cycles in total.

A patient was treated for 28 days with a non-calcemic Vitamin D analog (Paricalcitol) with one cycle of gemcitabine/abraxane given before surgery, with a 1-2 week interval or longer to permit count recovery. No adverse clinical effects were noted (no elevation calcium levels) before surgery. Notably, the patient's serum CA 19-9 levels, commonly used as a marker for pancreatic tumors, reduced from 120 U/mL to 40 U/mL (normal non cancer patents levels range is 0-37 U/mL). Surgical re-sectioning revealed that the tumor was lighter than normal. Subsequent histological analysis revealed granulomas with few cancer cells. The presence of granulomas, collections of immune cells known as macrophages, indicate that in addition to increasing the efficacy of gemcitabine/abraxane cytotoxicity, this therapeutic approach also achieved a immune response, often blocked in pancreatic cancer. These results describe a novel and effective therapeutic route to treat pancreatic cancer.

REFERENCES

Aikawa et al., (2006). Connective tissue growth factor-specific antibody attenuates tumor growth, metastasis, and angiogenesis in an orthotopic mouse model of pancreatic cancer. Mol. Cancer Ther. 5, 1108-1116.

Apte et al., (1998). Periacinar stellate shaped cells in rat pancreas: identification, isolation, and culture. Gut 43, 128-133.

Apte, M. V., Pirola, R. C., and Wilson, J. S. (2012). Pancreatic stellate cells: a starring role in normal and diseased pancreas. Front. Physiol. 3, 344.

Apte, M. V., and Wilson, J. S. (2012). Dangerous liaisons: pancreatic stellate cells and pancreatic cancer cells. J. Gastroenterol. Hepatol. 27 Suppl 2, 69-74.

Bailey et al., (2008). Sonic hedgehog promotes desmoplasia in pancreatic cancer. Clin Cancer Res. 14, 5995-6004.

Bapiro et al., (2011). A novel method for quantification of gemcitabine and its metabolites 2',2'-difluorodeoxyuridine and gemcitabine triphosphate in tumour tissue by LC-MS/MS: comparison with (19)F NMR spectroscopy. Cancer Chemother. Pharmacol. 68, 1243-1253.

Bardeesy et al., (2006). Both p16(Ink4a) and the p19(Arf)-p53 pathway constrain progression of pancreatic adenocarcinoma in the mouse. Proc. Natl. Acad. Sci. USA 103, 5947-5952.

Barish et al., (2010). Bcl-6 and NF-kappaB cistromes mediate opposing regulation of the innate immune response. Genes & Development 24, 2760-2765.

Bayne et al., (2012). Tumor-derived granulocyte-macrophage colony-stimulating factor regulates myeloid inflammation and T cell immunity in pancreatic cancer. Cancer Cell 21, 822-835.

Bergers et al., (2000). Matrix metalloproteinase-9 triggers the angiogenic switch during carcinogenesis. Nat. Cell Biol. 2, 737-744.

Bhowmick et al., (2004). Stromal fibroblasts in cancer initiation and progression. Nature 432, 332-337.

Bissell and Hines (2011). Why don't we get more cancer? A proposed role of the microenvironment in restraining cancer progression. Nat. Med. 17, 320-329.

Burris, H. A., 3rd, Moore, M. J., Andersen, J., Green, M. R., Rothenberg, M. L., Modiano, M. R., Cripps, M. C., Portenoy, R. K., Storniolo, A. M., Tarassoff, P., et al. (1997) Improvements in survival and clinical benefit with gemcitabine as first-line therapy for patients with advanced pancreas cancer: a randomized trial. J. Clin. Oncol. 15, 2403-2413.

Cantorna, M. T., Hayes, C. E., and DeLuca, H. F. (1996). 1,25-Dihydroxyvitamin D3 reversibly blocks the progression of relapsing encephalomyelitis, a model of multiple sclerosis. Proc. Natl. Acad. Sci. USA 93, 7861-7864.

Cantorna et al., (1998). 1,25-Dihydroxycholecalciferol inhibits the progression of arthritis in murine models of human arthritis. J. Nutr. 128, 68-72.

Cantorna et al., (2000). 1,25-Dihydroxycholecalciferol prevents and ameliorates symptoms of experimental murine inflammatory bowel disease. J. Nutr. 130, 2648-2652.

Collisson et al., (2011). Subtypes of pancreatic ductal adenocarcinoma and their differing responses to therapy. Nat. Med. 17, 500-503.

Collisson et al., (2012). A central role for RAF→MEK→ERK signaling in the genesis of pancreatic ductal adenocarcinoma. Cancer Discov. 2, 685-693.

Deeb, K. K., Trump, D. L., and Johnson, C. S. (2007). Vitamin D signalling pathways in cancer: potential for anticancer therapeutics. Nat. Rev. Cancer 7, 684-700.

Ding et al., (2013). A vitamin D receptor/SMAD genomic circuit gates hepatic fibrotic response. Cell 153, 601-613.

Dowell, N. G., and Tofts, P. S. (2007). Fast, accurate, and precise mapping of the RF field in vivo using the 180 degrees signal null. Magn. Reson. Med. 58, 622-630.

Feig et al., (2012). The pancreas cancer microenvironment. Clin. Cancer Res. 18, 4266-4276.

Fukuda et al., (2011). Stat3 and MMP7 contribute to pancreatic ductal adenocarcinoma initiation and progression. Cancer Cell 19, 441-455.

Garrido-Laguna et al., (2011). Tumor engraftment in nude mice and enrichment in stroma-related gene pathways predict poor survival and resistance to gemcitabine in patients with pancreatic cancer. Clin. Cancer Res. 17, 5793-5800.

Heinemann, V., Haas, M., and Boeck, S. (2012). Systemic treatment of advanced pancreatic cancer. Cancer Treat. Rev. 38, 843-853.

Hingorani et al., (2005). Trp53R172H and KrasG12D cooperate to promote chromosomal instability and widely metastatic pancreatic ductal adenocarcinoma in mice. Cancer Cell 7, 469-483.

Hwang et al., (2008). Cancer-associated stromal fibroblasts promote pancreatic tumor progression. Cancer Res. 68, 918-926.

Ijichi et al., (2011) Inhibiting Cxcr2 disrupts tumor-stromal interactions and improves survival in a mouse model of pancreatic ductal adenocarcinoma. J. Clin. Invest. 121, 4106-4117.

Jacobetz et al., (2013). Hyaluronan impairs vascular function and drug delivery in a mouse model of pancreatic cancer. Gut 62, 112-120.

Kalluri and Zeisberg (2006). Fibroblasts in cancer. Nat. Rev. Cancer 6, 392-401.

Kisseleva et al., (2012). Myofibroblasts revert to an inactive phenotype during regression of liver fibrosis. Proc. Natl. Acad. Sci. USA 109, 9448-9453.

Lawler, J. (2002). Thrombospondin-1 as an endogenous inhibitor of angiogenesis and tumor growth. J. Cell. Mol. Med. 6, 1-12.

Lesina et al., (2011). Stat3/Socs3 activation by IL-6 trans-signaling promotes progression of pancreatic intraepithelial neoplasia and development of pancreatic cancer. Cancer Cell 19, 456-469.

Ma et al., (2006). Identification and characterization of noncalcemic, tissue-selective, nonsecosteroidal vitamin D receptor modulators. J. Clin. Invest. 116, 892-904.

Mahadevan, D., and Von Hoff, D. D. (2007). Tumor-stroma interactions in pancreatic ductal adenocarcinoma. Mol. Cancer Ther. 6, 1186-1197.

Mantoni et al., (2011). Pancreatic stellate cells radioprotect pancreatic cancer cells through beta1-integrin signaling. Cancer Res. 71, 3453-3458.

Mann et al., (2003). Vitamin D3 in patients with various grades of chronic pancreatitis, according to morphological and functional criteria of the pancreas. Dig Dis Sci. 48, 533-538.

Masamune, A., and Shimosegawa, T. (2009). Signal transduction in pancreatic stellate cells. J. Gastroenterol. 44, 249-260.

Nagpal, S., Na, S., and Rathnachalam, R. (2005). Noncalcemic actions of vitamin D receptor ligands. Endocr. Rev. 26, 662-687.

Naveh-Many and Silver (1993). Effects of calcitriol, 22-oxa-calcitriol, and calcipotriol on serum calcium and parathyroid hormone gene expression. Endocrinology 133, 2724-2728.

Neesse et al., (2013). CTGF antagonism with mAb FG-3019 enhances chemotherapy response without increasing drug delivery in murine ductal pancreas cancer. Proc. Natl. Acad. Sci. USA 110, 12325-12330.

Olive et al., (2009) Inhibition of Hedgehog signaling enhances delivery of chemotherapy in a mouse model of pancreatic cancer. Science 324, 1457-1461.

Omary et al., (2007). The pancreatic stellate cell: a star on the rise in pancreatic diseases. J. Clin. Invest. 117, 50-59.

Persons et al., (2010). Anti-growth effect of 1,25-dihydroxyvitamin D3-3-bromoacetate alone or in combination with 5-amino-imidazole-4-carboxamide-1-beta-4-ribofuranoside in pancreatic cancer cells. Anticancer Res. 30, 1875-1880.

Phillips et al., (2003). Rat pancreatic stellate cells secrete matrix metalloproteinases: implications for extracellular matrix turnover. Gut 52, 275-282.

Pietras and Ostman (2010). Hallmarks of cancer: interactions with the tumor stroma. Exp. Cell Res. 316, 1324-1331.

Provenzano et al., (2012). Enzymatic targeting of the stroma ablates physical barriers to treatment of pancreatic ductal adenocarcinoma. Cancer Cell 21, 418-429.

Pylayeva-Gupta et al., (2012). Oncogenic Kras-induced GM-CSF production promotes the development of pancreatic neoplasia. Cancer Cell 21, 836-847.

Rasanen and Vaheri (2010). Activation of fibroblasts in cancer stroma. Exp. Cell Res. 316, 2713-2722.

Sah et al., (2013). Cerulein-induced chronic pancreatitis does not require intra-acinar activation of trypsinogen in mice. Gastroenterology 144, 1076-1085 e1072.

Schafer et al., (1987). The synthesis of proteoglycans in fat-storing cells of rat liver. Hepatology 7, 680-687.

Schneider et al., (2001). Identification of mediators stimulating proliferation and matrix synthesis of rat pancreatic stellate cells. Am. J. Physiol. Cell Physiol. 281, C532-543.

Sherman et al., (2010). AID-induced genotoxic stress promotes B cell differentiation in the germinal center via ATM and LKB1 signaling. Molecular Cell 39, 873-885.

Shimoda et al., (2010). Carcinoma-associated fibroblasts are a rate-limiting determinant for tumour progression. Semin Cell Dev. Biol. 21, 19-25.

Skinner et al., (2006). Vitamin D intake and the risk for pancreatic cancer in two cohort studies. Cancer Epidemiol. Biomarkers Prev. 15, 1688-1695.

Straussman et al., (2012). Tumour micro-environment elicits innate resistance to RAF inhibitors through HGF secretion. Nature 487, 500-504.

Trapnell et al., (2012). Differential gene and transcript expression analysis of RNA-seq experiments with TopHat and Cufflinks. Nature Protocols 7, 562-578.

Treiber et al., (2011). Myeloid, but not pancreatic, RelA/p65 is required for fibrosis in a mouse model of chronic pancreatitis. Gastroenterology 141, 1473-1485, 1485 e1471-1477.

Vonlaufen et al., (2008). Pancreatic stellate cells: partners in crime with pancreatic cancer cells. Cancer Res. 68, 2085-2093.

Wehr et al., (2011). Analysis of the human pancreatic stellate cell secreted proteome. Pancreas 40, 557-566.

Willemer, S., Elsasser, H. P., and Adler, G. (1992). Hormone-induced pancreatitis. Eur. Surg. Res. 24 Suppl 1, 29-39.

Wilson et al., (2012). Widespread potential for growth-factor-driven resistance to anticancer kinase inhibitors. Nature 487, 505-509.

Wolpin et al., (2012). Plasma 25-hydroxyvitamin D and risk of pancreatic cancer. Cancer Epidemiol. Biomarkers Prev. 21, 82-91.

Yanagisawa et al., (1999). Convergence of transforming growth factor-beta and vitamin D signaling pathways on SMAD transcriptional coactivators. Science 283, 1317-1321.

Yoo et al., (2005). Novel antioxidant ameliorates the fibrosis and inflammation of cerulein-induced chronic pancreatitis in a mouse model. Pancreatology 5, 165-176.

Yoshizawa et al., (1997). Mice lacking the vitamin D receptor exhibit impaired bone formation, uterine hypoplasia and growth retardation after weaning. Nat. Genet. 16, 391-396.

Yu et al., (2010). Calcitriol enhances gemcitabine anti-tumor activity in vitro and in vivo by promoting apoptosis in a human pancreatic carcinoma model system. Cell Cycle 9, 3022-3029.

Zeitz et al., (2003) Impaired insulin secretory capacity in mice lacking a functional vitamin D receptor. FASEB J. 17, 509-511.

In view of the many possible embodiments to which the principles of the disclosure may be applied, it should be recognized that the illustrated embodiments are only examples of the disclosure and should not be taken as limiting the scope of the invention. Rather, the scope of the disclosure is defined by the following claims. We therefore claim as our invention all that comes within the scope and spirit of these claims.

We claim:

1. A method of treating pancreatic ductal adenocarcinoma, comprising: administering to a mammalian subject having a pancreatic ductal adenocarcinoma a therapeutically effective amount of calcipotriol; and administering to the mammalian subject a therapeutically effective amount of gemcitabine, thereby reducing tumor volume and/or tumor growth, increasing intratumoral vasculature, and treating the pancreatic ducal adenocarcinoma in the subject.

2. The method of claim 1, wherein the calcipotriol is administered prior to, or concurrently with, the gemcitabine.

3. The method of claim 1, wherein administration of calcipotriol comprises oral, intraperitoneal, or intravenous administration of the calcipotriol.

4. The method of claim 1, wherein the mammalian subject is a human subject.

5. The method of claim 1, wherein administration of gemcitabine comprises oral, intraperitoneal, or intravenous administration of the gemcitabine.

6. The method of claim 1, wherein administration of gemcitabine comprises intraperitoneal administration of the gemcitabine.

7. The method of claim 1, wherein the calcipotriol is administered prior to the gemcitabine.

8. The method of claim 1, wherein administration of calcipotriol comprises intraperitoneal administration of the calcipotriol.

\* \* \* \* \*